United States Patent
Priestley et al.

(10) Patent No.: US 7,122,627 B2
(45) Date of Patent: Oct. 17, 2006

(54) LACTAM INHIBITORS OF HEPATITIS C VIRUS NS3 PROTEASE

(75) Inventors: E. Scott Priestley, Hockessin, DE (US); Carl P. Decicco, Kennett Square, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 144 days.

(21) Appl. No.: 10/010,184

(22) Filed: Dec. 6, 2001

(65) Prior Publication Data

US 2003/0008828 A1 Jan. 9, 2003

Related U.S. Application Data

(63) Continuation-in-part of application No. 09/626,286, filed on Jul. 25, 2000, now abandoned.
(60) Provisional application No. 60/145,631, filed on Jul. 26, 1999.

(51) Int. Cl.
*C07K 5/08* (2006.01)

(52) U.S. Cl. .................. 530/331; 530/330; 514/18; 514/19
(58) Field of Classification Search ................ 530/331, 530/330; 514/18, 19
See application file for complete search history.

(56) References Cited

FOREIGN PATENT DOCUMENTS

| FR | 2 758 329 | 7/1998 |
|---|---|---|
| WO | WO 93/21213 | 10/1993 |
| WO | WO 93/21214 | 10/1993 |
| WO | WO 95/09634 | 4/1995 |
| WO | WO 97/43310 | 11/1997 |
| WO | WO 98/17679 | 4/1998 |
| WO | WO 98/22496 | 5/1998 |
| WO | WO 98/24806 | 6/1998 |
| WO | WO 98/46630 | 10/1998 |
| WO | WO 99/07733 | 2/1999 |
| WO | WO 99/07734 | 2/1999 |
| WO | WO 01/07407 | 2/2001 |

OTHER PUBLICATIONS

Ingallinella et al. (1998) Biochemistry 37:8906–8914.
Matteson et al. (1983) Organometallics 2:1529–1535.
Matteson et al. (1982) Organometallics 1:280–288.
Steinkühler et al. (1998) Biochemistry 37:8899–8905.
Poynard et al. (1998) Lancet 352:1426–1432.
Llinas–Brunet et al. (1998) Bioorg. Med. Chem. Lett. 8:1713–1718.
Roberts and Vellaccio (1983) The Peptides 5:342–429.
Chou and Talalay (1984) Adv. Enzyme Regul. 2:27–55.
Carpino et al. (1984) J. Chem. Soc., Chem. Comm. 201–203.
Myers et al. (1997) J. Am. Chem. Soc. 119:656–673.
D.A. Evans et al. (1990) J. Am. Chem. Soc. 112:4011.
P.D. Edwards et al. (1994) Medicinal Res. Reviews 14:127–194.
D.S. Matteson et al. (1984) Organometallics 3:1284–1288.
I. Ugi et al. (1965) Angew. Chem., Intl. Ed. Eng. 4:472.
D. Hoppe (1974) Angew. Chem., Intl. Ed. Eng. 13:789–804.
R. Roeske (1963) J. Org. Chem. 28:1251–1253.
Albericio et al. (1998) J. Org. Chem. 63:9678–9683.
H. Wenschuh et al. (1996) Tetrahedron Lett. 37:5483–5486.
S.J. Miller et al. (1996) J. Am. Chem. Soc. 118:9606.
G.W. Gribble et al. (1996) J. Heterocyclic Chem. 33:719–726.
Matteson and Majumdar (1979) J. Organometallic Chem. 170:259–264.
Sadhu and Matteson (1985) Organometallics 4:1687–1689.
Steven D. Young et al. (1995) Antimicrobial Agents and Chemotherapy 2602–2605.
Andrew S. Thompson et al. (1995) Tet. Lett., 36:8937–8940.
M.W. Anderson et al. (1989) Chem. Ber., 122:1777–1782.
C. Steinkühler et al. (1996) Journal of Virology 70:6694–6670.
C. Steinkühler et al. (1996) Journal of Biological Chemistry 271:6367–6373.
Taliani et al. (1996) Anal. Biochem. 240:60–67.
Bleth (1996) Methods Enzymol. 248:58–85.

*Primary Examiner*—Jon Weber
*Assistant Examiner*—David Lukton
(74) *Attorney, Agent, or Firm*—Maureen S. Gibbons

(57) ABSTRACT

The present invention relates to lactams of Formula (I):

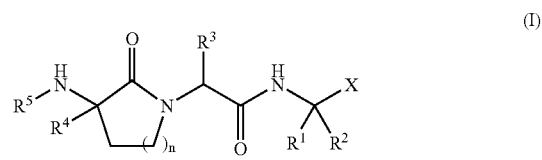

or stereoisomeric forms, stereoisomeric mixtures, or pharmaceutically acceptable salt forms thereof, which are useful as inhibitors of HCV NS3 protease, and to pharmaceutical compositions and diagnostic kits comprising the same, and methods of using the same for treating viral infection or as an assay standard or reagent.

25 Claims, No Drawings

LACTAM INHIBITORS OF HEPATITIS C VIRUS NS3 PROTEASE

This application is a continuation-in-part of U.S. application Ser. No. 09/626,286, filed Jul. 25, 2000, now abandoned, which claims the benefit of U.S. Provisional Application No. 60/145,631, filed Jul. 26, 1999.

FIELD OF THE INVENTION

The present invention relates generally to a novel class of lactams which are useful as serine protease inhibitors, and more particularly as Hepatitis C virus NS3 protease inhibitors. This invention also relates to pharmaceutical compositions comprising these compounds and methods of using the same.

BACKGROUND OF THE INVENTION

Hepatitis C virus (HCV) is the major cause of transfusion and community-acquired non-A, non-B hepatitis worldwide. Approximately 2% of the world's population are infected with the virus. In the Unites States, hepatitis C represents approximately 20% of cases of acute hepatitis. Unfortunately, self-limited hepatitis is not the most common course of acute HCV infection. In the majority of patients, symptoms of acute hepatitis resolve, but alanine aminotransferase (a liver enzyme diagnostic for liver damage) levels often remain elevated and HCV RNA persists. Indeed, a propensity to chrominicity is the most distinguishing characteristic of hepatitis C, occurring in at least 85% of patients with acute HCV infection. The factors that lead to chronicity in hepatitis C are not well defined. Chronic HCV infection is associated with increased incidence of liver cirrhosis and liver cancer. No vaccines are available for this virus, and current treatment is restricted to the use of alpha interferon, which is effective in only 15–20% of patients. Recent clinical studies have shown that combination therapy of alpha interferon and ribavirin leads to sustained efficacy in 40% of patients (Poynard, T. et al. *Lancet* 1998, 352, 1426–1432.). However, a majority of patients still either fail to respond or relapse after completion of therapy. Thus, there is a clear need to develop more effective therapeutics for treatment of HCV-associated hepatitis.

HCV is a positive-stranded RNA virus. Based on comparison of deduced amino acid sequence and the extensive similarity in the 5' untranslated region, HCV has been classified as a separate genus in the Flaviviridae family, which also includes flaviviruses such as yellow fever virus and animal pestiviruses like bovine viral diarrhea virus and swine fever virus. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The RNA genome is about 9.6 Kb in length, and encodes a single polypeptide of about 3000 amino acids. The 5' untranslated region contains an internal ribosome entry site (IRES), which directs cellular ribosomes to the correct AUG for initiation of translation. As was determined by transient expression of cloned HCV cDNAs, the precursor protein is cotranslationally and posttranslationally processed into at least 10 viral structural and nonstructural (NS) proteins by the action of a host signal peptidase and by two distinct viral proteinase activities. The translated product contains the following proteins: core-E1-E2-p7-NS2-NS3-NS4A-NS4B-NS5A-NS5B.

The N-terminal portion of NS3 functions as a proteolytic enzyme that is responsible for the cleavage of sites liberating the nonstructural proteins NS4A, NS4B, NS5A, and NS5B. NS3 has further been shown to be a serine protease. Although the functions of the NS proteins are not completely defined, it is known that NS4A is a protease cofactor and NS5B is an RNA polymerase involved in viral replication. Thus agents that inhibit NS3 proteolytic processing of the viral polyprotein are expected to have antiviral activity.

There are several patents which disclose HCV NS3 protease inhibitors. WO98/17679 describes peptide and peptidomimetic ihibitors with the following formula: $U-E^8-E^7-E^6-E^5-E^4-NH-CH(CH_2G^1)-W^1$, where W is one of a variety of electrophilic groups, including boronic acid or ester. E4 represents either an amino acid or one of a series of peptidomimetic groups, the sythesis of which are not exemplified. The lactam inhibitors described in the present case are not covered.

WO98/22496 discloses peptide inhibitors of the following general formula: $R^9-NH-CH(R^8)-CO-NH-CH(R^7)-CO-N(R^6)-CH(R^5)-CO-NH-CH(R^4)-CO-N(R^3)-CH(R^2)-CO-NH-CH(R^1)-E$ where E either an aldehyde or a boronic acid. $R^1$ represents lower alkyl (optionally substituted by halo, cyano, lower alkylthio, aryl-lower alkylthio, aryl or heteroaryl), lower alkenyl or lower akynyl.

Llinas-Brunet, Bailey et al WO99/07734 have described hexa- to tetra-peptide analogs containing a $P_1$ electrophilic carbonyl group, a phosphonate ester, or an aza-aminoacid analog. Also, Llinas-Brunet, Poupart et al. WO99/07733 describe peptides terminating in a carboxylate. This latter group of compounds are similar to those described by Steinkuhler et al. *Biochemistry* 37, 8899–8905 (1998) and Ingallinella et al. *Biochemistry* 37, 8906–8914 (1998). These investigators report that hexapeptide substrate hydrolysis products are inhibitors of HCV protease. For example, Ac-Asp-Glu-Dpa-Glu-Cha-Cys-OH (SEQ. ID. NO.:1) is reported to have a Ki of <1.0 μM. In related disclosures, Ac-Asp-(D)Asp-Ile-Val-Pro-Cys-OH (SEQ. ID. NO.:2) has been shown to be more effective than its all "L" isomer Llinas-Brunet et al. *Bioorg. Med. Chem. Lett.* 8 1713–1718 (1998).

Additional peptide inhibitors of HCV protease have been disclosed. Hart et al WO9846630 have described heptapeptide analogs containing an ester linkage at the scissile bond. Zhang et al. WO9743310 discloses high molecular weight peptide inhibitors. These compounds are also distinct from the present inventions.

Based on the large number of persons currently infected with HCV and the limited treatments available, it is desirable to discover new inhibitors of HCV NS3 protease.

SUMMARY OF THE INVENTION

Accordingly, one object of the present invention is to provide novel HCV NS3 protease inhibitors.

It is another object of the present invention to provide a novel method of treating HCV infection which comprises administering to a host in need of such treatment a therapeutically effective amount of at least one of the compounds of the present invention or a pharmaceutically acceptable salt form thereof.

It is another object of the present invention to provide pharmaceutical compositions with HCV NS3 protease inhibiting activity comprising a pharmaceutically acceptable carrier and a therapeutically effective amount of at least one of the compounds of the present invention or a pharmaceutically acceptable salt form thereof. It is another object of the present invention to provide a method of inhibiting HCV present in a body fluid sample which comprises treating the body fluid sample with an effective amount of a compound of the present invention. It is another object of the present invention to provide a kit or container containing at least one of the compounds of the present invention in an amount effective for use as a standard or reagent in a test or assay for determining the ability of a potential pharmaceutical to inhibit HCV NS3 protease, HCV growth, or both.

It is another object of the present invention to provide novel compounds for use in therapy.

It is another object of the present invention to provide the use of novel compounds for the manufacture of a medicament for the treatment of HCV.

These and other objects, which will become apparent during the following detailed description, have been achieved by the inventors, discovery that compounds of formula (I):

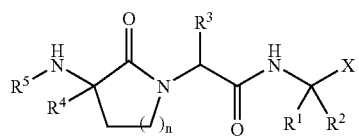

(I)

wherein n, $R^1$, $R^2$, $R^3$, $R^4$, $R^5$, and X are defined below, stereoisomeric forms, mixtures of stereoisomeric forms, or pharmaceutically acceptable salt forms thereof, are effective HCV NS3 protease inhibitors.

DETAILED DESCRIPTION OF PREFERRED EMBODIMENTS

[1] Thus, in a first embodiment, the present invention provides novel compounds of Formula (I):

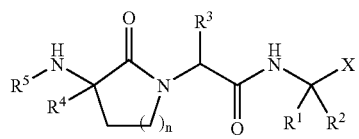

(I)

or a stereoisomer or pharmaceutically acceptable salt form thereof, wherein;

the lactam ring of Formula (I) is substituted with 0–2 $R^b$;

X is selected from the group: $B(OH)_2$, $BY^1Y^2$, and $C(=O)C(=O)NHR^{1a}$;

$Y^1$ and $Y^2$ are independently selected from:
   a) —OH,
   b) —F,
   c) —$NR^{18}R^{19}$,
   d) $C_1$–$C_8$ alkoxy, or when taken together, $Y^1$ and $Y^2$ form:
   e) a cyclic boron ester comprising from 2 to 20 carbon atoms, and, optionally, 1, 2, or 3 heteroatoms which can be N, S, or O;
   f) a cyclic boron amide comprising from 2 to 20 carbon atoms and, optionally, 1, 2, or 3 heteroatoms which can be N, S, or O; or
   g) a cyclic boron amide-ester comprising from 2 to 20 carbon atoms and, optionally, 1, 2, or 3 heteroatoms which can be N, S, or O;

$R^1$ is selected from the group:
   $C_{1-10}$ alkyl substituted with 0–3 $R^a$;
   $C_{2-10}$ alkenyl substituted with 0–3 $R^a$;
   $C_{2-10}$ alkynyl substituted with 0–3 $R^a$; and
   $C_{3-6}$ cycloalkyl substituted with 0–3 $R^a$;

$R^{1a}$ is selected from the group:
   $C_{1-10}$ alkyl substituted with 0–3 $R^a$;
   $C_{2-10}$ alkenyl substituted with 0–3 $R^a$;
   $C_{2-10}$ alkynyl substituted with 0–3 $R^a$; and
   $C_{3-6}$ cycloalkyl substituted with 0–3 $R^a$;

$R^a$ is selected at each occurrence from the group:
   $C_{1-3}$ alkyl, $C_{3-6}$ cycloalkyl, Cl, F, Br, I, $CF_3$, OH, =O, $C_{1-6}$ alkoxy, SH, —S—$C_{1-6}$ alkyl;
   phenyl substituted with 0–3 $R^b$;
   naphthyl substituted with 0–3 $R^b$;
   —O—$(CH_2)_q$-phenyl substituted with 0–3 $R^b$;
   —O—$(CH_2)_q$-naphthyl substituted with 0–3 $R^b$; and
   5–10 membered heteroaryl consisting of carbon atoms and 1–4 heteroatoms selected from the group: O, S, and N, and substituted with 0–3 $R^b$;

$R^b$ is selected at each occurrence from the group:
   $C_{1-6}$ alkyl, Cl, F, Br, I, OH, $C_{1-6}$ alkoxy, —CN, —$NO_2$, $C(O)OR^7$, $NR^dR^d$, $CF_3$, $OCF_3$, and $C_{3-6}$ cycloalkyl;

$R^2$ is H;

alternatively, $R^1$ and $R^2$ combine to form a $C_{3-5}$ cycloalkyl group;

$R^3$ is selected from the group:
   $C_{1-6}$ alkyl substituted with 0–2 $R^a$;
   $C_{2-6}$ alkenyl substituted with 0–2 $R^a$;
   $C_{2-6}$ alkynyl substituted with 0–2 $R^a$;
   —$(CH_2)_q$—$C_{3-6}$ cycloalkyl substituted with 0–2 $R^a$;
   —$(CH_2)_q$-phenyl substituted with 0–2 $R^a$;
   —$(CH_2)_q$-naphthyl substituted with 0–2 $R^a$; and
   —$(CH_2)_q$-5–10 membered heteroaryl consisting of carbon atoms and 1–4 heteroatoms selected from the group: O, S, and N, and substituted with 0–2 $R^a$;

$R^4$ is selected from the group: H,
   $C_{1-6}$ alkyl substituted with 0–3 $R^b$;
   phenyl substituted with 0–3 $R^b$;
   benzyl substituted with 0–3 $R^b$; and
   phenethyl substituted with 0–3 $R^b$;

$R^5$ is H or Q-$R^{5a}$;

Q is 0, 1, 2, or 3 amino acids;

$R^{5a}$ is selected from the group: —$S(O)R^6$, —$S(O)_2R^6$, —$C(O)R^6$, —$C(O)OR^8$, —$C(O)NHR^6$, $C_{1-3}$ alkyl-$R^{6a}$, $C_{2-6}$ alkenyl-$R^{6a}$, and $C_{2-6}$ alkynyl-$R^{6a}$;

$R^6$ is selected from the group:
   $C_{1-6}$ alkyl substituted with 0–3 $R^c$;
   phenyl substituted with 0–3 $R^c$;
   naphthyl substituted with 0–3 $R^c$;
   benzyl substituted with 0–3 $R^c$; and
   5–10 membered heteroaryl consisting of carbon atoms and 1–4 heteroatoms selected from the group: O, S, and N, substituted with 0–3 $R^c$;

$R^{6a}$ is selected from the group:
   phenyl substituted with 0–3 $R^c$;
   naphthyl substituted with 0–3 $R^c$;
   benzyl substituted with 0–3 $R^c$; and 5–10 membered heteroaryl consisting of carbon atoms and 1–4 heteroatoms selected from the group: O, S, and N, substituted with 0–3 $R^c$;

$R^c$ is selected at each occurrence from the group:
$C_{1-4}$ alkyl, $C_{1-4}$ alkoxy, $CF_3$, $OCF_3$, Cl, F, Br, I, $=$O, OH, phenyl, $C(O)OR^7$, $NR^dR^d$, —CN, and $NO_2$;

$R^d$ is selected at each occurrence from the group: H and $CH_3$;

$R^7$ is selected at each occurrence from the group: H and $C_{1-6}$ alkyl;

$R^8$ is selected from the group: $C_{1-6}$ alkyl, benzyl, and $C_{3-6}$ cycloalkyl-methyl;

$R^{18}$ and $R^{19}$ at each occurrence are independently selected from H, $C_{1-4}$ alkyl, aryl($C_{1-4}$ alkyl)-, and $C_3$–$C_7$ cycloalkyl;

n is selected from the group: 1, 2, and 3; and q is selected from the group: 0, 1, and 2.

[2] In a preferred embodiment, the present invention provides novel compounds of Formula (I):

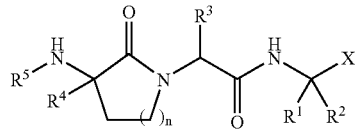

or a stereoisomer or pharmaceutically acceptable salt form thereof, wherein;

the lactam ring of Formula (I) is substituted with 0–2 $R^b$;

X is selected from the group: $B(OH)_2$, $BY^1Y^2$, and $C(=O)C(=O)NHR^{1a}$;

$Y^1$ and $Y^2$ are independently selected from:
a) —OH,
b) —F,
c) —$NR^{18}R^{19}$,
d) $C_1$–$C_8$ alkoxy, or when taken together, $Y^1$ and $Y^2$ form:
e) a cyclic boron ester comprising from 2 to 20 carbon atoms, and, optionally, 1, 2, or 3 heteroatoms which can be N, S, or O;
f) a cyclic boron amide comprising from 2 to 20 carbon atoms and, optionally, 1, 2, or 3 heteroatoms which can be N, S, or O; or
g) a cyclic boron amide-ester comprising from 2 to 20 carbon atoms and, optionally, 1, 2, or 3 heteroatoms which can be N, S, or O;

$R^1$ is selected from the group:
$C_{1-6}$ alkyl substituted with 0–3 $R^a$;
$C_{2-6}$ alkenyl substituted with 0–3 $R^a$;
$C_{2-6}$ alkynyl substituted with 0–3 $R^a$; and
$C_{3-6}$ cycloalkyl substituted with 0–3 $R^a$;

$R^{1a}$ is selected from the group:
$C_{1-10}$ alkyl substituted with 0–3 $R^a$;
$C_{2-10}$ alkenyl substituted with 0–3 $R^a$;
$C_{2-10}$ alkynyl substituted with 0–3 $R^a$; and
$C_{3-6}$ cycloalkyl substituted with 0–3 $R^a$;

$R^a$ is selected at each occurrence from the group:
$C_{1-3}$ alkyl, $C_{3-6}$ cycloalkyl, Cl, F, Br, I, $CF_3$, OH, $=$O, $C_{1-6}$ alkoxy, SH, —S—$C_{1-6}$ alkyl;
phenyl substituted with 0–3 $R^b$;
naphthyl substituted with 0–3 $R^b$;
—O—$(CH_2)_q$-phenyl substituted with 0–3 $R^b$;
—O—$(CH_2)_q$-naphthyl substituted with 0–3 $R^b$; and 5–10 membered heteroaryl consisting of carbon atoms and 1–4 heteroatoms selected from the group: O, S, and N, and substituted with 0–3 $R^b$;

$R^b$ is selected at each occurrence from the group:
$C_{1-6}$ alkyl, Cl, F, Br, I, OH, $C_{1-6}$ alkoxy, —CN, —$NO_2$, $C(O)OR^7$, $NR^dR^d$, $CF_3$, $OCF_3$, and $C_{3-6}$ cycloalkyl;

$R^2$ is H;

alternatively, $R^1$ and $R^2$ combine to form a $C_{3-5}$ cycloalkyl group;

$R^3$ is selected from the group:
$C_{1-6}$ alkyl substituted with 0–2 $R^a$;
$C_{2-6}$ alkenyl substituted with 0–2 $R^a$;
$C_{2-6}$ alkynyl substituted with 0–2 $R^a$;
—$(CH_2)_q$-$C_{3-6}$ cycloalkyl substituted with 0–2 $R^a$;
—$(CH_2)_q$-phenyl substituted with 0–2 $R^a$;
—$(CH_2)_q$-naphthyl substituted with 0–2 $R^a$; and
—$(CH_2)_q$-5–10 membered heteroaryl consisting of carbon atoms and 1–4 heteroatoms selected from the group: O, S, and N, and substituted with 0–2 $R^a$;

$R^4$ is selected from the group: H,
$C_{1-6}$ alkyl substituted with 0–3 $R^b$;
phenyl substituted with 0–3 $R^b$;
benzyl substituted with 0–3 $R^b$; and
phenethyl substituted with 0–3 $R^b$;

$R^5$ is H or Q-$R^{5a}$;

Q is 0, 1, 2, or 3 amino acids;

$R^{5a}$ is selected from the group: —$S(O)R^6$, —$S(O)_2R^6$, —$C(O)R^6$, —$C(O)OR^8$, —$C(O)NHR^6$, $C_{1-3}$ alkyl-$R^{6a}$, $C_{2-6}$ alkenyl-$R^{6a}$, and $C_{2-6}$ alkynyl-$R^{6a}$;

$R^6$ is selected from the group:
$C_{1-6}$ alkyl substituted with 0–3 $R^c$;
phenyl substituted with 0–3 $R^c$;
naphthyl substituted with 0–3 $R^c$;
benzyl substituted with 0–3 $R^c$; and
5–10 membered heteroaryl consisting of carbon atoms and 1–4 heteroatoms selected from the group: O, S, and N, substituted with 0–3 $R^c$;

$R^{6a}$ is selected from the group:
phenyl substituted with 0–3 $R^c$;
naphthyl substituted with 0–3 $R^c$;
benzyl substituted with 0–3 $R^c$; and
5–10 membered heteroaryl consisting of carbon atoms and 1–4 heteroatoms selected from the group: O, S, and N, substituted with 0–3 $R^c$;

$R^c$ is selected at each occurrence from the group:
$C_{1-4}$ alkyl, $C_{1-4}$ alkoxy, $CF_3$, $OCF_3$, Cl, F, Br, I, $=$O, OH, phenyl, $C(O)OR^7$, $NR^dR^d$, —CN, and $NO_2$;

$R^d$ is selected at each occurrence from the group: H and $CH_3$;

$R^7$ is selected at each occurrence from the group: H and $C_{1-6}$ alkyl;

$R^8$ is selected from the group: $C_{1-6}$ alkyl, benzyl, and $C_{3-6}$ cycloalkyl-methyl;

$R^{18}$ and $R^{19}$ at each occurrence are independently selected from H, $C_1$–$C_4$ alkyl, aryl($C_1$–$C_4$ alkyl)-, and $C_3$–$C_7$ cycloalkyl;

n is selected from the group: 1, 2, and 3; and q is selected from the group: 0, 1, and 2.

[3] In a further preferred embodiment, the present invention provides novel compounds of Formula (I), wherein;

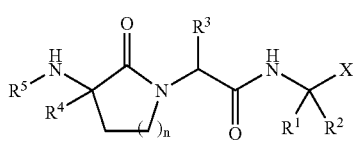

or a stereoisomer or pharmaceutically acceptable salt form thereof, wherein;
the lactam ring of Formula (I) is substituted with 0–2 $R^b$;
X is selected from the group: $B(OH)_2$ and $BY^1Y^2$;
$Y^1$ and $Y^2$ are independently selected from:
  a) —OH,
  b) $C_1$–$C_8$ alkoxy, or
  when taken together, $Y^1$ and $Y^2$ form:
  c) a cyclic boron ester comprising from 2 to 20 carbon atoms;
$R^1$ is selected from the group:
  $C_{1-6}$ alkyl substituted with 0–3 halogen; and
  $C_{2-6}$ alkenyl substituted with 0–3 halogen;
$R^a$ is selected at each occurrence from the group:
  $C_{1-3}$ alkyl, $C_{3-6}$ cycloalkyl, Cl, F, Br, I, $CF_3$, OH, =O, $C_{1-6}$ alkoxy, SH, —S—$C_{1-6}$ alkyl;
  phenyl substituted with 0–3 $R^b$;
  naphthyl substituted with 0–3 $R^b$;
  —O—$(CH_2)_q$-phenyl substituted with 0–3 $R^b$;
  —O—$(CH_2)_q$-naphthyl substituted with 0–3 $R^b$; and
  5–10 membered heteroaryl consisting of carbon atoms and 1–4 heteroatoms selected from the group: O, S, and N, and substituted with 0–3 $R^b$;
$R^b$ is selected at each occurrence from the group:
  $C_{1-6}$ alkyl, Cl, F, Br, I, OH, $C_{1-6}$ alkoxy, —CN, —$NO_2$, $C(O)OR^7$, $NR^dR^d$, $CF_3$, $OCF_3$, and $C_{3-6}$ cycloalkyl;
$R^2$ is H;
$R^3$ is selected from the group:
  $C_{1-6}$ alkyl substituted with 0–2 $R^a$;
  $C_{2-6}$ alkenyl substituted with 0–2 $R^a$;
  $C_{2-6}$ alkynyl substituted with 0–2 $R^a$;
  —$(CH_2)_q$-$C_{3-6}$ cycloalkyl substituted with 0–2 $R^a$;
  —$(CH_2)_q$-phenyl substituted with 0–2 $R^a$;
  —$(CH_2)_q$-naphthyl substituted with 0–2 $R^a$; and
  —$(CH_2)_q$-5–10 membered heteroaryl consisting of carbon atoms and 1–4 heteroatoms selected from the group: O, S, and N, and substituted with 0–2 $R^a$;
$R^4$ is selected from the group: H,
  $C_{1-6}$ alkyl substituted with 0–3 $R^b$;
  phenyl substituted with 0–3 $R^b$;
  benzyl substituted with 0–3 $R^b$; and
  phenethyl substituted with 0–3 $R^b$;
$R^5$ is H or Q-$R^{5a}$;
Q is 0, 1, 2, or 3 amino acids;
$R^{5a}$ is selected from the group: —$S(O)R^6$, —$S(O)_2R^6$, —$C(O)R^6$, —$C(O)OR^8$, —$C(O)NHR^6$, $C_{1-3}$ alkyl-$R^{6a}$, $C_{2-6}$ alkenyl-$R^{6a}$, and $C_{2-6}$ alkynyl-$R^{6a}$;
$R^6$ is selected from the group:
  $C_{1-6}$ alkyl substituted with 0–3 $R^c$;
  phenyl substituted with 0–3 $R^c$;
  naphthyl substituted with 0–3 $R^c$;
  benzyl substituted with 0–3 $R^c$; and
  5–10 membered heteroaryl consisting of carbon atoms and 1–4 heteroatoms selected from the group: O, S, and N, substituted with 0–3 $R^c$;
$R^{6a}$ is selected from the group:
  phenyl substituted with 0–3 $R^c$;
  naphthyl substituted with 0–3 $R^c$;
  benzyl substituted with 0–3 $R^c$; and
  5–10 membered heteroaryl consisting of carbon atoms and 1–4 heteroatoms selected from the group: O, S, and N, substituted with 0–3 $R^c$;
$R^c$ is selected at each occurrence from the group:
  $C_{1-4}$ alkyl, $C_{1-4}$ alkoxy, $CF_3$, $OCF_3$, Cl, F, Br, I, =O, OH, phenyl, $C(O)OR^7$, $NR^dR^d$, —CN, and $NO_2$;
$R^d$ is selected at each occurrence from the group: H and $CH_3$;
$R^7$ is selected at each occurrence from the group: H and $C_{1-6}$ alkyl;
$R^8$ is selected from the group: $C_{1-6}$ alkyl, benzyl, and $C_{3-6}$ cycloalkyl-methyl;
n is selected from the group: 1, 2, and 3; and
q is selected from the group: 0, 1, and 2.

[4] In a more preferred embodiment, the present invention provides novel compounds of Formula (II), wherein;

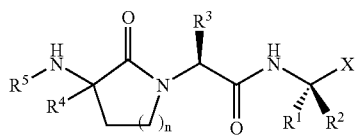

or a stereoisomer or pharmaceutically acceptable salt form thereof, wherein;
X is a boronic acid or a boron ester of formula $BY^1Y^2$;
$Y^1$ an $Y^2$ are independently selected from:
  a) $C_{1-6}$ alkoxy, or
  when taken together, $Y^1$ and $Y^2$ form:
  b) a cyclic boron ester comprising from 2 to 16 carbon atoms;
$R^1$ is selected from the group: ethyl, n-propyl, n-butyl, allyl, 2,2,2-trifluoroethyl, 2,2-difluoroethyl, 3,3,3-trifluoropropyl, 4,4,4-trifluorobutyl, and 3-butenyl;
$R^a$ is selected at each occurrence from the group:
  $C_{1-3}$ alkyl, $C_{3-6}$ cycloalkyl, Cl, F, Br, I, $CF_3$, OH, =O, $C_{1-6}$ alkoxy, SH, —S—$C_{1-6}$ alkyl;
  phenyl substituted with 0–3 $R^b$;
  naphthyl substituted with 0–3 $R^b$;
  —O—$(CH_2)_q$-phenyl substituted with 0–3 $R^b$;
  —O—$(CH_2)_q$-naphthyl substituted with 0–3 $R^b$; and
  5–10 membered heteroaryl consisting of carbon atoms and 1–4 heteroatoms selected from the group: O, S, and N, and substituted with 0–3 $R^b$;
$R^b$ is selected at each occurrence from the group:
  $C_{1-6}$ alkyl, Cl, F, Br, I, OH, $C_{1-6}$ alkoxy, —CN, —$NO_2$, $C(O)OR^7$, $NR^dR^d$, $CF_3$, $OCF_3$, and $C_{3-6}$ cycloalkyl;
$R^2$ is H;
$R^3$ is selected from the group:
  $C_{1-6}$ alkyl substituted with 0–2 $R^a$;
  $C_{2-6}$ alkenyl substituted with 0–2 $R^a$;
  $C_{2-6}$ alkynyl substituted with 0–2 $R^a$;
  —$(CH_2)_q$-$C_{3-6}$ cycloalkyl substituted with 0–2 $R^a$;
  —$(CH_2)_q$-phenyl substituted with 0–2 $R^a$;
  —$(CH_2)_q$-naphthyl substituted with 0–2 $R^a$;

—(CH$_2$)$_q$-5–10 membered heteroaryl consisting of carbon atoms and 1–4 heteroatoms selected from the group: O, S, and N, and substituted with 0–2 R$^a$;

R$^4$ is selected from the group: H, methyl, ethyl, n-propyl, i-propyl, n-butyl, i-butyl, sec-butyl, t-butyl;
phenyl substituted with 0–3 R$^b$;
benzyl substituted with 0–3 R$^b$; and
phenethyl substituted with 0–3 R$^b$;

R$^5$ is H or Q-R$^{5a}$;

Q is 0, 1, or 2 amino acids;

R$^{5a}$ is selected from the group: —S(O)R$^6$, —S(O)$_2$R$^6$, —C(O)R$^6$, —C(O)OR$^8$, —C(O)NHR$^6$, C$_{1-3}$ alkyl-R$^{6a}$, C$_{2-6}$ alkenyl-R$^{6a}$, and C$_{2-6}$ alkynyl-R$^{6a}$;

R$^6$ is selected from the group:
C$_{1-6}$ alkyl substituted with 0–3 R$^c$;
phenyl substituted with 0–3 R$^c$;
naphthyl substituted with 0–3 R$^c$;
benzyl substituted with 0–3 R$^c$; and
5–10 membered heteroaryl consisting of carbon atoms and 1–4 heteroatoms selected from the group: O, S, and N, substituted with 0–3 R$^c$;

R$^{6a}$ is selected from the group:
phenyl substituted with 0–3 R$^c$;
naphthyl substituted with 0–3 R$^c$;
benzyl substituted with 0–3 R$^c$; and
5–10 membered heteroaryl consisting of carbon atoms and 1–4 heteroatoms selected from the group: O, S, and N, substituted with 0–3 R$^c$;

R$^c$ is selected at each occurrence from the group:
C$_{1-4}$ alkyl, C$_{1-4}$ alkoxy, CF$_3$, OCF$_3$, Cl, F, Br, I, =O, OH, phenyl, C(O)OR$^7$, NR$^d$R$^d$, —CN, and NO$_2$;

R$^d$ is selected at each occurrence from the group: H and CH$_3$;

R$^7$ is selected at each occurrence from the group: H and C$_{1-6}$ alkyl;

R$^8$ is selected from the group: C$_{1-6}$ alkyl, benzyl, and C$_{3-6}$ cycloalkyl-methyl;

n is 1 or 2; and q is selected from the group: 0, 1, and 2.

[5] In a further more preferred embodiment, the present invention provides novel compounds of Formula (II), wherein;

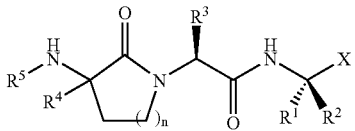

(II)

or a stereoisomer or pharmaceutically acceptable salt form thereof, wherein;

X is a boronic acid or boron ester, wherein the ester is a diol selected from the group: pinanediol, pinacol, 1,2-ethanediol, 1,3-propanediol, 1,2-propanediol, 2,3-butanediol, 1,2-diisopropylethanediol, 5,6-decanediol, and 1,2-dicyclohexylethanediol;

R$^1$ is selected from the group: ethyl, n-propyl, n-butyl, allyl, 2,2,2-trifluoroethyl, 2,2-difluoroethyl, 3,3,3-trifluoropropyl, 4,4,4-trifluorobutyl, and 3-butenyl;

R$^2$ is H;

R$^3$ is selected from the group: n-propyl, n-butyl, i-butyl, n-pentyl, neo-pentyl, cyclohexylmethyl, cyclopentylmethyl, phenyl, t-butoxymethyl, benzyloxymethyl, hydroxymethyl, methoxymethyl, ethoxymethyl, propoxymethyl, and i-propoxymethyl;

R$^4$ is selected from the group: methyl, ethyl, n-propyl, i-propyl, n-butyl, i-butyl, sec-butyl, t-butyl, phenyl, benzyl, and phenethyl;

R$^5$ is H or Q-R$^{5a}$;

Q is 0, 1, or 2 amino acids;

R$^{5a}$ is selected from the group: —S(O)$_2$R$^6$, —C(O)R$^6$, —C(O)OR$^8$, —C(O)NHR$^6$, and —CH$_2$-R$^{6a}$;

R$^6$ is selected from the group:
methyl substituted with 0–3 R$^c$;
ethyl substituted with 0–3 R$^c$;
propyl substituted with 0–3 R$^c$;
butyl substituted with 0–3 R$^c$;
phenyl substituted with 0–3 R$^c$;
naphthyl substituted with 0–3 R$^c$;
benzyl substituted with 0–3 R$^c$; and
quinolinyl substituted with 0–3 R$^c$;

R$^{6a}$ is selected from the group:
phenyl substituted with 0–3 R$^c$;
naphthyl substituted with 0–3 R$^c$;
benzyl substituted with 0–3 R$^c$; and
quinolinyl substituted with 0–3 R$^c$;

R$^c$ is selected at each occurrence from the group:
methyl, ethyl, n-propyl, i-propyl, n-butyl, i-butyl, t-butyl, methoxy, ethoxy, propoxy, i-propoxy, CF$_3$, OCF$_3$, Cl, F, Br, I, OH, phenyl, C(O)OH, NH$_2$, —CN, and NO$_2$;

R$^8$ is methyl, ethyl, n-propyl, i-propyl, n-butyl, i-butyl, t-butyl, phenyl, and benzyl; and n is 1 or 2.

[6] In an even more preferred embodiment, the present invention provides novel compounds of Formula (II), wherein;

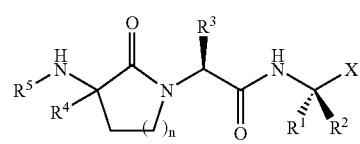

(II)

or a stereoisomer or pharmaceutically acceptable salt form thereof, wherein;

X is a boronic acid or a boron ester of formula BY$^1$Y$^2$;

Y$^1$ and Y$^2$ are individually selected from C$_1$–C$_6$ alkoxy, or when taken together, Y$^1$ and Y$^2$ form a cyclic boron ester where said chain or ring contains from 2 to 14 carbon atoms;

R$^1$ is selected from the group: ethyl, n-propyl, n-butyl, allyl, 2,2,2-trifluoroethyl, 2,2-difluoroethyl, 3,3,3-trifluoropropyl, 4,4,4-trifluorobutyl, and 3-butenyl;

R$^2$ is H;

R$^3$ is selected from the group: i-butyl, neo-pentyl, cyclohexylmethyl, t-butoxymethyl, benzyloxymethyl, hydroxymethyl, and phenyl;

R$^4$ is selected from the group: ethyl, n-propyl, i-propyl, R-2-butyl, S-2-butyl, phenyl, benzyl, and phenethyl;

R$^5$ is selected from the group: H,
benzyl,
m-methylphenylsulfonyl,
m-trifluoromethylphenylsulfonyl,
p-i-propylphenylsulfonyl,
p-propylphenylsulfonyl,
p-t-butylphenylsulfonyl,
p-carboxylphenylsulfonyl, 4-(1,1')biphenylsulfonyl,
1-naphthylsulfonyl,
2-naphthylsulfonyl,
8-quinolinylsulfonyl,
pyrazin-2-ylcarbonyl,
n-butylsulfonyl,
N-phenylaminocarbonyl,
N-(p-n-butylphenyl)aminocarbonyl,
benzyloxycarbonyl,
methoxycarbonyl,
t-butyloxycarbonyl,
benzoyl,
methanesulfonyl,
phenylsulfonyl,
o-nitrophenylsulfonyl,
m-nitrophenylsulfonyl, and
m-aminophenylsulfonyl; and
n is 1 or 2.

[7] In a further even more preferred embodiment, the present invention provides novel compounds of Formula (II), wherein;

X is a boronic acid or boron ester, wherein the ester is a diol selected from the group: pinanediol, pinacol, 1,2-ethanediol, 1,3-propanediol, 1,2-propanediol, 2,3-butanediol, 1,2-diisopropylethanediol, 5,6-decanediol, and 1,2-dicyclohexylethanediol;

$R^1$ is selected from the group: ethyl, n-propyl, n-butyl, allyl, 2,2,2-trifluoroethyl, 2,2-difluoroethyl, 3,3,3-trifluoropropyl, 4,4,4-trifluorobutyl, and 3-butenyl;

$R^2$ is H;

$R^3$ is selected from the group: i-butyl, neo-pentyl, cyclohexylmethyl, t-butoxymethyl, benzyloxymethyl, hydroxymethyl, and phenyl;

$R^4$ is selected from the group: ethyl, n-propyl, i-propyl, R-2-butyl, S-2-butyl, phenyl, benzyl, and phenethyl;

$R^5$ is selected from the group: H,
  benzyl,
  m-methylphenylsulfonyl,
  m-trifluoromethylphenylsulfonyl,
  p-i-propylphenylsulfonyl,
  p-propylphenylsulfonyl,
  p-t-butylphenylsulfonyl,
  p-carboxylphenylsulfonyl,
  4-(1,1')biphenylsulfonyl,
  1-naphthylsulfonyl,
  2-naphthylsulfonyl,
  8-quinolinylsulfonyl,
  pyrazin-2-ylcarbonyl,
  n-butylsulfonyl,
  N-phenylaminocarbonyl,
  N-(p-n-butylphenyl)aminocarbonyl,
  benzyloxycarbonyl,
  methoxycarbonyl,
  t-butyloxycarbonyl,
  benzoyl,
  methanesulfonyl,
  phenylsulfonyl,
  o-nitrophenylsulfonyl,
  m-nitrophenylsulfonyl, and
  m-aminophenylsulfonyl; and n is 1 or 2.

[8] In another preferred embodiment, the compound of Formula (I) is selected from the group:

(1R)-1-({(2S)-3-cyclohexyl-2-(3-isopropyl-3-({(2S)-3-methyl-2-((2-pyrazinylcarbonyl)amino)butanoyl}amino)-2-oxo-1-pyrrolidinyl)propanoyl}amino)-3-butenylboronic acid (+)-pinanediol ester;

(1R)-1-({(2S)-3-cyclohexyl-2-(3-isopropyl-3-({(2S)-3-methyl-2-((2-pyrazinylcarbonyl)amino)butanoyl}amino)-2-oxo-1-piperidinyl)propanoyl}amino)-3-butenylboronic acid (+)-pinanediol ester;

(1R)-1-(({3-((methylsulfonyl)amino)-2-oxohexahydro-1H-azepin-1-yl}acetyl)amino)propylboronic acid (+)-pinanediol ester;

(1R)-1-{((2S)-2-(3-amino-3-isopropyl-2-oxo-1-pyrrolidinyl)-3-cyclohexylpropanoyl)amino}propylboronic acid (+)-pinanediol ester hydrochloride;

1R)-1-(((2S)-2-{3-(((1,1'-biphenyl)-4-ylsulfonyl)amino)-3-isopropyl-2-oxo-1-pyrrolidinyl}-3-cyclohexylpropanoyl)amino)propylboronic acid (+)-pinanediol ester;

(1R)-1-{((2S)-3-cyclohexyl-2-(3-isopropyl-2-oxo-3-{((4-propylphenyl)sulfonyl)amino}-1-pyrrolidinyl)propanoyl)amino}propylboronic acid (+)-pinanediol ester;

(1R)-1-(((2S)-3-cyclohexyl-2-{3-isopropyl-3-((1-naphthylsulfonyl)amino)-2-oxo-1-pyrrolidinyl}propanoyl)amino)propylboronic acid (+)-pinanediol ester;

(1R)-1-(((2S)-2-{3-((anilinocarbonyl)amino)-3-isopropyl-2-oxo-1-pyrrolidinyl}-3-cyclohexylpropanoyl)amino)propylboronic acid (+)-pinanediol ester;

(1R)-1-{((2S)-3-cyclohexyl-2-(3-isopropyl-3-{((3-methylphenyl)sulfonyl)amino}-2-oxo-1-pyrrolidinyl)propanoyl)amino}propylboronic acid (+)-pinanediol ester;

(1R)-1-{((2S)-3-cyclohexyl-2-(3-isopropyl-3-{((3-methylphenyl)sulfonyl)amino}-2-oxo-1-pyrrolidinyl)propanoyl)amino}propylboronic acid (1R)-1-{((3-{((benzyloxy)carbonyl)amino}-3-isopropyl-2-oxo-1-pyrrolidinyl)(phenyl)acetyl)amino}propylboronic acid (+)-pinanediol ester;

(1R)-1-{((3-amino-3-isopropyl-2-oxo-1-pyrrolidinyl)(phenyl)acetyl)amino}propylboronic acid (+)-pinanediol ester hydrochloride;

(1R)-1-{({3-isopropyl-3-((methylsulfonyl)amino)-2-oxo-1-pyrrolidinyl}(phenyl)acetyl)amino}propylboronic acid (+)-pinanediol ester;

(1R)-1-{((3-isopropyl-2-oxo-3-{((4-propylphenyl)sulfonyl)amino}-1-pyrrolidinyl)(phenyl)acetyl)amino}propylboronic acid (+)-pinanediol ester;

(1R)-1-{((2S)-2-(3-{((benzyloxy)carbonyl)amino}-3-isopropyl-2-oxo-1-pyrrolidinyl)-4-methylpentanoyl)amino}propylboronic acid (+)-pinanediol ester;

(1R)-1-{((2S)-2-(3-amino-3-isopropyl-2-oxo-1-pyrrolidinyl)-4-methylpentanoyl)amino}propylboronic acid (+)-pinanediol ester hydrochloride;

(1R)-1-(((2S)-2-{3-isopropyl-3-((methylsulfonyl)amino)-2-oxo-1-pyrrolidinyl}-4-methylpentanoyl)amino)propylboronic acid (+)-pinanediol ester;

(1R)-1-{((2S)-2-(3-isopropyl-2-oxo-3-{((4-propylphenyl)sulfonyl)amino}-1-pyrrolidinyl)-4-methylpentanoyl)amino}propylboronic acid (+)-pinanediol ester;

(1R)-1-({(2S)-3-cyclohexyl-2-(3-ethyl-3-({(2S)-3-methyl-2-((2-pyrazinylcarbonyl)amino)butanoyl}amino)-2-oxo-1-pyrrolidinyl)propanoyl}amino)-3-butenylboronic acid (+)-pinanediol ester;

(1R)-1-{((2S)-2-(3-{((benzyloxy)carbonyl)amino}-3-isopropyl-2-oxo-1-piperidinyl)-3-cyclohexylpropanoyl)amino}propylboronic acid (+)-pinanediol ester;

(1R)-1-{({3-((tert-butoxycarbonyl)amino)-3-isopropyl-2-oxo-1-piperidinyl}(phenyl)acetyl)amino}propylboronic acid (+)-pinanediol ester;

(1R)-1-{((3-amino-3-isopropyl-2-oxo-1-piperidinyl)(phenyl)acetyl)amino}propylboronic acid hydrochloride (+)-pinanediol ester;

(1R)-1-{({3-isopropyl-3-((methoxycarbonyl)amino)-2-oxo-1-piperidinyl}(phenyl)acetyl)amino}propylboronic acid (+)-pinanediol ester;

(1R)-1-{((3-(benzoylamino)-3-isopropyl-2-oxo-1-piperidinyl)(phenyl)acetyl)amino}propylboronic acid (+)-pinanediol ester;

(1R)-1-{({3-isopropyl-3-((methylsulfonyl)amino)-2-oxo-1-piperidinyl}(phenyl)acetyl)amino}propylboronic acid (+)-pinanediol ester; and (1R)-1-{((3-isopropyl-3-{((3-methylphenyl)sulfonyl)amino}-2-oxo-1-piperidinyl)(phenyl)acetyl)amino}propylboronic acid (+)-pinanediol ester;

or a pharmaceutically acceptable salt form thereof.

In another embodiment, the present invention provides a novel pharmaceutical composition comprising a pharmaceutically acceptable carrier and a therapeutically effective amount of a compound of Formula (I) or pharmaceutically acceptable salt form thereof.

In another embodiment, the present invention provides a novel method of treating HCV infection which comprises administering to a host in need of such treatment a therapeutically effective amount of a compound of Formula (I) or pharmaceutically acceptable salt form thereof.

In another embodiment, the present invention provides a novel method of inhibiting HCV NS3 protease which comprises contacting HCV NS3 protease with a therapeutically effective amount of a compound of Formula (I) or pharmaceutically acceptable salt form thereof.

In another embodiment, the present invention provides a novel method of inhibiting HCV NS3 protease comprising contacting HCV NS3 protease with a compound of Formula (I) for a time and under conditions effective to inhibit HCV NS3 protease.

In another embodiment, the present invention provides a novel method of inhibiting HCV NS3 protease in a cell comprising contacting HCV NS3 protease with a compound of Formula (I) for a time and under conditions effective to inhibit HCV NS3 protease.

In another embodiment, the present invention provides a novel method of inhibiting HCV NS3 protease in a mammal comprising contacting HCV NS3 protease with a compound of Formula (I) for a time and under conditions effective to inhibit HCV NS3 protease.

In another embodiment, the present invention provides novel compounds of Formula (I) or pharmaceutically acceptable salt forms thereof for use in therapy.

In another embodiment, the present invention provides the use of novel compounds of Formula (I) or pharmaceutically acceptable salt forms thereof for the manufacture of a medicament for the treatment of HCV.

Definitions

The compounds herein described have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, cyclopentyl, or cyclohexyl. $C_{3-6}$ cycloalkyl, is intended to include $C_3$, $C_4$, $C_5$, and $C_6$ cycloalkyl groups. "Alkenyl" or "alkenylenen" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo, preferably fluoro, chloro, and bromo. "Counterion" is used to represent a small, negatively charged species such as chloride, bromide, hydroxide, acetate, or sulfate.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles, including heteroaryls, include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro(2,3-b)tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred 5 to 10 membered heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles. Preferred 5 to 10 membered heteroaryls include, but are not limited to, pyridinyl, furanyl, thienyl, pyrrolyl, pyrazolyl, pyrazinyl, imidazolyl, indolyl, benzimidazolyl, 1H-indazolyl, benzotriazolyl, benzisoxazolyl, benzoxazolyl, benzthiazolyl, and benzisothiazolyl. Preferred 5 to 6 membered heteroaryls include, but are not limited to, pyridinyl, furanyl, thienyl, pyrazolyl, pyrazinyl, and imidazolyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

In addition to abbreviations known by one skilled in the art for the designation of natural amino acids, abbreviations, known by one skilled in the art, used herein for modified and unusual amino acids are as follows: "Dpa" means diphenylalanine; "Cha" means cyclohexylalanine; "boroAlg-OH" means 2-amino-4-penten-boronic acid"; "Edans" means 5-[(2'-aminoethyl)amino]naphthylenesulfonic acid; "Abuψ(COO)" mean 2-aminobutyric acid bonded through an ester bond; and "Dabcyl" means 4-[[4'-(dimethylamino)-phenyl]azo ]benzoic acid.

The term "boronic acid" represents —B(OH)$_2$. As used herein, the term "boronic acid ester" or "boron ester" is intended to represent esterified versions of boronic acid, for example, —BO$_2$R and —B(OR)$_2$, wherein —BO$_2$R represents a boronic acid esterified by a diol moiety R and —B(OR)$_2$ represents a boronic acid esterified by two separate OR moieties. Examples of useful diols for esterification with the boronic acids are pinanediol, pinacol, 1,2-ethanediol, 1,3-propanediol, 1,2-propanediol, 2,3-butanediol, 1,2-diisopropylethanediol, 5,6-decanediol, and 1,2-dicyclohexylethanediol.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa, 1985, p. 1418, the disclosure of which is hereby incorporated by reference.

Since prodrugs are known to enhance numerous desirable qualities of pharmaceuticals (e.g., solubility, bioavailability, manufacturing, etc. . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit HCV infection or treat the symptoms of HCV infection in a host. The combination of compounds is preferably a synergistic combination. Synergy, as described for example by Chou and Talalay, *Adv. Enzyme Regul.* 1984, 22, 27–55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

As used herein, the term "treat" or "treating" refers to: (i) preventing a disease, disorder or condition from occurring in an animal which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The compounds of this invention are intended to interact with the catalytic serine hydroxyl of Hepatitis C NS3 protease, and therefore incorporate an electrophilic moiety capable of such interaction. In the synthetic schemes below, this moiety, or its synthetic equivalent or precursor, is referred to as a "serine trap" and is defined by formula 9.

A series of γ-lactams of formula 12 are prepared by the method outlined in Scheme 1. Cbz protected, $R^4$-substituted amino acid 1 is treated with paraformaldehyde and p-toluenesulfonic acid to give oxazolidinone 2. Subsequent alkylation with allyl bromide provides the racemic disubstituted oxazolidinone 3. Treatment with sodium methoxide in methanol affords amino acid methyl ester 4. The olefin in 4 is cleaved by ozonolysis to give aldehyde 5. Reductive amination of aldehyde 5 with amino acid methyl ester 6, followed by lactamization provides the lactam 7. Saponification of the methyl ester affords acid 8, which is coupled to serine trap 9 (see subsequent discussion) using either the phosphonium salt PyAOP (Carpino, et al. *J. Chem. Soc., Chem. Commun.* 1994, 201–203.) or by in situ formation of a mixed anhydride of acid 8 and subsequent aminolysis with 9. Catalytic hydrogenation of the resulting 10 affords amine hydrochloride salt 11, which may be acylated, sulfonylated, reductively alkylated, etc. to provide 12 as a mixture of two diastereomers epimeric at the chiral center bearing substituent $R_4$.

Scheme 1

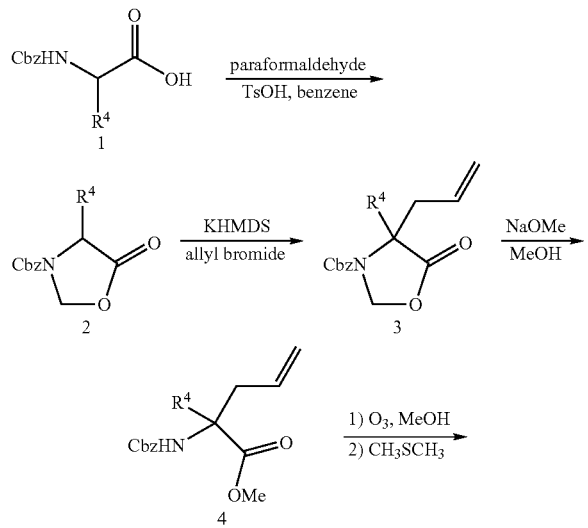

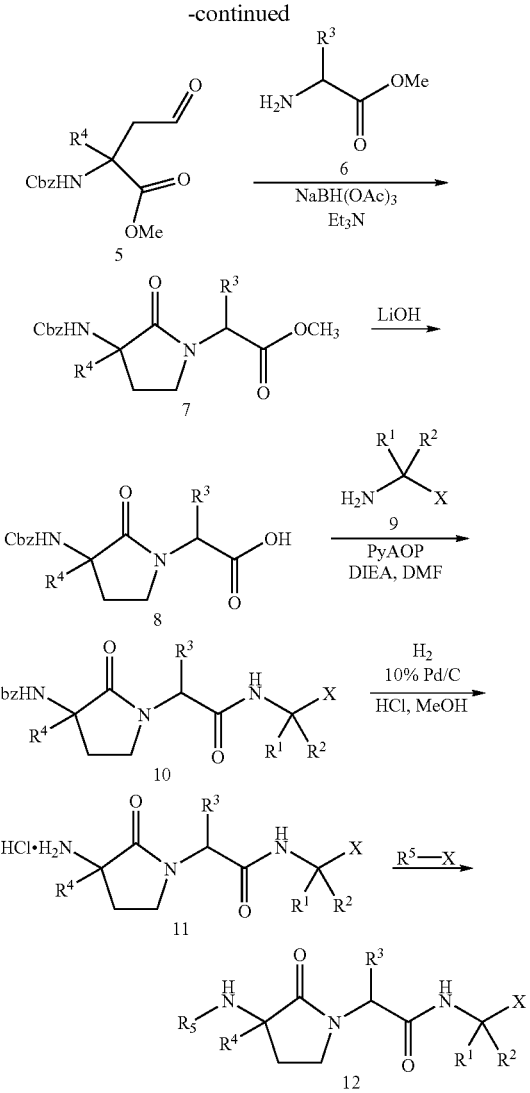

Many of the Cbz protected amino acids 1 and amino acid methyl esters 6 are commercially available or may be prepared from commercial amino acid derivatives by simple protecting group manipulations. Others may be synthesized in racemic form using the Strecker synthesis or amidomalonate synthesis. In addition, the Myers pseudoephedrine glycinamide alkylation method (Myers, A. G.; Gleason, J. L.; Yoon, T; Kung, D. W. *J. Am. Chem. Soc.* 1997, 119, 656–673) and the Evans electrophilic azidation (Evans, D. A.; Britton, T. C.; Ellman, J. A.; Dorow, R. L. *J. Am. Chem. Soc.* 1990, 112, 4011) may be used to prepare unnatural amino acids in enantiomerically pure form.

The serine trap 9 may be either an α-amino boronic ester (X=$BO_2R$) or the reduced form of an α-keto amide (X=CH(OH)CONHR) or other electrophilic carbonyl derivative known to one skilled in the art (Edwards, P. D.; Bernstein, P. R. *Medicinal Res. Reviews* 1994, 14, 127–194, and references cited therein). Scheme 2 shows the synthetic route to monosubstituted amino boronic esters 20 (For a general reference to synthesis of peptide boronic esters, see: Kettner, C.; Forsyth, T. *Houben-Weyl Methods of Organic Chemistry* 1999, in press). Grignard reagent 13 is reacted with a trialkyl borate ester 14, providing boronate 15. Transesterification with (+)-pinanediol 16 affords the cyclic ester 17. This ester ultimately yields enantiomerically pure 20 with L-configuration. Substitution of pinacol for pinanediol yields racemic product. Homologation of 17 with the anion of dichloromethane gives the α-chloro boronic ester 18. (Matteson, D. S.; Majumdar, D. *Organometallics* 1983, 2, 1529–1535) Displacement of chloride by lithium bis(trimethylsilyl)amide, gives silyl amine 19, which is converted to the amine hydrochloride 20 with anhydrous HCl. (Matteson, D. S., Sadhu, K. M. *Organometallics* 1984, 3, 1284–1288.) Note that compounds of formula 20 are a specific instance of serine trap 9 for which X=BO$_2$R.

α,α-Disubstituted amino boronic esters 23 may be prepared as shown in Scheme 3. An isocyanide 21 (commercially available or synthesized by methods known to one skilled in the art. See for instance: Ugi, I.; et al. *Angew. Chem., Intl. Ed. Eng.* 1965, 4, 472.) is metallated with an alkyllithium or lithium dialkyl amide base (Hoppe, D. *Angew. Chem., Intl. Ed. Eng.* 1974, 13, 789–804 and reacted with a trialkyl borate ester. Tranesterification with pinanediol affords α-isocyanoboronic ester 22. Hydrolysis of 22 in conc. HCl/MeOH yields the α,α-disubstituted amino boronic ester 23, which is a specific instance of formula 9 for which X=BO$_2$R and neither R$^1$ nor R$^2$ are hydrogen.

Scheme 2
Error! Objects Cannot be Created from Editing Field Codes.

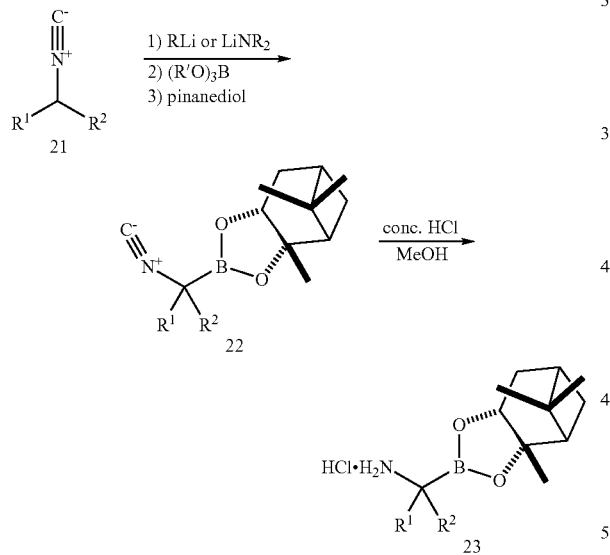

Scheme 3

α-Ketoamides and other electrophilic ketone derivatives are generally introduced in the hydroxy form and oxidized to the active ketone form in the final synthetic step. Scheme 4 illustrates the synthesis of α-ketoamide γ-lactam peptidomimetics. Other electrophilic ketone derivatives may be prepared analogously (Edwards, P. D.; Bernstein, P. R. *Medicinal Res. Reviews* 1994, 14, 127–194, and references cited therein). R$^1$ substituted acrylate ester 24 is aminohydroxylated and subsequently deprotected to give amino alcohol 25 (Note that this structure is a specific instance of formula 9, for which X=CH(OH)COOMe). The amino alcohol is coupled to acid 8 to give 26. Saponification with LiOH affords acid 27, which is coupled to an amine Y—NH$_2$, to give hydroxy amide 28. Hydrogenation of the Cbz group, followed by acylation, sulfonylation, reductive amination, etc. of the resulting amine 29 provides 30. Oxidation with Dess-Martin periodinane affords the α-keto amide 31 (a specifcic instance of formula 12, for which X=COCONY).

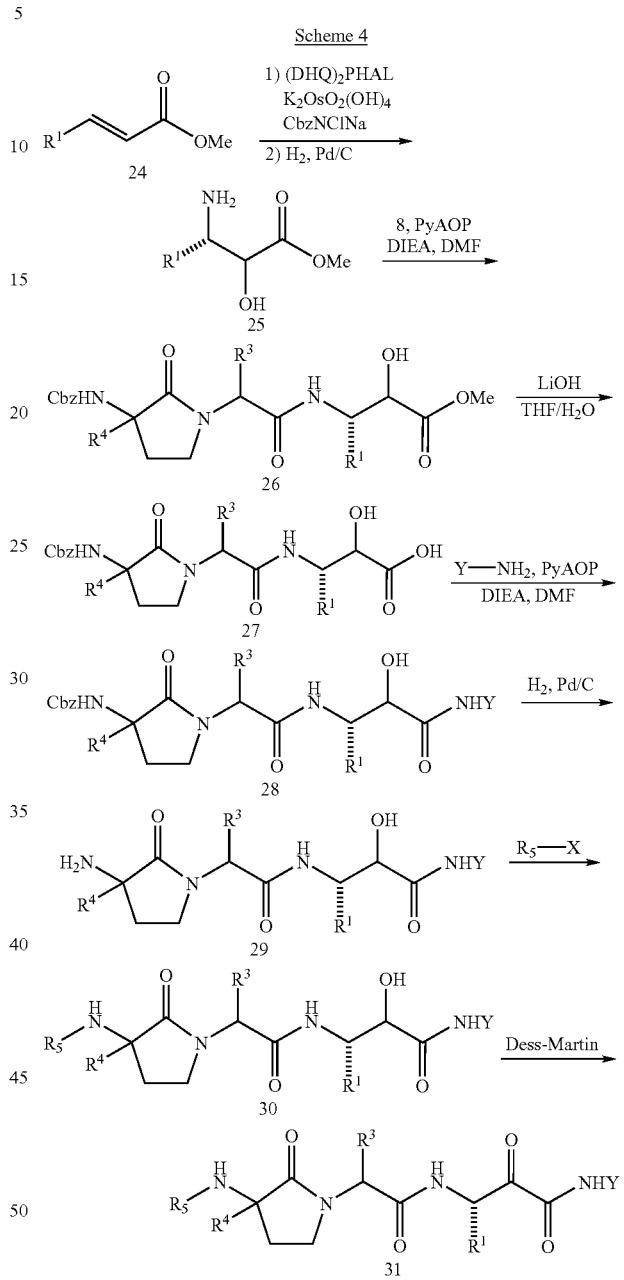

A series of δ-lactam derivatives of formula 40 are prepared by the method outlined in Scheme 5. Allylated, R$^4$ substituted amino acid methyl ester 4, prepared as shown in Scheme 1, is hydroborated and oxidized to alcohol 32. Swern oxidation affords aldehyde 33, which is reductively aminated with R$^3$ substituted amino acid t-butyl ester 34 to afford amine 35. Saponification of the methyl ester in 35, followed by cyclization affords lactam 36. The t-butyl ester is removed with trifluoroacetic acid to give acid 37. Coupling acid 37 to serine trap 9 with PyAOP or via a mixed anhydride affords compounds of formula 38. Catalytic hydrogenation provides amine hydrochloride 39, which may be acylated, sulfonylated, reductively alkylated, etc. to provide δ-lactams of formula 40. Numerous amino acid t-butyl esters 34 are commercially available or may be synthesized by methods known to one skilled in the art (Roeske, R. *J. Org. Chem.* 1963, 28, 1251–1253).

Scheme 5

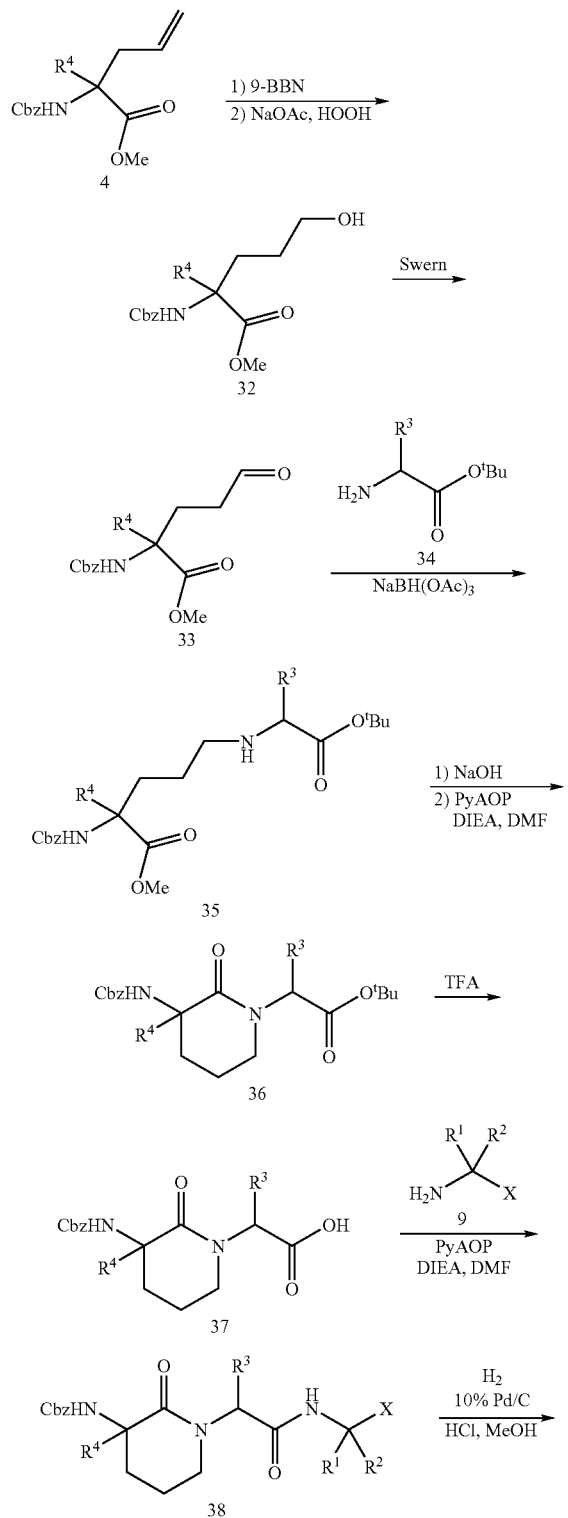

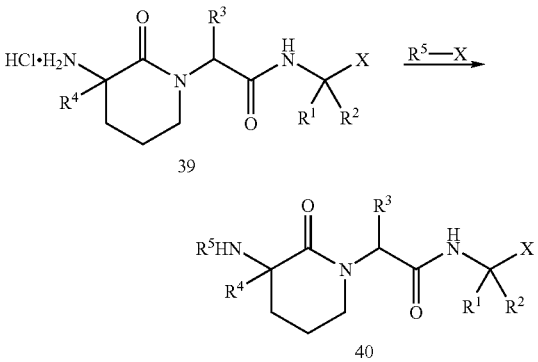

A series of ε-lactams of formula 49 may be synthesized by the method shown in Scheme 6. R⁴ substituted oxazolidinone 3 is hydrolyzed to acid 41 with NaOH. The acid is coupled to R³ substituted-N-allyl amino acid methyl ester 42 using activating reagents suitable for hindered peptide coupling reactions (Albericio, et al. *J. Org. Chem.* 1998, 63, 9678–9683. Wenschuh, H., et al. *Tetrahedron Lett.* 1996, 37, 5483–5486.) to afford dipeptide 43. Ring closing olefin metathesis with ruthenium catalyst 44 (Miller, S. J. et al. *J. Am. Chem. Soc.* 1996, 118, 9606.) affords the lactam 45. The methyl ester in 45 is saponified to provide acid 46. Coupling to serine trap 9 gives 47. Catalytic hydrogenation removes the Cbz group and the olefin to provide amine hydrochloride 48, which may be acylated, sulfonylated, reductively alkylated, etc. to provide δ-lactams of formula 49. Alternatively, the olefin in 47 may be subjected to a variety of procedures (dihydroxylation, epoxidation followed by nucleophilic opening, etc.) to introduce substituents on the lactam ring prior to the final two steps of the synthesis. R³ substituted-N-allyl amino acid methyl esters 42 may be prepared from R³-substituted α-bromo esters ((Gribble, G. W.; Hirth, B. H. *J. Heterocyclic Chem.* 1996, 33, 719–726.)

Scheme 6

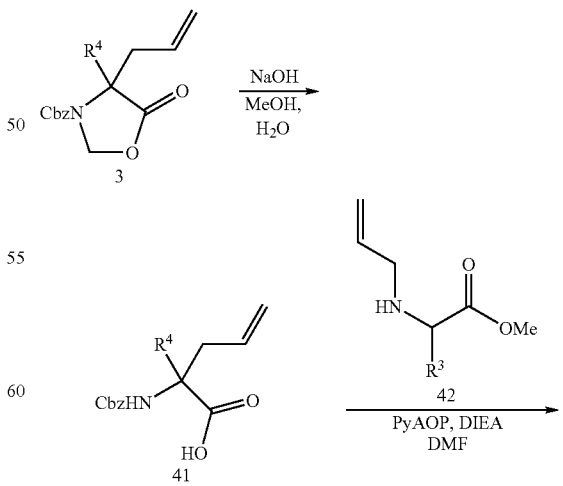

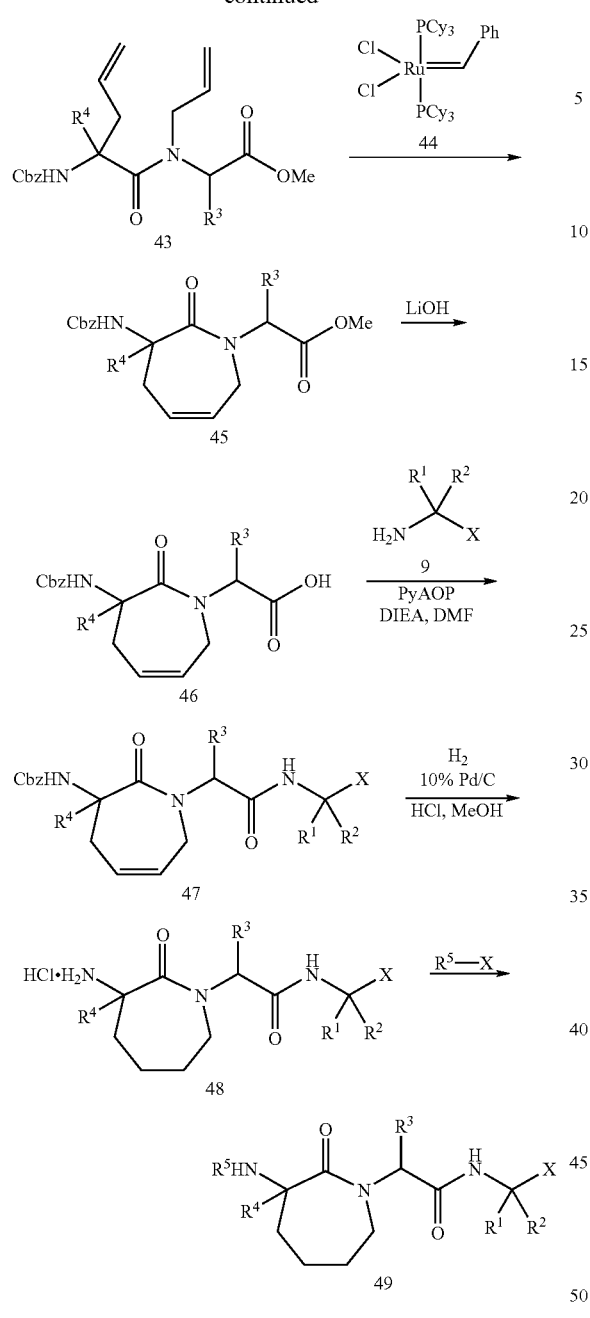

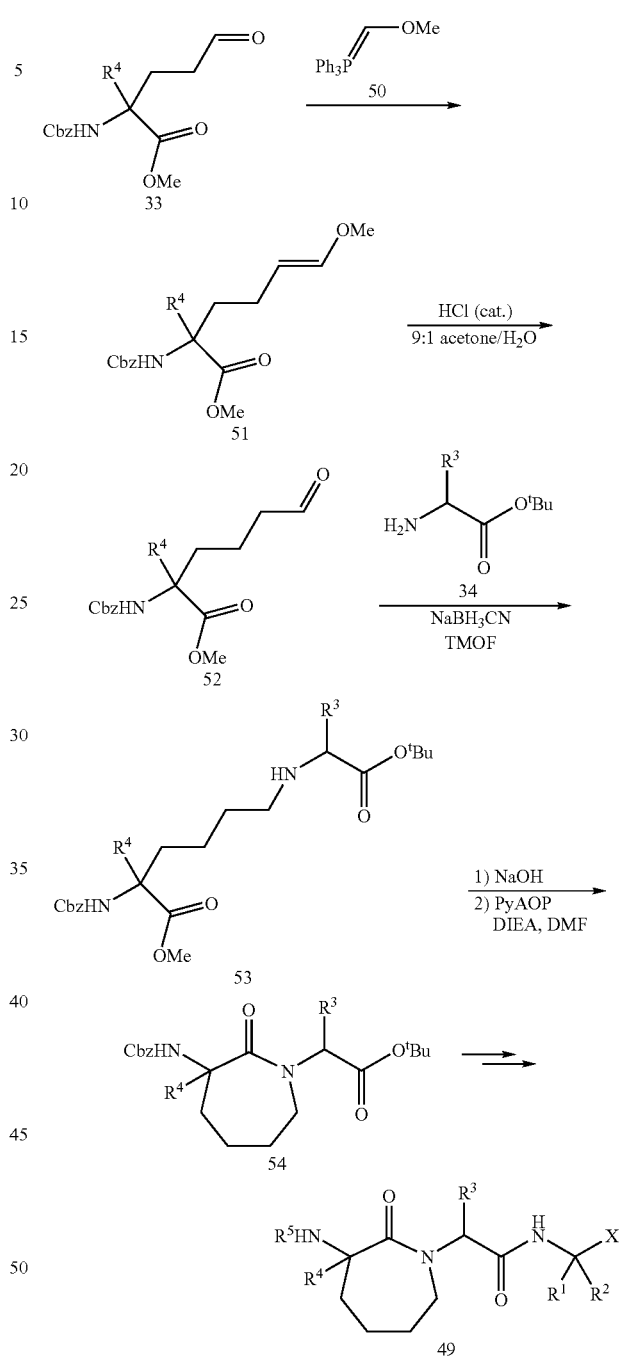

An alternative route to the series of ε-lactams of formula 49 is shown in Scheme 7. This route is applicable for cases in which R³ and R⁴ are too sterically demanding to allow coupling of 41 and 42 in Scheme 6. R⁴-substituted aldehyde 33 (see Scheme 5 for preparation) is treated with phosphonium ylide 50 to afford enol ether 51. The enol ether is hydrolyzed to aldehyde 52. The aldehyde is reductively aminated with amine 34 (see Scheme 5) using sodium cyanoborohydride in trimethyl orthoformate to afford 53. Saponification of the methyl ester, followed by cyclization affords lactam 54. Lactam 54 may be transformed into 49 following the same procedure employed in Scheme 5 to convert 36 to 40.

Preparation of α-aminoboronic Acids.

Preparation of α-aminoboronic acids are well known in the art. Scheme 8 shows the synthesis of α-aminoboronic acids containing sidechains where R is ethyl, allyl, vinyl, and cyclopropyl. A Grignard reagent is added to a trialkyl boronate to give a substituted dialkyl boronate. Transesterification with a suitable diol protecting group gives the boronate ester 2. 2 is shown protected as the pinanediol ester. Pinanediol is the preferred protecting group, but other diol protecting groups are known to those skilled in the art, for example, a C2 symmetrical diol such as (R,R)2,3-butandiol and (R,R)dicyclohexaneethanediol can also be used. The α-chloroalkyl intermediate 3 is obtained by the addition of the anion of methylene chloride to the boronic acid ester. $Li^+CHCl_2^-$ is prepared in situ by the addition of LDA to a −78° C. solution of the alkyl boronic acid ester in methylene chloride. Alternately, $CHCl_2^-Li^+$ is prepared by reacting n-butyl lithium with methylene chloride at −100° C. followed by the addition of the alkyl boronic acid 2. $ZnCl_2$ is added to more hindered alkyl boronic acid. 3 is treated with the lithium salt of hexamethyldisilazane to give the bis-silane protected amine 4. Compound 4 is treated with either anhydrous HCl or trifluoroacetic acid to give the amine 5 as a hydrochloride salt or trifluoroacetate salt.

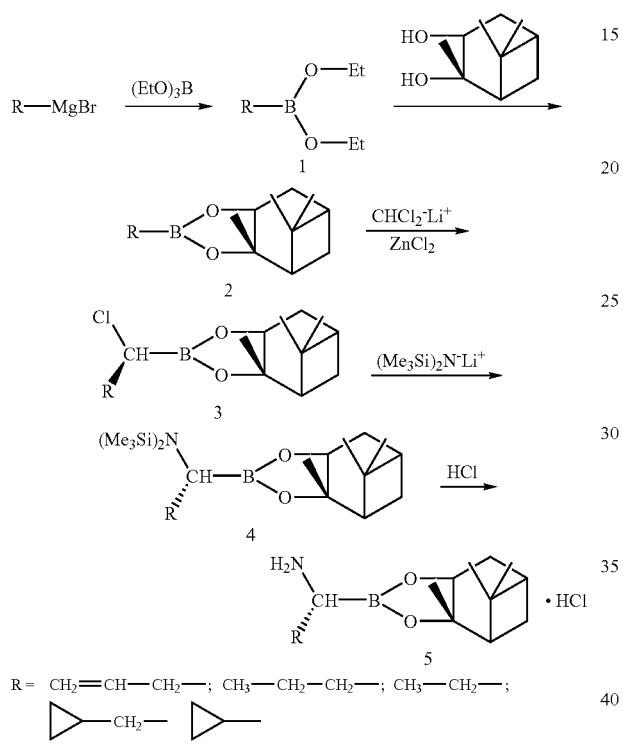

Scheme 8

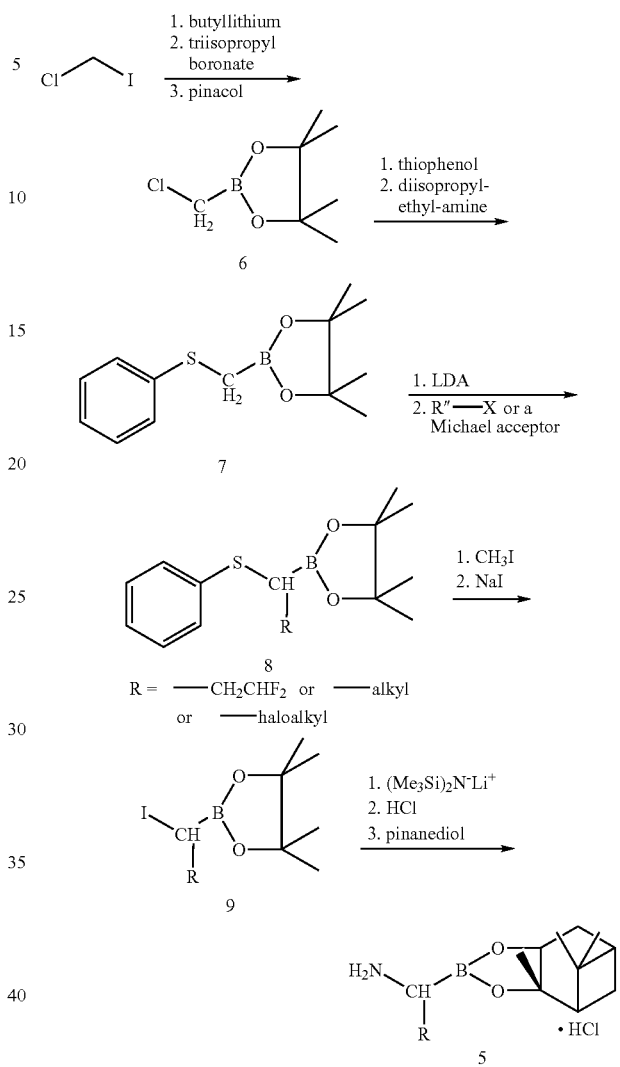

Scheme 8a

Scheme 8a outlines a method of preparing α-aminoboronic acids suitable for incorporation in to a peptide and applied as enzyme inhibitors. Matteson (Matteson and Majumdar *J. Organometallic Chem.* 170, 259–264, 1979; Matteson and Arne *Organometallics* 1, 280–288, 1982) discloses the preparation of α-haloboronic acids. Compound 6 is prepared by the method described by Sadhu and Matteson *Organometallics* 4, 1687–1689, 1985. Compound 6 is allowed to react with thiophenol in presence of tertiary base to give the thiol ether 7. Alternately, 7 can be prepared by reacting the lithium salt of thioanisole with a trialkyl boronate as described by Matteson and Arne *Organometallics* 1, 280–288 (1982). 7 is treated with LDA followed by a hydrocarbon containing an electrophilic center. For this reaction 1-bromo-2,2-difluoroethane was used to give a 2,2-difluoroethyl substituent 8. The α-aminoboronic acid 9 was obtained by treating 8 with methyl iodide or other suitable alkylating agent in the presence of iodide ion followed by lithium hexamethyldisilazane and HCl. In contrast to other procedures for preparing α-aminoboronic acids where the sidechain is introduced as a nucleophile or an alkene, the sidechain substituent is an electrophile. This provides a method of preparing 2-amino-3,3-difluoropropyl boronic acid where conventional methods have failed.

The chemistry outlined in Scheme 8a is readily applied by one skilled in the art to the synthesis of additional α-aminoboronic acids. After treatment of 7 with base to generate the anion at the α-position, a Michael acceptor can be added to synthesize additional more structurally diverse α-aminoboronic acids, for example, higher order alkyl halides which can be used to give more complex sidechains.

Scheme 8b illustrates the preparation of α-aminoboronic acids with hydroxy substituted side chains, boroSerine and boroThreonine. Both are synthesized as their benzyl protected form and incorporated into peptides. The benzyl protecting groups are removed by catalytic hydrogenation to give the final product. The synthesis of 2-benzyloxy-1-chloroethane boronic acids esters has been described (Matteson et al. *Organometallics* 3, 1284–1288, 1984). For H-boroSer(OBzl)-$C_{10}H_{16}$, the α-chloromethyl boronic acid is treated with the anion of benzyl alcohol to give the benzyl ether. Homologation with the anion of methylene chloride gives the α-chloro compound. It is readily converted to the α-aminoboronic acid by conventional procedures. Boro-threonine is prepared by a similar procedure except an α-chloroethyl boronic acid ester is prepared and converted to the benzyl protected alcohol. Homologation with $CHCl_2^-Li^+$ and treatment with $(Me_3Si)_2N^-Li^+$ and HCl gives H-boroThr(OBzl)—$C_{10}H_{16}$. The first series of reactions were conducted using the pinacol ester which resulted in the nonstereo specific introduction of the O-benzyl hydroxy group. This group can be introduced in the natural configuration R-configuation by using (S,S) dicyclohexaneethanediol as a chiral directing boronic acid protecting group.

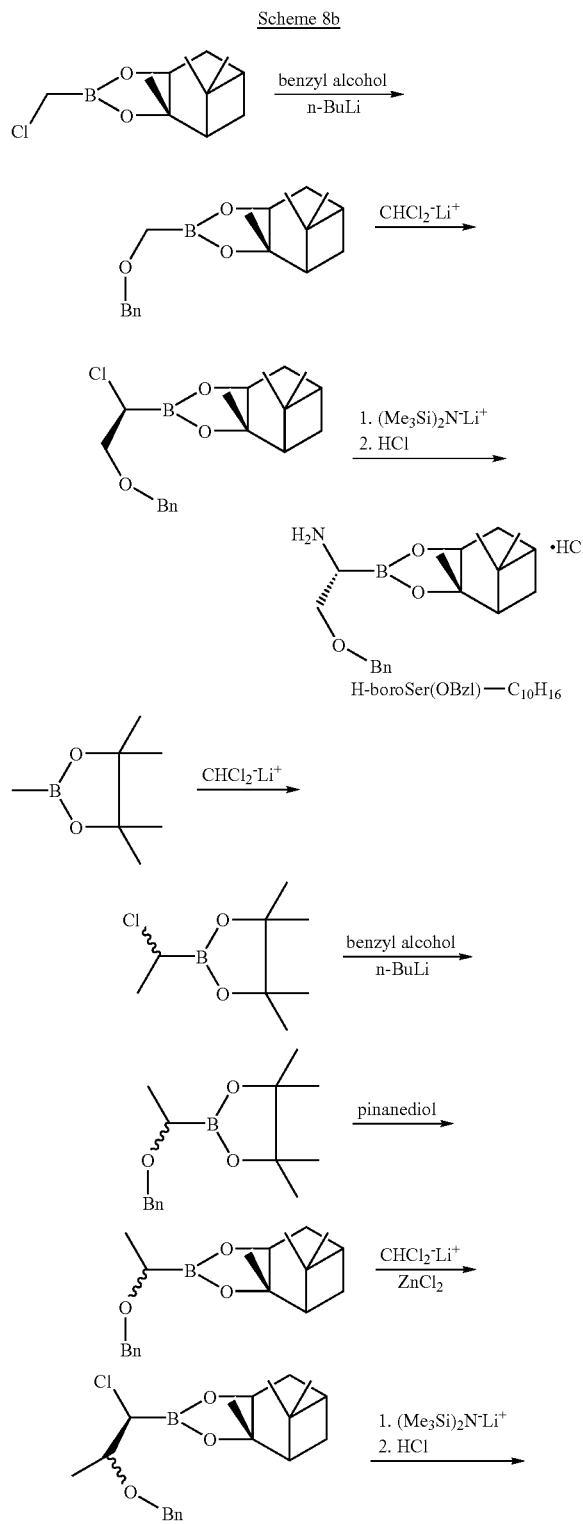

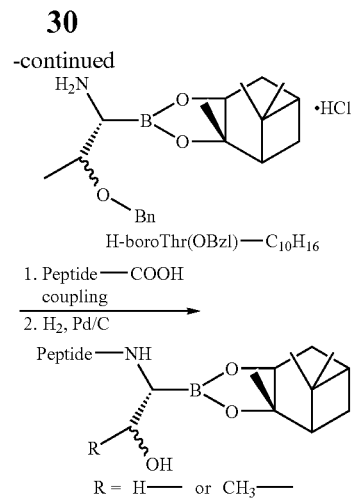

Scheme 8c describes the synthesis of boronic acid analogs of cysteine. Vinylmagnesium bromide is allowed to react with triethyl boronate to give vinylboronate diethyl ester. Transesterification with pinanediol gives the corresponding ester 16. Treatment of 16 with a sulfenyl chloride, for example phenyl sulfenyl chloride, gives the coresponding α-chloro-, α-thiol ether. The α-chloro group is readily converted to the amine using chemistry previously described (Scheme 8). Final deprotection of the thiol is achieved after incorporation of the amine in peptides. Additionally, the treatment of 16 with a thio sulfenyl chloride, for example phenyl thio sulfenyl chloride, followed by conversion to the amine using chemistry previously described (Scheme 8) gives the coresponding α-aminoboronic acid with a substituted disulfide side chain.

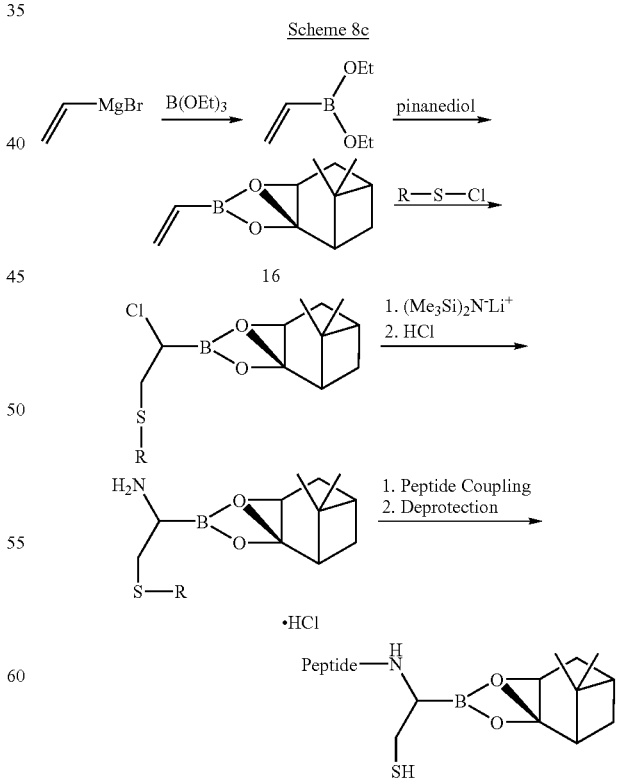

One diasteriomer of a compound of Formula (I) may display superior activity compared with the others. Thus, the following stereochemistries are considered to be a part of the present invention.

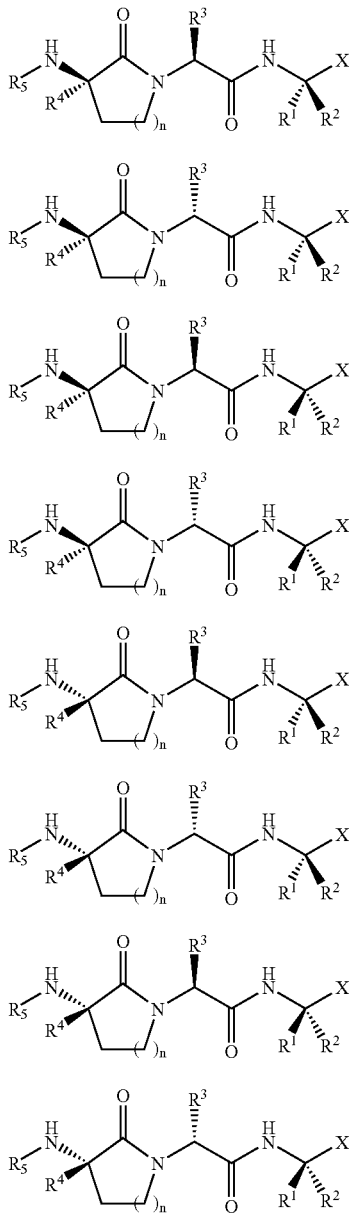

When required, separation of the racemic material can be achieved by HPLC using a chiral column or by a resolution using a resolving agent such as camphonic chloride as in Steven D. Young, et al, *Antimicrobial Agents and Chemotheraphy* 1995, 2602–2605. A chiral compound of Formula (I) may also be directly synthesized using a chiral catalyst or a chiral ligand, e.g., Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Abbreviations used in the examples are defined as follows: "1×" for once, "2×" for twice, "3×" for thrice, "° C." for degrees Celsius, "rt" for room temperature, "eq" for equivalent or equivalents, "g" for gram or grams, "mg" for milligram or milligrams, "mL" for milliliter or milliliters, "M" for molar, "mmol" for millimole or millimoles, "min" for minute or minutes, "h" for hour or hours, "MS" for mass spectrometry, "NMR" for nuclear magnetic resonance spectroscopy, "$^1$H" for proton, "HPLC" for high pressure liquid chromatography, "tlc" for thin layer chromatography, "v/v" for volume to volume ratio, "atm" for atmosphere, "α", "β", "R", and "S" are stereochemical designations familiar to one skilled in the art.

Example 1

(1R)-1-({(2S)-3-cyclohexyl-2-(3-isopropyl-3-({(2S)-3-methyl-2-((2-pyrazinylcarbonyl)amino)butanoyl}amino)-2-oxo-1-pyrrolidinyl)propanoyl}amino)-3-butenylboronic acid (+)-pinanediol ester (1a) A solution of Cbz-L-valine (4.88 g, 19.4 mmol), paraformaldehyde (0.84 g), and p-toluenesulfonic acid, (210 mg, 1.1 mmol) in benzene (160 mL) was refluxed for two h using a Dean-Stark apparatus. The solution was extracted with saturated sodium bicarbonate (2×) and brine, dried (MgSO$_4$), and concentrated under reduced pressure to give the desired oxazolidinone as a colorless oil (4.82 g, 94%). NMR ($^1$H, CDCl$_3$) δ 7.37 (s, 5H), 5.60 (br s, 1H), 5.20 (m, 3H), 4.23 (br s, 1H), 2.37 (br s, 1H), 1.08 (d, 3H, J=6.9), 1.01 (d, 3H, J=6.6).

(1b) A 0.5 M solution of potassium bis(trimethylsilyl) amide in tetrahydrofuran (44 mL, 22 mmol) was added over 20 min to a solution of the material from (1a) (4.82 g, 18.3 mmol) in tetrahydrofuran (75 mL) at −78° C. After 20 min, allyl bromide (3.2 mL, 37 mmol) was added dropwise, and the reaction was stirred at −78° C. for 2.5 h. The reaction was quenched with 10% potassium hydrogen sulfate (150 mL) and diluted with ethyl acetate (150 mL). The organic phase was extracted with 10% potassium hydrogen sulfate, saturated sodium bicarbonate, and brine, dried (Na$_2$SO$_4$), and concentrated under reduced pressure. The residue was purified by chromatography on silica gel (ethyl acetate/hexane, 10:90) to give a colorless oil (3.8 g, 68%). MS found (M+H)+=304.

(1c) A 1 M solution of sodium methoxide in methanol (3 mL, 3 mmol) was added to the material from (1b) (0.61 g, 2.0 mmol) in methanol (5 mL). The reaction was refluxed for 1 h, quenched with acetic acid (0.165 mL, 2.9 mmol), and concentrated under reduced pressure. The residue was dissolved in dichloromethane, extracted with saturated sodium bicarbonate, dried (Na$_2$SO$_4$), and concentrated under reduced pressure to yield a colorless oil (0.63 g, 100%). MS found: (M+H)$^+$=306.

(1d) Ozone was bubbled through a solution of the material from (1c) (0.593 g, 1.94 mmol) in methanol (20 mL) at −78° C. until a blue color persisted. Residual ozone was removed with a stream of oxygen. Dimethyl sulfide (0.6 mL, 8 mmol) was added, and the reaction mixture was allowed to warm to rt. After 2 h, the solution was concentrated under reduced pressure. The residue was dissolved in dichloromethane, extracted with water, dried (Na$_2$SO$_4$), and concentrated under reduced pressure to give a slightly yellow oil (0.65 g). The crude aldehyde was used without purification.

(1e) Sodium triacetoxyborohydride (0.649 g, 3.06 mmol) was added to a suspension of the material from (1d) (0.65 g, 1.9 mmol), L-cyclohexylalanine methyl ester hydrochloride (0.533 g, 2.4 mmol), and triethylamine (0.42 mL, 3.0 mmol)

in 1,2-dichloroethane (10 mL) at 0° C. The reaction was stirred overnight and allowed to warm to rt. The reaction was then refluxed for 5.5 h. The reaction mixture was diluted with dichloromethane and extracted with 1 M hydrochloric acid and saturated sodium bicarbonate. The organic phase was dried ($Na_2SO_4$) and concentrated under reduced pressure. The residue was purified by chromatography on silica gel (ethyl acetate/hexane, 1:3) to provide a 1:1 mixture of lactam diastereomers as a waxy solid (0.67 g, 78%). MS found: $(M+H)^+=445$, $(M+Na)^+=467$.

(1f) A solution of the material from (1e) (0.33 g, 0.74 mmol) in methanol (5 mL) was hydrogenated (1 atm, balloon) over 10% palladium on carbon (85 mg) for 2 h. The solution was filtered through Celite and concentrated under reduced pressure to provide the desired product (0.225 g, 98%). MS found: $(M+H)^+=311$, $(M+Na)^+=333$.

(1g) Hunig's base (0.17 mL, 1.0 mmol) was added to a solution of the material from (1f) (0.126 g, 0.407 mmol), N-(pyrazine-2-carbonyl)-L-valine (0.109 g, 0.488 mmol), and PyAOP (0.261 g, 0.50 mmol) (Carpino, et al. *J. Chem. Soc., Chem. Commun.* 1994, 201–203.) in dichloromethane at rt. After stirring overnight, the reaction was quenched with half saturated sodium carbonate (5 mL) and extracted with ethyl acetate. The organic phase was concentrated onto silica gel (500 mg) and purified by chromatography over silica gel (ethyl acetate/hexanes, 1:1) to give the desired product as a single diastereomer (74 mg, 35%). MS found: $(M+H)^+=516$, $(M+Na)^+=538$.

(1h) Lithium hydroxide monohydrate (10 mg, 0.24 mmol) was added to a solution of the material from (1g) (74 mg, 0.14 mmol) in a mixture of dimethoxyethane (1.5 mL) and water (1.0 mL) at 0° C. The reaction was stirred for 30 min and quenched with 1 M hydrochloric acid (0.5 mL). The solution was diluted with water (10 mL) and extracted with ethyl acetate (2×10 mL). The combined organic phases were washed with brine, dried ($Na_2SO_4$), and concentrated under reduced pressure to provide the desired prduct as a colorless oil (66 mg, 92%). MS found: $(M-H)^-=500$.

(1i) Isobutyl chloroformate (0.012 mL, 0.092 mmol) was added to a solution of the material from (1h) (41 mg, 0.082 mmol) and N-methyl morpholine (0.012 mL, 0.11 mmol) in tetrahydrofuran (1 mL) at −20° C. After 10 min, a solution of the (+)-pinanediol ester of L-boroallylglycine hydrochloride salt (35 mg, 0.12 mmol) in dichloromethane (1.5 mL) was added dropwise, followed by Hunig's base (0.042 mL, 0.24 mmol). The reaction was stirred for 1.5 h and allowed to warm to rt. The reaction mixture was concentrated under reduced pressure and the residue purified by chromatography on silica gel (ethyl acetate/hexane gradient, 1:4 to 4:1) to give the desired boronic ester as an amorphous solid (41 mg, 69%). MS found: $(M+Na)^+=755.5$.

Example 2

(1R)-1-({(2S)-3-cyclohexyl-2-(3-isopropyl-3-({(2S)-3-methyl-2-((2-pyrazinylcarbonyl)amino)butanoyl}amino)-2-oxo-1-piperidinyl)propanoyl}amino)-3-butenylboronic acid (+)-pinanediol ester (2a) A 0.5 M solution of 9-borabicyclo(3.3.1)nonane in tetrahydrofuran (9.9 mL, 5 mmol) was added to a solution of the material from (1b) (1.01 g, 3.34 mmol) in tetrahydrofuran (15 mL) at 0° C. The reaction was allowed to warm to rt and stir for 5 h before being quenched at 0° C with a solution of sodium acetate (3.4 g)and 30% hydrogen peroxide (4 mL) in water (20 mL). The reaction was diluted with ethyl acetate and extracted with brine. The organic phase was dried ($Na_2SO_4$) and concentrated under reduced pressure. The residue was purified by chromatography on silica gel (ethyl acetate/hexane 3:10) to provide the desired alcohol as a colorless oil (0.86 g, 80%). MS found: $(M+NH_4)^+=339$.

(2b) Dimethyl sulfoxide (0.60 mL, 7.8 mmol) was added dropwise to a solution of oxalyl chloride (0.342 mL, 3.9 mmol) in dichloromethane (15 mL) at −78° C. After 10 min, a solution of the material from (2a) (0.840 g, 2.62 mmol) in dichloromethane (5 mL) was added dropwise. After an additional 15 min, Hunig's base (2.2 mL, 13 mmol) was added dropwise. The reaction mixture was stirred 30 min at −78° C. and 3 h at 0° C. The reaction was quenched with water. The organic phase was washed with brine, dried ($Na_2SO_4$), and concentrated under reduced pressure to afford the crude aldehyde as a yellow oil (0.911 g). The material was used without further purification.

(2c) Following a procedure analogous to that used in the preparation of (1e), the aldehyde from (2b) (0.911 g, 2.6 mmol) was reacted with L-cyclohexylalanine methyl ester hydrochloride. Silica gel chromatography (ethyl acetate/hexane, 1:4) provided the desired product (1.05 g, 82%) as a 1:1 mixture of diastereomers. MS found: $(M+H)^+=489$.

(2d) A 1.2 M solution of sodium methoxide in methanol (0.60 mL, 0.72 mmol) was added to a solution of the material from (2c) (318 mg, 0.651 mmol) in methanol (6 mL). The reaction was stirred at rt for 8 h, quenched with acetic acid (0.045 mL, 0.79 mmol), and concentrated under reduced pressure. The residue was purified by silica gel chromatography (methanol/dichloromethane gradient, 1:20 to 1:5) to yield the desired lactam (111 mg, 37%) as a colorless solid.

(2e) Following a procedure analogous to that used in step (1f), the material from step (2d) (0.127 g, 0.278 mmol) was hydrogenated to yield the the crude product as a colorless oil (79.5 mg, 88%), which was used without further purification.

(2f) Following a procedure analogous to (1g), the material from (2e) (48 mg, 0.15 mmol) was coupled to N-(pyrazine-2-carbonyl)-L-valine with PyAOP and Hunig's base, providing the desired product as a single diastereomer (29 mg, 36%). MS found: $(M+Na)^+=552$.

(2g) Following a procedure analogous to (1h), the methyl ester from (2f) (29 mg, 0.054 mmol) was saponified with lithium hydroxide to provide the desired acid (29 mg, 100%). MS found: $(M-H)^-=514$.

(2h) Following a procedure analogous to (1i), the acid from step (2g) (28 mg, 0.054 mmol) was coupled to L-boroallylglycine hydrochloride salt using isobutylchloroformate. Silica gel chromatography (ethyl acetate/hexanes gradient, 1:4 to 4:1) of the crude material provided the desired boronic ester (5 mg, 12%) as an amorphous solid. MS found: $(M+Na)^+=769.5$.

Example 3

(1R)-1-(({3-((methylsulfonyl)amino)-2-oxohexahydro-1H-azepin-1-yl}acetyl)amino)propylboronic acid (+)-pinanediol ester (3a) Hunig's base (1.4 mL, 8.2 mmol) was added to a solution of N-Boc-D/L-allylglycine (0.645 g, 3.00 mmol), N-allylglycine ethyl ester (0.720 g, 5.0 mmol) (Gribble, G. W.; Hirth, B. H. *J. Heterocyclic Chem.* 1996, 33, 719–726.), and PyAOP (2.04 g, 3.91 mmol) in dimethylformamide (10 mL). After stirring 3 h at rt, the reaction mixture was quenched by addition of methanol and concentrated under reduced pressure. The residue was dissolved in ethyl acetate, extracted with saturated sodium bicarbonate and brine, dried ($Na_2SO_4$), and concentrated under reduced pressure. The residue was purified by silica gel chromatography (ethyl acetate/hexane, 1:3) to afford the desired dipeptide as a crystalline solid (0.887 g, 87%) MS found: $(M+Na)^+=363$.

(3b) Bis(tricyclohexylphosphine)dichlororuthenium benzylidene catalyst (21 mg, 0.025 mmol) was added to a refluxing solution of the dipeptide from (3a) (174 mg, 0.512 mmol) in dichloromethane (50 mL) under argon. After 3 h, the reaction mixture was cooled to rt and concentrated under reduced pressure. The residue was purified by silica gel chromatography (ethyl acetate/hexane, 1:4) to give the desired lactam (133 mg, 83%) as a crystalline solid. MS found: $(M+Na)^+=335$.

(3c) The material from (3b) (133 mg, 0.426 mmol) was hydrogenated using a procedure analogous to that of (1f), except that ethanol was employed as the solvent, giving the desired product (0.147 g), which was used without further purification. MS found: $(M+Na)^+=337$.

(3d) The material from (3c) (134 mg, 0.43 mmol) was saponified using a procedure analogous to that of (1h), except that tetrahydrofuran replaced dimethoxyethane as solvent, giving the desired acid as a colorless solid (0.121 g, 99%) MS found: $(M-H)^-=285$.

(3e) Hunig's base (0.212 mL, 1.24 mmol) was added dropwise to a solution of the acid from (3d) (117 mg, 0.410 mmol), L-boro-2-aminobutyric acid hydrochloride (114 mg, 0.417 mmol), and PyAOP (216 mg, 0.414 mmol) in dimethylformamide (2 mL). After 40 min, the reaction was diluted with ethyl acetate and extracted with 5% sodium bicarbonate and brine. The organic phase was dried ($Na_2SO_4$) and concentrated under reduced pressure. The residue was purified by silica gel chromatography (ethyl acetate/hexane, 4:1) to afford the desired boronic ester as an amorphous solid (0.155 g, 75%). MS found: $(M+Na)^{30}=528$.

(3f) A 4M solution of hydrochloric acid in dioxane (4 mL, 16 mmol) was added to the material from (3e) (141 mg, 0.28 mmol). The reaction was stirred for 2 h at rt and concentrated under reduced pressure to give the desired product as a colorless solid (133 mg), which was used without further purification. MS found: $(M+H)^+=406$.

(3g) Triethylamine (0.028 mL, 0.201 mmol) was added dropwise to a suspension of the material from (3f) (31 mg, 0.07 mmol) and methanesulfonyl chloride (0.010 mL, 0.135 mmol). After stirring for 18 h, the reaction was diluted with dichloromethane and extracted with 5% sodium bicarbonate. The organic phase was dried ($Na_2SO_4$) and concentrated under reduced pressure. The residue was purified by HPLC on a C18 reverse phase (acetonitrile/water gradient, 4:6 to 8:2) to afford the desired sulphonamide as an amorphous solid (18.5 mg, 56%). MS found: $(M+H)^+=484$.

Example 4

(1R)-1-{((2S)-2-(3-amino-3-isopropyl-2-oxo-1-pyrrolidinyl)-3-cyclohexylpropanoyl)amino}propylboronic acid (+)-pinanediol ester hydrochloride (4a) The 1:1 mixture of lactam diastereomers (6.5 g, 14 mmol) from (1e) was recrystallized from ethyl acetate/hexanes to give a single lactam diastereomer (1.9 g, 30%). $(\alpha)_D^{25}=-16.80°$ (C=0.280, methanol).

(4b) The lactam ester from (4a) (1.11 g, 2.5 mmol) was saponified using a procedure analogous to that of (1h), except that tetrahydrofuran replaced dimethoxyethane as solvent. The crude acid was obtained as a colorless foam (1.06 g, 100%) and was used in the next step without purification. MS found $(M+H)^+=431$.

(4c) The material from (4b) (1.06 g, 2.5 mmol) was coupled to L-boro-2-aminobutyric acid hydrochloride salt using a procedure analogous to (1i). The crude material was purified by silica gel chromatography (ethyl acetate/hexane, 1:1) to give the desired boronic ester (0.85 g, 52%). MS found $(M+H)^+=650$.

(4d) A solution of the boronic ester from (4c) (400 mg, 0.616 mmol) in a mixture of methanol (10 mL), 4M hydrochloric acid in dioxane (5 mL) and dioxane (30 mL) was hydrogenated (48 psi) over 10% palladium on carbon for 3 h at rt. The reaction mixture was filtered and concentrated under reduced pressure to afford the desired amine hydrochloride (340 mg, 100%). MS found: $(M+H)^+=516$.

Example 5

(1R)-1-(((2S)-2-{3-(((1,1'-biphenyl)-4-ylsulfonyl)amino)-3-isopropyl-2-oxo-1-pyrrolidinyl}-3-cyclohexylpropanoyl)-amino)-propylboronic acid (+)-pinanediol ester (5a) 4-Biphenylsulfonyl chloride (5 mg, 0.02 mmol) was added to a solution of the amine hydrochloride from (4d) (11 mg, 0.020 mmol), 4-dimethylamino pyridine (0.6 mg, 0.005 mmol), and triethylamine (0.012 mL, 0.086 mmol) in a mixture of 1,2-dichloroethane (0.2 mL) and ethyl acetate (0.1 mL). The reaction mixture was heated at 57° C. overnight and quenched by addition of water. The mixture was extracted with dichloromethane and the organic phase concentrated under reduced pressure. The residue was dissolved in acetonitrile, filtered, and purified by HPLC (acetonitrile/water gradient) to afford the desired sulfonamide (2 mg, 14%). MS found: $(M+H)^+=732$.

Example 6

(1R)-1-{(((2S)-3-cyclohexyl-2-(3-isopropyl-2-oxo-3-{((4-propylphenyl)sulfonyl)amino}-1-pyrrolidinyl)propanoyl)-amino}propylboronic acid (+)-pinanediol ester (6a) Using a procedure analogous to (5a) the amine hydrochloride from (4d) (11 mg, 0.020 mmol) was coupled to 4-propylphenylsulfonyl chloride to provide the desired sulfonamide (7 mg, 50%). MS found: $(M+H)^+=698.5$.

Example 7

(1R)-1-(((2S)-3-cyclohexyl-2-{3-isopropyl-3-((1-naphthylsulfonyl)amino)-2-oxo-1-pyrrolidinyl}-propanoyl)amino)propylboronic acid (+)-pinanediol ester (7a) Using a procedure analogous to (5a) the amine hydrochloride from (4d) (11 mg, 0.020 mmol) was coupled to 1-napthylsulfonyl chloride to provide the desired sulfonamide (3.3 mg, 23%). MS found: $(M+H)^+=706.5$.

Example 8

(1R)-1-(((2S)-2-{3-((anilinocarbonyl)amino)-3-isopropyl-2-oxo-1-pyrrolidinyl}-3-cyclohexylpropanoyl)-amino)propylboronic acid (+)-pinanediol ester (8a) Using a procedure analogous to (5a) the amine hydrochloride from (4d) (11 mg, 0.020 mmol) was coupled to phenylisocyanate to provide the desired sulfonamide (10 mg, 79%). MS found: $(M+H)^+=635.5$.

Example 9

(1R)-1-{((2S)-3-cyclohexyl-2-(3-isopropyl-3-{((3-methylphenyl)sulfonyl)amino}-2-oxo-1-pyrrolidinyl)propanoyl)amino}propylboronic acid (+)-pinanediol ester (9a) Using a procedure analogous to (5a) the amine hydrochloride from (4d) (11 mg, 0.020 mmol) was coupled to 3-methylphenylsulfonyl chloride to provide the desired sulfonamide (5.1 mg, 38%). MS found: $(M+H)^+=670.5$.

Example 10

(1R)-1-{((2S)-3-cyclohexyl-2-(3-isopropyl-3-{((3-methylphenyl)sulfonyl)amino}-2-oxo-1-pyrrolidinyl)propanoyl)amino}propylboronic acid (10a) Phenylboronic acid (40 mg, 0.32 mmol) was added to the boronic ester from (9a) (16 mg, 0.024 mmol) in a well-stirred mixture of dichloromethane (0.2 mL) and water (0.2 mL). The reaction mixture was stirred overnight. The organic layer was concentrated under reduced pressure and the residue purified by preparative tlc (chloroform/methanol, 9:1) to afford the desired boronic acid as a colorless solid (4 mg, 31%). MS found: $(M-H)^-=534$.

Example 11

(1R)-1-{((3-{((benzyloxy)carbonyl)amino}-3-isopropyl-2-oxo-1-pyrrolidinyl)(phenyl)acetyl)amino}propylboronic acid (+)-pinanediol ester (11a) Using a procedure analogous to (1e), the aldehyde from (1d) (0.45 g, 1.46 mmol) was reductively aminated with L-phenylglycine hydrochloride in the presence of sodium triacetoxy borohydride and triethylamine. Silica gel chromatography (ethyl acetate/hexane gradient, 1:9 to 3:2) afforded the desired product as a 1:1 mixture of diastereomers. MS found: $(M+H)^+=425$.

(11b) Using a procedure analogous to (11h), except that tetrahydrofuran replaced dimethoxyethane as solvent, the material from (11a) was saponified with lithium hydroxide. The acid (140 mg, 23% over two steps) was obtained and used in the subsequent step without purification.

(11c) Using a procedure analogous to (3e), the acid from (11b) (0.135 g, 0.33 mmol) was coupled to L-boro-2-aminobutyric acid hydrochloride in the presence of PyAOP and Hunig's base. Silica gel chromatography (ethyl acetate/hexane, 3:10), afforded the desired boronic ester as a 1:1 mixture of diastereomers (0.180 g, 90%). MS found: $(M+H)^+=630$ Example 12

(1R)-1-{((3-amino-3-isopropyl-2-oxo-1-pyrrolidinyl)(phenyl)acetyl)amino}propylboronic acid (+)-pinanediol ester hydrochloride (12a) The material from (11c) (0.185 g, 0.29 mmol) was hydrogenated (1 atm, balloon) in a mixture of concentrated hydrochloric acid (0.075 mL, 0.88 mmol) and methanol (10 mL) for 1 h at rt. The solution was filtered through Celite and concentrated under reduced pressure to give the desired amine hydrochloride (136 mg, 95%). MS found $(2M+H)^+=991$.

Example 13

(1R)-1-{({3-isopropyl-3-((methylsulfonyl)amino)-2-oxo-1-pyrrolidinyl}(phenyl)acetyl)amino}propylboronic acid (+)-pinanediol ester (13a) Using a procedure analogous to (5a), the amine hydrochloride from (12a) (20 mg, 0.038 mmol) was coupled to methane sulfonyl chloride. The crude product was purified by HPLC (acetonitrile:water gradient) to afford the desired product. MS found $(M+H)^+=574$.

Example 14

(1R)-1-{((3-isopropyl-2-oxo-3-{((4-propylphenyl)sulfonyl)-amino}-1-pyrrolidinyl)(phenyl)acetyl)amino}propylboronic acid (+)-pinanediol ester (14a) Using a procedure analogous to (5a), the amine hydrochloride from (12a) (30 mg, 0.056 mmol) was coupled to 4-propylphenylsulfonyl chloride. The crude product was purified by HPLC (acetonitrile:water gradient) to afford the desired product. MS found $(M+H)^+=678$.

Example 15

(1R)-1-{(((2S)-2-(3-{((benzyloxy)carbonyl)amino}-3-isopropyl-2-oxo-1-pyrrolidinyl)-4-methylpentanoyl)-amino}propylboronic acid (+)-pinanediol ester (15a) Using a procedure analogous to (1e), the aldehyde from (1d) (0.57 g, 1.85 mmol) was reductively aminated with L-leucine hydrochloride in the presence of sodium triacetoxy borohydride and triethylamine. Silica gel chromatography afforded the desired product (0.45 g, 61%) as a 1:1 mixture of diastereomers. MS found: $(M+H)^+=512$.

(15b) Using a procedure analogous to (1h), except that tetrahydrofuran replaced dimethoxyethane as solvent, the material from (15a) (0.45 g, 1.11 mmol) was saponified with lithium hydroxide. The acid (433 mg, quantitative) was obtained and used in the subsequent step without purification.

(15c) Using a procedure analogous to (3e), the acid from (15b) (0.080 g, 0.205 mmol) was coupled to L-boro-2-aminobutyric acid hydrochloride in the presence of PyAOP and Hunig's base. Silica gel chromatography (ethyl acetate/hexane, 1:1), afforded the desired boronic ester (120 mg, 95%) as a 1:1 mixture of diastereomers. MS found: $(M+H)^+=610$ Example 16

(1R)-1-{((2S)-2-(3-amino-3-isopropyl-2-oxo-1-pyrrolidinyl)-4-methylpentanoyl)amino}propylboronic acid (+)-pinanediol ester hydrochloride (16a) The material from (15c) (0.120 g, 0.2 mmol) was hydrogenated using a procedure analogous to (12a) to provide the desired amine hydrochloride (90 mg, 95%). MS found $(M+H)^+=476$.

Example 17

(1R)-1-(((2S)-2-{3-isopropyl-3-((methylsulfonyl)amino)-2-oxo-1-pyrrolidinyl}-4-methylpentanoyl)amino)propylboronic acid (+)-pinanediol ester (17a) Using a procedure analogous to (5a), the amine hydrochloride from (16a) (21 mg, 0.041 mmol) was coupled to methane sulfonyl chloride. The crude product was purified by HPLC (acetonitrile:water gradient) to afford the desired product. MS found (M+H)$^+$=554.

Example 18

(1R)-1-{((2S)-2-(3-isopropyl-2-oxo-3-{((4-propylphenyl)sulfonyl)amino}-1-pyrrolidinyl)-4-methylpentanoyl)amino}propylboronic acid (+)-pinanediol ester (18a) Using a procedure analogous to (5a), the amine hydrochloride from (16a) (20 mg, 0.039 mmol) was coupled to 4-propylphenylsulfonyl chloride. The crude product was purified by HPLC (acetonitrile:water gradient) to afford the desired product. MS found (M+H)$^+$=658.

Example 19

(1R)-1-({(2S)-3-cyclohexyl-2-(3-ethyl-3-({(2S)-3-methyl-2-((2-pyrazinylcarbonyl)amino)butanoyl}amino)-2-oxo-1-pyrrolidinyl)propanoyl}amino)-3-butenylboronic acid (+)-pinanediol ester (19a) Using a procedure analogous to (1a), Cbz-L-2-aminobutyric acid (5.54 g, 23.4 mmol) was reacted with paraformaldehyde. Silica gel chromatography (ethyl acetate/hexanes 1:3) afforded the oxazolidinone product (5.28 g, 91%).

(19b) Using a procedure analogous to (1b), the material from (19a) (5.28 g, 21.2 mmol) was alkylated with allyl bromide. Silica gel chromatography (ethyl acetate/hexane, 1:9) gave the product (3.49 g, 57%). MS found (M+NH$_4$)$^+$= 307.

(19c) Following a procedure analogous to (1c), the material from (19b) (1.72 g, 5.88 mmol) was reacted with sodium methoxide in methanol. Silica gel chromatography gave the desired product (1.7 g, 100%). MS found (M+H)$^+$=292.

(19d) The material from (19c) (1.7 g, 5.83 mmol) was treated with sodium periodate (3.74 g, 17.5 mmol) and a 2.5% solution of osmium tetroxide in t-butanol (0.6 mL) in a mixture of methanol (50 mL) and water (30 mL). When tic indicated complete consumption of starting material, the reaction was diluted with water and extracted with dichloromethane. The organic phase was dried (Na$_2$SO$_4$) and concentrated under reduced pressure. The residue was purified by silica gel chromatography (ethyl acetate/hexane, 1:4) to give the desired aldehyde (0.91 g, 53%). MS found (M+H)$^+$=294.

(19e) Following a procedure analogous to (1e), the aldehyde from (19d) (0.91 g, 3.1 mmol) was reductively aminated with cyclohexlyalanine methyl ester hydrochloride. The crude product was purified by silica gel chromatography to afford the desired lactam (1.0 g, 75%) as a 1:1 mixture of diastereomers. MS found (M+H)$^+$=431.

(19f) Following a procedure analogous to (1f), the lactam from (19e) (0.5 g, 1.16 mmol) was hydrogenated to afford the desired amine (0.31 g, 91%), which was used in the subsequent step without purification.

(19g) Following a procedure analogous to (1g), the amine from (19f) (0.21 g, 0.72 mmol) was coupled to N-(pyrazine-2-carbonyl)-L-valine. The crude product was purified by silica gel chromatography (ethyl acetate/hexane, 3:1) to afford the desired peptide lactam (0.35 g, 100%).

(19h) Following a procedure analogous to (1h), the material from (19g) (0.13 g, 0.26 mmol) was saponified with lithium hydroxide monohydrate to give the desired acid (0.107 g, 84%). MS found (M+H)$^+$=488.

(19i) Following a procedure analogous to (1i), the acid from (19h) (0.087 g, 0.18 mmol) was coupled to the (+)-pinanediol ester of L-boroallylglycine. The crude product was purified by silica gel chromatography to give the desired product as a 1:1 mixture of diastereomers. MS found (M+H)$^+$=719.

Example 20

(1R)-1-{((2S)-2-(3-{((benzyloxy)carbonyl)amino}-3-isopropyl-2-oxo-1-piperidinyl)-3-cyclohexylpropanoyl)-amino}propylboronic acid (+)-pinanediol ester (20a) Following a procedure analogous to (3e), the material from (2d) was coupled to L-boro-2-aminobutyric acid hydrochloride. The crude product was purified by silica gel chromatography to afford the desired boronic ester (0.034 g, 74%). MS found: (M+H)$^+$=665.

Example 21

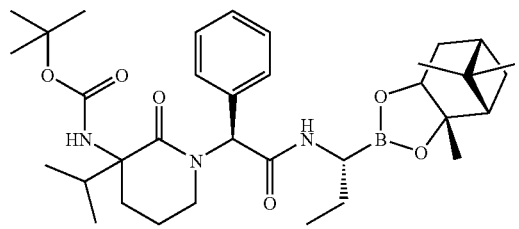

(1R)-1-{({3-((tert-butoxycarbonyl)amino)-3-isopropyl-2-oxo-1-piperidinyl}(phenyl)acetyl)amino}propylboronic acid (+)-pinanediol ester (21a) Using a procedure analogous to (1a), Boc-L-valine (22.4 g, 103 mmol) was treated with paraformaldehyde and p-toluenesulfonic acid in benzene. The desired oxazolidine was obtained as a colorless solid (14.3 g, 61%).

(21b) Using a procedure analogous to (1b), oxazolidinone (21a) (14.3 g, 62.4 mmol) was alkylated with allyl bromide. The desired allylated oxazolidinone was obtained as a yellow oil (15.45 g, 92%). MS found (M+Na)+=292.

(21c) A solution of 2N sodium hydroxide (10 mL) was added to oxazolidinone (21b) (2.70 g, 10 mol) in methanol (10 mL). The reaction mixture was warmed to 50° C. for 5 h and then quenched with 1N hydrochloric acid (20 mL). The mixture was extracted with ethyl acetate (3×), dried (MgSO$_4$), and concentrated under reduced pressure. The desired acid was obtained as a yellow oil (2.6 g, 100%). MS found (M−H)−=256.

(21d) A solution of acid (21c) (2.19 g, 8.51 mmol) and benzyl bromide (0.962 mL) in acetone (50 mL) was heated to reflux in the presence of potassium carbonate (1.8 g). After 3.5 h, the reaction mixture was concentrated, resuspended in hexane, and filtered through Celite. This solution was concentrated and the residue was purified by chromatography on silica gel to afford the desired ester (2.44 g, 82%) as a colorless oil. MS found (M+Na)+=370.

(21e) Using a procedure analogous to (2a), ester (21d) (2.44 g, 7.02 mmol) was hydroborated with 9-borabicyclo (3.3.1)nonane and oxidized to afford the desired alcohol (1.84 g, 72%) after chromatography on silica gel. MS found (M+Na)+=388.

(21f) Using a procedure analogous to (2b), alcohol (21e) (1.84 g, 5.03 mmol) was added to the reagent generated by addition of dimethyl sulfoxide to oxalyl chloride in dichloromethane at −78° C. After aqueous workup, the desired aldehyde was obtained (1.99 g) and used without further purification. (M+Na)+=386.

(21g) Using a procedure analogous to (1e), the aldehyde from (21f) (0.679 g, 1.8 mmol) was reacted with L-phenylglycine methyl ester hydrochloride. Silica gel chromatography (5% acetone/toluene) afforded the desired amine as a 1:1 mixture of diastereomers (0.55 g, 62%). (M+H)+=513.

(21h) A solution of amine (21g) (389 mg, 0.76 mmol) in ethanol (10 mL) was hydrogenated over 10% palladium on carbon (43 mg) for 40 min. The solution was filtered through Celite and concentrated under reduced pressure to afford the desired acid as a white solid (315 mg, 98%). (M+H)+=423.

(21i) A solution of acid (21h) (315 mg, 0.745 mmol) and HOAt (104 mg, 0.76 mmol) in dichloromethane (10 mL) at 0° C. was treated with EDCI (157 mg, 0.82 mmol). After 20 min, the reaction mixture was warmed to room temperature and stirred for 30 min. The reaction was diluted with dichloromethane and washed with 1N hydrochloric acid. The organic layer was dried (Na$_2$SO$_4$) and concentrated under reduced pressure. Chromatography on silica gel (20–30% ethyl acetate/hexane) afforded the desired lactam (0.32 g, 95%) as a 1:1 mixture of diastereomers. (M+H)+= 405.

(21j) Following a procedure analogous to (1h), except that tetrahydrofuran replaced dimethoxyethane as solvent, the material from (21i) (0.200 g, 0.494 mmol) was saponified with lithium hydroxide to afford the desired acid (180 mg, 93%). (2M−H)−=779.

(21k) Using a procedure analogous to (3e), the acid from (21j) (180 mg, 0.46 mmol) was coupled to L-boro-2-aminobutyric acid hydrochloride salt. Chromatography on silica gel and HPLC afforded the desired boronic ester (99 mg, 35%). (M+H)+=610.

Example 22

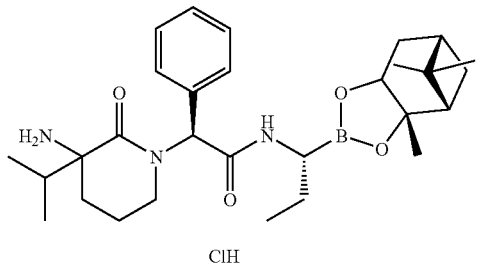

(1R)-1-{((3-amino-3-isopropyl-2-oxo-1-piperidinyl)(phenyl)acetyl)amino}propylboronic acid hydrochloride (+)-pinanediol ester (22a) The material from procedure (21k) (99 mg, 0.16 mmol) was treated with 4M hydrogen chloride solution in 1,4-dioxane (2 mL) for 5.5 h. The reaction mixture was concentrated to afford the desired amine (82 mg, 94%). (M+H)+=510.

Example 23

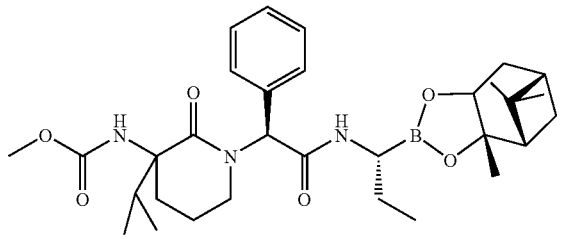

(1R)-1-{({3-isopropyl-3-((methoxycarbonyl)amino)-2-oxo-1-piperidinyl}(phenyl)acetyl)amino}propylboronic acid (+)-pinanediol ester (23a) Using a procedure analogous to (5a), the amine hydrochloride from (22a) (7 mg, 0.013 mmol) was reacted with methyl chloroformate. After purification by HPLC, the desired product was obtained (2.6 mg, 36%). (M+H)+=568.

Example 24

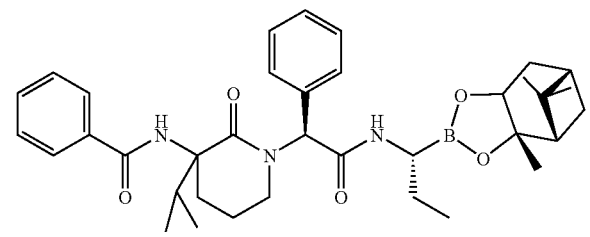

(1R)-1-{((3-(benzoylamino)-3-isopropyl-2-oxo-1-piperidinyl)(phenyl)acetyl)amino}propylboronic acid (+)-pinanediol ester (24a) Using a procedure analogous to (5a), the amine hydrochloride from (22a) (7 mg, 0.013 mmol) was reacted with benzoyl chloride. After purification by HPLC, the desired product was obtained (3.9 mg, 49%). (M+H)+=614.

Example 25

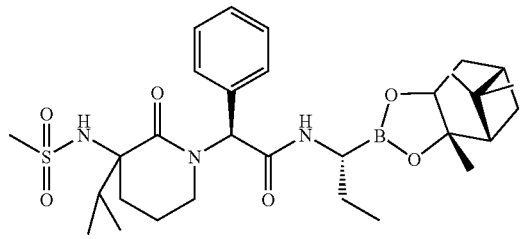

(1R)-1-{({3-isopropyl-3-((methylsulfonyl)amino)-2-oxo-1-piperidinyl}(phenyl)acetyl)amino}propylboronic acid (+)-pinanediol ester (25a) Using a procedure analogous to (5a), the amine hydrochloride from (22a) (7 mg, 0.013 mmol) was reacted with methanesulfonyl chloride. After purification by HPLC, the desired product was obtained (2.2 mg, 29%). (M+H)+= 588.

Example 26

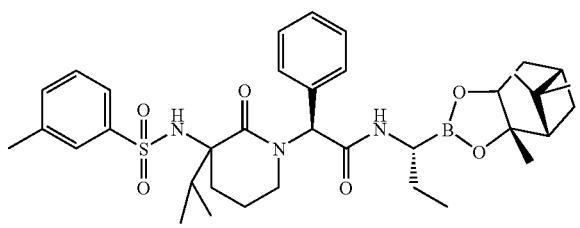

(1R)-1-{((3-isopropyl-3-{((3-methylphenyl)sulfonyl)amino}-2-oxo-1-piperidinyl)(phenyl)acetyl)amino}propylboronic acid (+)-pinanediol ester (26a) Using a procedure analogous to (5a), the amine hydrochloride from (22a) (7 mg, 0.013 mmol) was reacted with 3-methylbenzenesulfonyl chloride. After purification by HPLC, the desired product was obtained (2.7 mg, 31%). (M+H)+=664.

TABLE 1

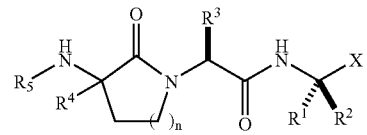

In Table 1, $R^2$ = H and X = $BO_2C_{10}H_{16}$ (pinanediol ester) for all entries except 10, for which X = $B(OH)_2$.

| Ex # | $R^1$ | $R^3$ | $R^4$ | $R^5$ | n | MS |
|---|---|---|---|---|---|---|
| 1 | allyl | Cyclohexyl-methyl | i-propyl | N-(pyrazine-2-Carbonyl)-L-valyl | 1 | 755.5 (M + Na)+ |
| 2 | allyl | Cyclohexyl-methyl | i-propyl | N-(pyrazine-2-Carbonyl)-L-valyl | 2 | 769.5 (M + Na)+ |
| 3 | ethyl | H | H | Methanesulfonyl | 3 | 484 (M + H)+ |
| 4 | ethyl | Cyclohexyl-methyl | i-propyl | H | 1 | 516 (M + H)+ |
| 5 | ethyl | Cyclohexyl-methyl | i-propyl | 4-biphenyl-sulfonyl | 1 | 732 (M + H)+ |
| 6 | ethyl | Cyclohexyl-methyl | i-propyl | 4-propylphenyl-sulfonyl | 1 | 698.5 (M + H)+ |
| 7 | ethyl | Cyclohexyl-methyl | i-propyl | 1-napthyl-sulfonyl | 1 | 706.5 (M + H)+ |
| 8 | ethyl | Cyclohexyl-methyl | i-propyl | N-Phenylcarbamoyl | 1 | 635.5 (M + H)+ |
| 9 | ethyl | Cyclohexyl-methyl | i-propyl | 3-methylphenyl-sulfonyl | 1 | 670.5 (M + H)+ |
| 10 | ethyl | Cyclohexyl-methyl | i-propyl | 3-methylphenyl-sulfonyl | 1 | 534 (M − H)− |
| 11 | ethyl | phenyl | i-propyl | Carbobenzyloxy- | 1 | 630 (M + H)+ |
| 12 | ethyl | phenyl | i-propyl | H | 1 | 991 (2M + H)+ |
| 13 | ethyl | phenyl | i-propyl | Methanesulfonyl | 1 | 574 (M + H)+ |
| 14 | ethyl | phenyl | i-propyl | 4-propylphenyl-sulfonyl | 1 | 678 (M + H)+ |
| 15 | ethyl | i-butyl | i-propyl | Carbobenzyloxy | 1 | 610 (M + H)+ |
| 16 | ethyl | i-butyl | i-propyl | H | 1 | 476 (M + H)+ |
| 17 | ethyl | i-butyl | i-propyl | Methanesulfonyl | 1 | 554 (M + H)+ |
| 18 | ethyl | i-butyl | i-propyl | 4-propylphenyl-sulfonyl | 1 | 658 (M + H)+ |
| 19 | allyl | Cyclohexyl-methyl | ethyl | N-(pyrazine-2-Carbonyl)-L-valyl | 1 | 719 (M + H)+ |
| 20 | ethyl | Cyclohexyl-methyl | i-propyl | Carbobenzyloxy | 2 | 665 (M + H)+ |

Preparation of α-aminoboronic Acids
Preparation of H-boroAlg-pinanediol·HCl (R=allyl)
Formula:

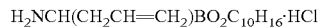

2-Propene boronate pinanediol ester. Ether (300 mL) was placed in a 5 L, 4 neck flask equipped with two addition funnels, thermometer and a mechanical stirrer. Triisopropyl borate (Aldrich) (1 mol) in 600 mL of anhydrous ether and allylmagnesium bromide in ether (Aldrich) (1.0 mol, 1.0 L, 1.0 M) were added simultaneously to 300 mL of dry ether at −78° C. over a period of 2.5 hours. The mixture was warmed to room temperature and stirred for 12 h. The slurry was recooled to 0° C., followed by dropwise addition of 40% sulfuric acid (2 mol) over a 1 hour period. The mixture was warmed to room temperature and was allowed to stir for 2 hours. The organic layer was separated and (+)-pinanediol (1.0 mol) was added. After 12 h, the solution was dried over sodium sulfate and filtered. The filtrate was concentrated in vacuo and distilled (bp 85–87° C., 1 mm Hg) to give 118 g (53%) of product as a clear, semi-viscous liquid: $^1$H-NMR (CDCl$_3$) δ 5.8–6.0 (m, 1H), 4.9–5.1 (m, 2H), 4.2 (dd, 1H), 2.8 (m, 2H), 2.05–1.78 (m, 6H), 1.38 (s, 3H), 1.27 (s, 3H), 0.83 (s, 3H).

1-Chloro-3-butene boronate pinanediol ester. The α-chloro compound was prepared by homologation of the corresponding allyl boronate. To a 5-liter flask equipped with two addition funnels, thermometer and a mechanical stirrer, was added the allyl boronate (117, 0.53 mol) dissolved in dry THF (1 L), followed by the addition of cylclohexane (0.5 L) and dichloromethane (0.71 mol). The solution was cooled to −78° C., followed by dropwise addition of lithium diisopropylamide (LDA) in heptane/THF/ethylbenzene (0.64 mol, 2.0 M, Aldrich catalog number 36,179-8) over a 1 hour period, taking care that a reaction temperature between −60 to −78° C. was maintained. Anhydrous zinc chloride in ether (0.86 mol, 1.0 M) was added. The reaction was warmed to room temperature and stirred for 12 hours. Hexane (600 mL) was added and the mixture was stirred for 1 hour. Cold 1 N H$_2$SO$_4$ (3.2 L) was added and the phases were separated. The aqueous layer was washed with hexane (600 mL). The combined organic phases were concentrated to 1 L and washed with 5% sodium bicarbonate (1 L) and saturated sodium chloride (1 L). They were dried over sodium sulfate and filtered. The filtrate was concentrated in vacuo and distilled (bp 130–132° C., 0.5 mm Hg) to give 60 g (42%) of the α-chloroboronic acid as a clear yellow oil. $^1$H-NMR (CDCl$_3$) δ 5.8–6.0 (m, 1H), 5.2 (m, 2H), 4.2 (dd, 1H), 3.48 (q, 1H) 2.8 (m, 2H), 2.05–1.78 (m, 6H), 1.41 (s, 3H), 1.29 (s, 3H), 0.84 (s, 3H).

H-boroAlg pinanediol ester•hydrochloride. The bis-trimethylsilane protected amine (Scheme 8) was prepared by dissolving hexamethyldisilizane (64.4 mmol) in dry THF (30 mL) and cooling to −78° C. n-Butyl lithium in hexane (1.6 N, 70.8 mmol) was added and the solution was allowed to warm to room temperature. It was recooled to −78° C. and 1-chloro-3-butene boronate pinanediol (17.2 g, 64.4 mmol) was added in 30 mL THF. The mixture was allowed to slowly warm to room temperature and to stir overnight. Solvent was removed by evaporation and dry hexane (200 mL) was added. Insoluble material was removed by filtration under a nitrogen atmosphere through a bed of celite to yield a solution of the protected amine. This solution was cooled to −78° C. and 4 N anhydrous hydrogen chloride in dioxane (192 mmol) was added. The reaction was slowly allowed to warm to room temperature and to stir overnight. The solvent was evaporated under vacuum to yield a brown oil. It was purified on a 5×90 cm column of Sephadex™ LH-20 in methanol. TLC in ethyl acetate:hexane (1:1) indicated the product as a single base spot which gave a positive test for amines after spraying with ninhydrin. The product eluted in fractions 51–70 (10 mL fractions). The fractions were pooled, concentrated, and dried under vacuum to give 16 g (87.2%) of the desired product as a foam. $^1$H-NMR (CDCl$_3$) δ 8.21 (bs, 2H), 5.80–6.0 (m, 1H), 5.20 (m, 2H), 4.2 (dd, 1H), 3.0 (m, 1H), 2.62 (m, 2H), 2.4–1.78 (m, 6H), 1.41 (s, 3H), 1.29 (s, 3H), 0.80 (s, 3H).

Preparation of boroAbu-pinanediol ester (R=ethyl)
Formula:

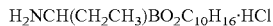

Propane boronate pinanediol ester. The alkyl boronate was prepared on a 0.50 mole scale using a procedure similar to the one used in the preparation of allyl boronate pinanediol. The crude product was distilled (bp 63° C., 2 mm Hg) to give 32.3 g (41.4%) as a clear oil. $^1$H-NMR (CDCl$_3$) δ 4.23 (dd, 1H), 2.40–1.78 (m, 6H), 1.38 (s, 3H), 1.28 (s, 3H), 0.97 (t, 3H), 0.83 (s, 3H), 0.79 (q, 2H).

1-Chloropropane boronate pinanediol ester. The α-chloro boronic acid was prepared on a 0.21 mole scale by the procedure described for H-boroAlg-pinanediol except the reaction mixture was washed with saturated aqueous ammonium chloride (1000 mL) rather than sulfuric acid. Phases were separated and the aqueous layer was washed with an equal volume of hexane. The organic phases were combined, dried over anhydrous sodium sulfate, filtered and concentrated to give a crude product which was distilled (bp 100–102° C., 0.6 mm Hg) to yield 28.8 g (54.4%) of the desired product as a clear yellow oil. $^1$H-NMR (CDCl$_3$) δ 4.35 (dd, 1H), 3.41 (m, 1H), 2.40–1.80 (m, 8H), 1.41 (s, 3H), 1.29 (s, 3H), 1.02 (t, 3H), 0.84 (s, 3H).

H-boroAbu pinanediol ester•ehydrochloride. The amino boronic acid was prepared on a 0.09 mole scale and was purified by a procedure similar to the one described for Example 1 to yield 23 g of crude product. A proportion of this material (13 g) was purified by chromatography on an LH-20 column to give 7.47 g (54.9%) of the desired product as a brown foam. $^1$H-NMR (CDCl$_3$) δ 8.24 (s, 3H), 4.36 (dd, 1H), 2.91 (m, 1H), 1.8–2.4 (m, 8H), 1.41 (s, 3H), 1.27 (s, 3H), 1.08 (t, 3H), 0.82 (s, 3H).

Preparation of boro-yclopropylglycine pinacol ester (R=cyclopropyl)
Formula:

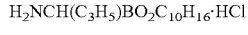

Cyclopropylboronate pinacol ester. The pinacol cyclopropyl bornate ester was prepared by the addition of cyclopropyl magnesium bromide was added to isopropylboronate pinacol ester. The latter compound was prepared by a previously described procedure (Andersen, M. W.; Hildebrandt, B.; Koster, G.; Hoffmann, R. W. Chem. Ber. 122, 1989, 1777–1782). The Grignard reagent was prepared by adding cyclopropylbromide (3.0 mL, 37 mmol) to magnesium turnings (11 g, 0.46 mole) in THF (300 mL) at room temperature under nitrogen. The solution was carefully warmed to 42° C. at which point a vigorous exotherm ensued. After the exotherm had subsided an additional 3 mL of cyclopropylbromide was added and an exotherm ensued and subsided. This iterative process was repeated until all of the cyclopropyl bromide was added (36 mL, 0.45 mole). The solution was heated at 50° C. for an additional 2 h. At this time the contents of the flask were transferred to an addition funnel and added to a solution of isopropylboronate pinacol ester (84 g, 0.45 mol) in ether (400 mL) in a 3-necked, 2-liter flask in ether (500 mL) at −78° C. under nitrogen. The cyclopropyl Grignard reagent was added dropwise over a period of 3 h. The solution was allowed to warm to room temperature and stirred overnight. The solution was cooled to 0° C. and 1 N HCl prepared in saturated aqueous NaCl (500 mL) was added dropwise over a period of 1 h. The solution was allowed to stir for an additional 4 h and the layers were separated. The aqueous layer was extracted with hexanes (3×300 mL), dried over MgSO$_4$, and concentrated using a rotary evaporator. The residue was purified by silica gel chromatography using 10% ethyl acetate: hexanes as a solvent to yield a clear colorless oil (42 g, 0.25 mole, 56%), bp 50–52° C., 8 mm Hg. $^1$H NMR d 0.36–0.50 (m, 5H), 1.18 (s, 12H).

1-Chloro-1-cyclopropylmethyl boronate pinacol ester. A 3-necked 250 mL flask containing THF (75 mL) and dichloromethane (2.5 mL, 39 mmol) was cooled to −100° C. n-Butyllithium (1.6 M in Hexanes, 24 mL, 39 mmol) was added cautiously to maintain a solution temperature of −100° C. After stirring at −100° C. for 45 min, a solution of cyclopropylboronate pinacol ester (6.0 g, 36 mmol) in THF (10 mL) precooled to −78° C. was added. The solution was allowed to warm to room temperature and stirred for an additional 12 h. The solution was concentrated by evaporation and hexanes were added to give a solid. The mixture was filtered and the filtrate was evaporated to give an oil. This material was distilled through a short path distillation apparatus (67–70° C., 0.2 mm Hg) to yield a clear colorless oil (5.5 g, 58% yield). $^1$H-NMR d (CDCl$_3$) 2.87 (d, 2H), 1.27 (s, 12H), 0.63 (m, 3H), 0.37 (m, 2H).

H-boroCyclopropylglycine pinanediol ester. The α-chloro compound (5.0 g, 23 mmol) was dissolved in THF (50 mL) and added to a freshly prepared solution of lithium bis-trimethylsilylamide (100 mL of a 3.2 M solution) at −78° C. under nitrogen. The solution was warmed to room temperature and stirred for 18 h. THF was removed by rotary evaporation and hexanes were added to the oil to give a precipitate. The solid was removed by filtration and the filtrate was cooled to −78° C. A solution of 4 N HCl in dioxane (17 mL, 69 mmol, 3 equivalents) was added and the solution was stirred for 4 h while warming to room temperature to give a solid. It was isolated by filtration and dissolved in hot CHCl$_3$ (150 mL). Following concentration to 10 mL, hot ethyl acetate (~25 mL) was added. Slow crystallization gave the desired product (3.3 g, 14 mmol, 60% yield). $^1$H NMR (CDCl$_3$) 8.22 (br. s, 3H), 3.47 (m, 1H), 1.28 (s, 12H), 0.65 (m, 4H), 0.38 (m, 1H).

Preparation of H-borodifluoroethylglycine pinanediol (R=2, 2-difluoroethyl)
Formula:

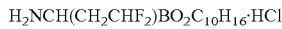

Chloromethyl boronate pinacol ester. Tetrahydrofuran (150 mL) was placed in a 1 L, 3 neck flask equipped with two addition funnels. Triisopropyl borate (Aldrich) (32.1 mL, 139 mmol) and chloro-iodomethane (Aldrich) (10.3 mL, 142 mmol) were added to the flask. The reaction mixture was cooled to −78° C. n-Butyllithium (81.9 mL, 131 mmol, 1.6 M in hexanes) was added dropwise to the flask via an addition funnel. The solution was stirred at −78° C. for 2 hours and then gradually warmed to −10° C. A crystal of methyl orange was added to the reaction. Hydrogen chloride (1.0 N in ether) was added via the other addition funnel until the methyl orange end point was reached. Pinacol (16.4 g, 139 mmol) was added to the flask and the reaction mixture was stirred for 12 hours. It was then concentrated in vacuo and distilled (bp 61–63° C., 5 mm Hg) to give 16.0 g (65%) of the desired compound as a yellow oil. $^1$H NMR (CDCl$_3$) δ 2.97 (s, 2H, ClCH$_2$B), 1.29 (s, 12H, CCH$_3$).

Iodomethyl boronate pinacol. THF (800 mL) was placed in a 3 L, 3-necked flask equipped with two addition funnels. Triisopropyl boronate (Aldrich) (128 mL, 0.55 mol) and chloro-iodomethane (Aldrich) (100 g, 0.56 mol) were added. The mixture was cooled to −78° C. and n butyl lithium (330 mL, 0.53 mol, 1.6 M in hexanes) was added dropwise. The solution was stirred for 2 h and slowly allowed to warm to −10° C. Methyl orange indicator was added and HCl (1.0 M in ether) was added until the methyl orange endpoint was reached. Pinacol (65 g, 0.55 mol) was added and reaction mixture was allowed to stir 12 h. It was filtered and evaporated in vacuo. The residue was dissolved in acetone (500 mL) and sodium iodide (70 g, 0.47 mol) was added. After stirring for 12 h at room temperature, solvent was removed by evaporation and the residue was dissolved in ethyl acetate and washed with saturated aqueous NaCl. The organic phase was dried over Na$_2$SO$_4$, filtered, and concentrated in vacuo. It was distilled to give 69 g (47%) of the desired product (bp 45–50° C., 1.5 mm). $^1$H NMR (CDCl$_3$) δ 2.16 (s, 2H), 1.26 (s, 12H).

Phenylthiomethane boronate pinacol ester. Thiophenol (11.6 mL, 113 mmol) was dissolved in DMF (40 mL) and diisopropylethylamine (19.8 mL, 113 mmol) and chloromethyl boronate pinacol ester (20 g, 113 mmol) were added sequentially. (Iodomethyl boronate pinacol can be readily substituted for the chloro compound.) After stirring for 12 hours, solvent was removed by rotary evaporation and ether (70 mL) was added. The reaction mixture was washed with 0.2 N HCl (70 mL), 5% NaHCO$_3$ (70 mL) and saturated sodium chloride (70 mL). The combined organic phases were dried over sodium sulfate and filtered. The filtrate was concentrated in vacuo and distilled (bp 125–127° C., 0.6 mm Hg) to give 21.6 g (76%) of the desired product as a clear oil. $^1$H NMR (CDCl$_3$) δ 7.32–7.11 (m, 5H), 2.42 (s, 2H), 1.24 (s, 12H).

1-Phenylthio-3,3-difluoropropane-1-boronate pinacol ester. Butyllithium (50.6 mL, 126 mmol, 2.5 M in hexanes) was added dropwise to a solution of diisopropylamine (18.4 mL, 133 mmol) dissolved in THF (40 mL) at 0° C. in a 500 mL round bottom flask. A solution of phenylthiomethane boronate pinacol ester (31.6 g, 126 mmol) in THF (40 mL) was added dropwise over a period of approximately 2 min to yield a white precipitate. After stirring for 1 hour at 0° C., 1,1-difluoro-2-bromoethane (Lancaster) (51 mL, 630 mmol) was added dropwise. The precipitate dissolved and the solution was allowed to warm to room temperature and stirred for 16 hours. Excess cold 10% phosphoric acid was added and the mixture was stirred for 5 min. Ether (100 mL) was added and the phases were separated. The organic layer was dried over sodium sulfate and filtered. The filtrate was concentrated in vacuo and distilled (bp 119–122° C., 0.4 mm Hg) to give 22 g (56%) of product as a clear oil. $^1$H NMR (CDCl$_3$) δ 7.43–7.19 (m, 5H, C$_6$H$_5$), 6.16–5.78 (tt, 1H, CHF$_2$), 2.82 (m, 1H, SCHB), 2.38–2.19 (m, 2H, CH$_2$CHF$_2$), 1.23 (s, 12H, CCH$_3$). $^{19}$F NMR δ −116.8 to −117.0 (dt, CHF$_2$).

1-Iodo-3,3-difluoropropane-1-boronate pinacol ester. 1-Phenylthio-3,3-difluoropropane-1-boronate pinacol ester (6.00 g, 19.1 mmol) was dissolved in anhydrous acetonitrile (60 mL) and dry methyl iodide (24 mL, 380 mmol) and sodium iodide (5.76 g, 38.2 mmol) were added. The reaction mixture was vigorously refluxed for 5 h. The solvent was evaporated in vacuo. The residue was partitioned between water (40 mL) and ether (40 mL). The phases were separated and the organic phase was washed with an equal volume of ether. The combined organic phases were dried over Na₂SO₄ and evaporated to give a brown oil which was purified by distillation to give 3.1 g (49%), bp 63–65° C., 0.4 mm. ¹H NMR (CDCl₃) δ 6.18–5.79 (tt, 1H, CHF₂), 3.21 (t, 1H, ICHB), 2.43–2.21 (m, 2H, CH₂CHF₂), 1.27 (s, 12H, CCH₃).

1-Amino-3,3-difluoropropyl boronate pinacol·HCl. 1-Iodo-3,3-difluoropropanyl boronate pinacol (2.7 g, 8.1 mmol) was dissolved in THF (10 mL) and was added dropwise to a solution of lithium bis(trimethylsilyl)amide (9.68 mL, 9.68 mmol, 1.0 M in THF) dissolved in anhydrous THF (10 mL) and cooled to −78° C. The reaction mixture was allowed to warm to room temperature and stirred for 12 h. It was concentrated in vacuo and hexane was added. The reaction mixture was cooled to −78° C., followed by the dropwise addition of 4 N anhydrous hydrogen chloride in dioxane (6.05 mL, 24.2 mmol). The mixture was allowed to warm to room temperature and stirred for 5 hours. The reaction mixture was evaporated and chloroform was added. Insoluble material was removed by filtration. The filtrate was evaporated almost to dryness and hexanes were added. Upon standing the product crystallized. It was isolated and washed with cold hexane to yield 1.1 g (52%), mp 138–141° C. ¹H NMR (CDCl₃) δ 7.68 (bs, 3H), 6.22–6.01 (tt, 1H), 3.42 (m, 1H), 2.76–2.51 (m, 2H), 1.32 (s, 12H). ¹⁹F NMR δ −115.2 to −115.5 (dt, CHF₂). HRMS calculated for C₉H₁₈B₁O₂F₂N+H: 222.1. Found: 222.1.

Preparation of boroVinylglycine pinanediol
Formula:

H₂NCH(CH=CH₂)BO₂C₁₀H₁₆·HCl

1-Chloro-1-vinylmethyl boronate pinanediol. The α-chlorovinyl compound was prepared by the method described by Matteson, D. S. & Majumdar, D. *Organometallics* 2, 1529–1535, 1983.

boro-Vinylglycine pinanediol Ester·HCl. The α-chlorovinyl boronate pinanediol ester (10.6 g, 41.7 mmol) was dissolved in THF (100 mL) and added to a freshly prepared solution of lithium hexamethyldisilazide (45.9 mmol) in THF (150 mL) at −78° C. This solution was stirred for 20 h while warming to room temperature. THF was removed in vacuo and hexanes (150 mL) were added. The resulting precipitate was removed by filtration. The filtrate was cooled to −78° C. and a solution of HCl in dioxane (4.0 N, 31.3 mL, 125 mmol) was added. The solution was allowed to warm to room temperature and to stir for 20 h. The solvents were removed in vacuo to yield 7.2 g (26 mmol, 63% yield) of a bright orange, viscous oil which formed a glass when placed under high vacuum. ¹H-NMR (CDCl₃) d 0.76 (s, 3H), 1.21 (s, 3H), 1.36 (s, 3H), 1.83–2.25 (m, 6H), 3.64 (d, 2H), 4.34 (d, 1H), 5.24 (d, 1H), 5.45 (d, 1H), 5.97 (m, 1H), 8.47 (br. s, 3H).

Preparation of H-boroThreonine(OBzl)-pinanediol
Formula:

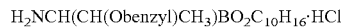

H₂NCH(CH(Obenzyl)CH₃)BO₂C₁₀H₁₆·HCl

Pinacol (1-chloroethyl)boronate. A 250 mL round bottom flask is charged with THF (60 mL) and CH₂Cl₂ (2.63 mL, 41.0 mmol). The solution was cooled to −100° C. with a liquid nitrogen/methanol/H₂O bath. n-BuLi (1.6 N in hexanes, 25.7 mL) was added slowly over the course of 1 h. The resulting solution was stirred for an additional 45 min at −100° C. Pinacol methyl boronate, dissolved in THF (40 mL), was added and the solution was stirred overnight while warming to room temperature. The THF was removed by evaporation and hexanes (100 mL) were added. The resulting precipitate was filtered and the solution concentrated. The residue was distilled at 70° C., 2 mm Hg to yield 2.06 g (30%) of a clear colorless oil. ¹H-NMR (CDCl₃) δ 3.49 (q, 1H), 1.52 (d, 4H), 1.27 (s, 12H).

Pinanediol (1-benzyloxyethyl)boronate. n-BuLi (1.6 N, 13.8 mL) was added to a solution of benzyl alcohol (2.3 mL, 22 mmol) in THF (60 mL) at −78 ° C. followed by DMSO (1.6 mL, 22 mmol). The solution was allowed to warm to room temperature and stir for 1 h. The solution was recooled to 0° C. and a solution of Pinacol (1-chloroethyl)boronate (2.06 g, 11 mmol) in THF (60 mL) was added. The solution was stirred at room temperature for 1 h and then heated at 60° C. for 5 h. The contents of the flask are poured into 0.2 N HCl (300 mL). The layers were separated and the aqueous layer was washed with ether (3×100 mL). The combined organic layers were washed with brine and dried over Na₂SO₄. To this solution was added (s)-pinanediol (1.87 g, 11.0 mmol) and the solution was stirred for 1 day and concentrated to yield an oil. This oil was purified by silica gel column chromatography using 10% ethyl acetate/90% hexane as an eluent. The appropriate fractions are pooled and the solvent evaporated to yield 2.66 g (77% yield) of a pale yellow oil. ¹H-NMR (CDCl₃) δ 7.30 (m, 5H), 4.57 (s, 2H), 4.32 (d, 1H), 3.45 (dq, 1H), 2.39–1.82 (m, 6H), 1.41 (s, 3H), 1.40 (dd, 3H), 1.29 (s, 3H), 0.84 (s, 3H).

Pinanediol (2-benzyloxy-1-chloropropyl)boronate. CH₂Cl₂ (0.80 mL, 12.7 mmol) was added to THF (40 mL) and cooled to −100° C. n-BuLi (1.6 N, 6.3 mL) was slowly added while maintaining a temperature of −100° C. The flask was stirred at −100° C. for an additional 45 min. Pinanediol (1-benzyloxyethyl)boronate (2.66 g, 8.46 mmol), dissolved in THF (20 mL), was added followed by a solution of zinc(II) chloride in ether (1.0 N, 17 mL). The THF was evaporated and the residue was redissolved in hexanes (150 mL). The solution was washed with saturated aqueous ammonium chloride, brine, and dried over MgSO₄. It was concentrated to give a light oil. This oil was purified by silica gel column chromatography (10% ethyl acetate/90% hexanes eluant) to yield 1.55 g (51%) of a clear oil. ¹H-NMR (CDCl₃)δ 7.36 (m, 5H), 4.58 (m, 2H), 4.37 (d, 1H), 3.91 (m, 1H), 3.56 (d, 2H), 2.39–1.81 (m, 6H), 1.40 (d, 3H), 1.34 (d, 3H), 1.29 (s, 3H), 0.84 (s, 3H).

Pinanediol (2-benzyloxy-1-aminopropyl)boronate·HCl. Pinanediol (2-benzyloxy-1-chloropropyl)boronate, dissolved (3.85 g, 10.6 mmol)) in THF (60 mL), was added to a solution of LiHMDS (10.6 mmol) in THF at −78° C. The solution was stirred for 1 h at −78° C. and allowed to warm to room temperature. Solvent was evaporated and the residue redissolved in hexanes (120 mL). The solid was filtered and the filtrate recooled to −78° C., and a solution of HCl in 1,4-dioxane (4 N, 8.0 mL) was added. The solution was allowed to warm to room temperature while stirring overnight. The solvent was evaporated to yield 2.55 g (63%) of a brown oil. ¹H-NMR (CDCl₃) d 8.11 (br s, 3H), 7.35 (m, 5H), 4.57 (m, 2H), 4.32 (m, 1H), 3.16 (br s, 1H), 2.34–1.83 (m, 6H), 1.38 (s, 3H), 1.33 (m, 3H), 1.24 (s, 3H), 0.79 (s, 3H).

Preparation of H-boroSer(OBzl)-pinanediol HCl.
Formula:

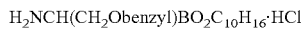

H₂NCH(CH₂Obenzyl)BO₂C₁₀H₁₆·HCl

H-boroSer(OBzl)-pinanediol HCl was prepared by adding Pinanediol 1-chloro-2-benzyloxy-boronate (5.0 g, 14.3 mmol) in THF (60 mL) to a solution of LIHMDS (15 mmol) in THF (60 mL) at −78° C. The solution was allowed to stir while warming to room temperature over a period of 3 h. The THF was evaporated, the residue redissolved in anhydrous hexanes (200 mL), cooled to −78° C., and a solution of HCl in dioxane (4 N, 11.3 mL) was added. The resulting mixture was allowed to stir while warming to room temperature. The solids were removed by filtration. The filtrate was evaporated and triturated with chloroform (50 mL) and refiltered. The chloroform was evaporated and the residue dissolved in hot hexanes (30 mL). As the hexanes were allowed to cool a cream colored solid crystallized. This solid was combined with a solid that had crystallized from the original hexanes filtrate. The combined solids were filtered, dried in vacuo to yield 2.4 g (46%) of a cream colored solid, mp 112–115° C. $^1$H-NMR (CDCl$_3$) 8.16 (br s., 3H), 4.59 (dd, 2H), 4.37 (d, 1H), 4.02 (m, 1H), 3.83 (m, 1H), 3.31 (br s, 1H), 2.31–2.11 (m, 2H). 2.02 (t, 1H), 1.91–1.84 (m, 3H), 1.39 (s, 3H), 1.25 (s, 3H), 0.79 (s, 3H). MS/ESI calculated for C$_{19}$H$_{29}$BNO$_3$+H$^+$: 330.2: Found: 330.3.

Preparation of Pinanediol 1-amino-2-thiophenylethylboronate HCl.
Formula:

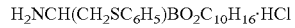

Pinanediol 1-chloro-2-thio(phenyl)ethylboronate. Phenylsulfenyl chloride (2.0 g, 13.8 mmol) was added to a solution of pinanediol vinyl boronate (2.85 g, 13.8 mmol) in CH$_2$Cl$_2$ (30 mL). The solution was stirred for 30 min and then the solution was evaporated to yield 3.9 g (81%) of a pale yellow oil. $^1$H-NMR (CDCl$_3$) δ 7.40 (m, 5H), 4.40 (d, 1H), 3.49 (m, 1H), 3.64 (m, 1H), 3.33 (m, 2H), 2.34–1.89 (m, 6H), 1.43 (s, 3H), 1.30 (s, 3H), 0.85 (s, 3H). MS/APCI calculated for C$_{18}$H$_{24}$BClO$_4$S+H: 351.1. Found: 351.0.

Pinanediol 1-amino-2-thiophenylethylboronate HCl. Pinanediol 1-chloro-2-thio(phenyl)ethylboronate (2.0 g, 5.7 mmol) dissolved in THF (40 mL) was added to a solution LiHMDS (6.0 mmol) in THF (60 mL) at −78° C. The solution was allowed to warm to room temperature and solvent was evaporated. The residue was redissolved in hexanes, filtered and recooled to −78° C. A solution of HCl in dioxane (4 N, 5 mL) was added and the mixture was allowed to stir overnight while warming to room temperature. The solvent was removed to yield 1.2 g (57%) of the desired product as a yellow foam. $^1$H-NMR δ 8.46 (br s, 3H), 4.33 (d, 1H), 3.75 (s, 3H), 3.48 (br s, 2H), 3.15 (m, H), 2.4–1.8 (m, 6H), 1.35 (s, 3H), 1.23 (s, 3H), 0.78 (s, 3H). MS/ESI calculated for C$_{18}$H$_{27}$BNO$_2$S: 332.3. Found: 332.2.

Pinanediol 1-amino-2-thiolsulfenyl(phenvl)ethyl boronate
Formula:

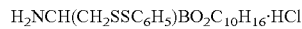

1-Chloro-2-thiolsulfenyl(phenyl)ethyl boronate pinanediol. Phenylthiosulfenyl chloride was prepared by reacting benzene thiol with sulfur dichloride at −78° C. using a published procedure (Can. J. Chem.,51, 3403–3412, 1973). 1-Chloro-2-thiolsulfenyl(phenyl)ethyl boronate pinanediol was obtained by adding phenylthiosulfenyl chloride (3.2 g, 18.2 mmol) dissolved in dichloromethane (30 mL) dropwise over a period of 10 min to a solution of pinanediol vinylboronate (3.7 g, 18.2 mmol) in CH$_2$Cl$_2$ (50 mL) in the presence of CaCO$_3$ (30 mg). The resulting solution was stirred for an additional 1 h at room temperature. The contents of the flask were poured into brine (100 mL), the layers were separated and the organic layer was dried over Na$_2$SO$_4$. The organic layer was evaporated to yield a pale, yellow-green oil which was further purified by silica gel column chromatography (eluant 1% EtOAc/99% Hexanes). The appropriate fractions were pooled and evaporated to yield 2.93 g (7.8 mmol, 43%) of a pale green viscous oil. MS/APCI calculated for C$_{18}$H$_{24}$BClO$_2$S$_2$+H: 383. Found: 383. $^1$H-NMR CDCl$_3$ δ 0.85 (s, 3H), 1.30 (s, 3H), 1.42 (s, 3H), 1.86–2.40 (m, 6H), 3.11–3.32 (m, 2H), 3.73 (t, 1H), 4.37 (dd, 1H), 7.22–7.63 (m, 5H).

Pinanediol 1-amino-2-thiolsulfenyl(phenyl)ethyl boronate. 1-Chloro-2-thiolsulfenyl(phenyl)ethyl boronate pinanediol was treated with lithium hexamethyldisilane by the procedure in pinanediol 1-amino-2-thiophenylehtyboronate to yield the alpha-amino compound. MS/ESI calculated for C$_{18}$H$_{26}$BNO$_2$S$_2$+H: 364. Found: 364.

Preparation of Pinacol 1-amino-3,3,3-trifluorobutyl boronate
Formula:

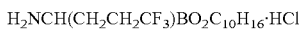

1-Phenylthio-4,4,4-trifluorobutane-1-boronate pinacol ester. Phenylthiomethane boronate pinacol ester was prepared by the procedure in H-borodifluoroethylglycine pinanediol. Diisopropylamine (4.7 ml, 33.6 mmol) was dissolved in THF (10 mL) and stirred at 0° C. in a 100 mL round bottom flask. Butyllithium (12.8 mL, 32.0 mmol, 2.5M in hexanes) was added dropwise to the solution. A solution of phenylthiomethane boronate pinacol ester (8.0 g, 32.0 mmol) in THF (10 mL) was added dropwise rapidly, yielding a white precipitate. The reaction mixture was stirred for 1 hour at 0° C., followed by the dropwise addition of 3,3,3-trifluoropropyl iodide (Lancaster) (15.0 g, 64.0 mmol). The precipitate dissolved and the solution was allowed to warm to room temperature and stirred for 12 hours. The mixture was then treated with excess cold 10% phosphoric acid and stirred for 5 minutes. The reaction mixture was poured into a separatory funnel and extracted with ether (100 mL). The organic layer was dried over sodium sulfate and filtered. The filtrate was concentrated in vacuo and distilled (bp 112–114° C., 0.25 mm Hg) to give 6.53g (59%) of the desired product as a clear oil. $^1$H nmr (CDCl$_3$) δ 7.41–7.11 (m, 5H, C$_6$H$_5$), 2.78 (t, 1H, SCHB), 2.35 (m, 2H, CH$_2$CF$_3$), 1.98 (m, 1H, CH$_2$CH$_2$CF$_3$), 1.23 (s, 12H, CCH$_3$). $^{19}$F nmr δ −116.8 to −117.0 (t, 3H, CF$_3$).

1-iodo-4,4,4-trifluorobutane-1-boronate pinacol ester. 1-Phenylthio-4,4,4-trifluorobutane-1-boronate pinacol ester (3.3g, 9.5 mmol) was dissolved in anhydrous acetonitrile (33 mL). Dry methyl iodide (11.9 mL, 190.6 mmol) was added, followed by the addition of sodium iodide (2.87 g, 19.1 mmol). The reaction mixture was refluxed for 12 h. The solvent was evaporated to give an oily residue which was purified by distillation to give 3.32 g (95.6%), bp 51° C., 0.5 mm Hg. $^1$H nmr (CDCl$_3$) δ 3.21 (t, 1H, ICHB), 2.39 (m, 2H, CH$_2$CF$_3$), 2.05 (m, 2H, CH$_2$CH$_2$CF$_3$), 1.27(s, 12H, CCH$_3$).

1-amino-4,4,4-trifluorobutyl boronate pinanediol ester. 1-iodo-4,4,4-trifluorobutyl pinacol ester (3.4 g, 9.58 mmol) was dissolved in THF (20 mL) and was added dropwise to a solution of lithium bis(trimethylsilyl)amide (Aldrich) (9.6 ml, 9.6 mmol, 1.0M in THF) dissolved in anhydrous THF (20 ml and cooled to −78° C.). The reaction mixture was allowed to warm to room temperature and stirred for 12 hours. It was concentrated in vacuo and hexane was added. The reaction mixture was cooled to −78° C. and 4M anhydrous hydrogen chloride in dioxane (7.2 ml, 28.7 mmol) was added dropwise. The solution was allowed to warm to room temperature and stirred for 3 hours. The reaction mixture was concentrated and chloroform was added. Insoluble material was removed by filtration. The filtrate was evaporated almost to dryness and hexanes were added. Upon standing the product crystallized. It was isolated and washed with cold hexanes to yield 1.7 g (69.8%) of a brown solid. $^1$H nmr (CDCl$_3$) δ 7.80 (bs, 3H), 3.19 (m, 1H), 2.78 (m, 1H), 2.58-2.05 (m, 3H), 1.23 (s, 12H). $^{19}$F nmr (CDCl$_3$) δ −66.67 to −66.59 (t, 3H, CF$_3$).
The following table contains representative examples envisioned by the present invention. For each compound, both epimers at the quaternary center (bearing the R$^4$ substituent) are considered to be specified in the table.
TABLE 2
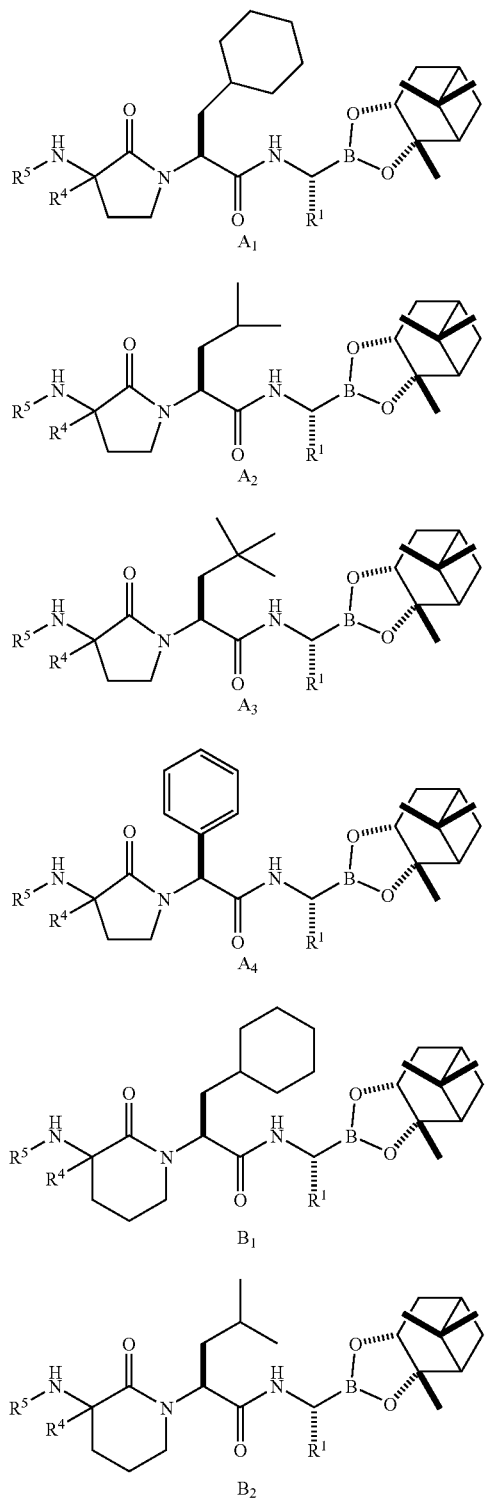
TABLE 2-continued
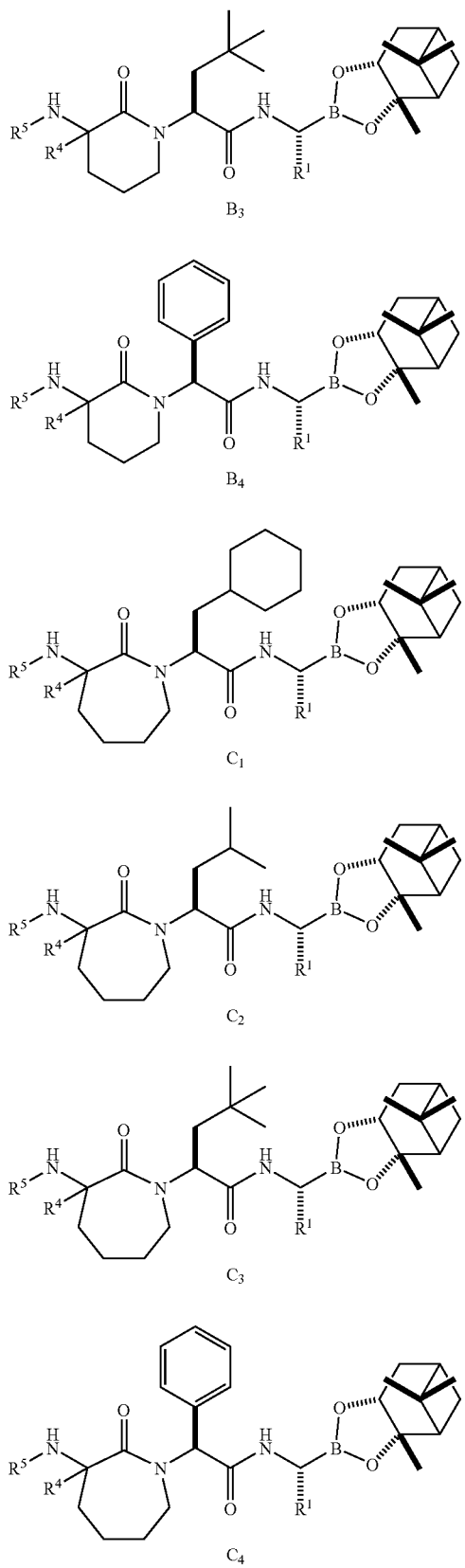

TABLE 2-continued

| Ex. | R¹ | R⁴ | R⁵ |
|---|---|---|---|
| 51 | ethyl | ethyl | m-methylphenylsulfonyl |
| 52 | ethyl | ethyl | m-trifluoromethyl-phenylsulfonyl |
| 53 | ethyl | ethyl | p-isopropylphenyl-sulfonyl |
| 54 | ethyl | ethyl | p-propylphenylsulfonyl |
| 55 | ethyl | ethyl | p-t-butylphenylsulfonyl |
| 56 | ethyl | ethyl | p-carboxyphenyl-sulfonyl |
| 57 | ethyl | ethyl | 4-biphenylsulfonyl |
| 58 | ethyl | ethyl | 1-napthylsulfonyl |
| 59 | ethyl | ethyl | 2-napthylsulfonyl |
| 60 | ethyl | ethyl | 8-quinolinesulfonyl |
| 61 | ethyl | ethyl | benzyl |
| 62 | ethyl | ethyl | N-phenylcarbamoyl |
| 63 | ethyl | ethyl | N-(p-butylphenyl)carbamoyl |
| 64 | ethyl | ethyl | butylsulfonyl |
| 65 | ethyl | ethyl | carbobenzyloxy |
| 66 | ethyl | ethyl | methoxycarbonyl |
| 67 | ethyl | ethyl | benzoyl |
| 68 | ethyl | ethyl | methanesulfonyl |
| 69 | ethyl | ethyl | phenylsulfonyl |
| 70 | ethyl | ethyl | o-nitrophenylsulfonyl |
| 71 | ethyl | ethyl | m-nitrophenylsulfonyl |
| 72 | ethyl | ethyl | m-aminophenylsulfonyl |
| 73 | ethyl | propyl | m-methylphenylsulfonyl |
| 74 | ethyl | propyl | m-trifluoromethyl-phenylsulfonyl |
| 75 | ethyl | propyl | p-isopropylphenyl-sulfonyl |
| 76 | ethyl | propyl | p-propylphenylsulfonyl |
| 77 | ethyl | propyl | p-t-butylphenylsulfonyl |
| 78 | ethyl | propyl | p-carboxyphenyl-sulfonyl |
| 79 | ethyl | propyl | 4-biphenylsulfonyl |
| 80 | ethyl | propyl | 1-napthylsulfonyl |
| 81 | ethyl | propyl | 2-napthylsulfonyl |
| 82 | ethyl | propyl | 8-quinolinesulfonyl |
| 83 | ethyl | propyl | benzyl |
| 84 | ethyl | propyl | N-phenylcarbamoyl |
| 85 | ethyl | propyl | N-(p-butylphenyl)carbamoyl |
| 86 | ethyl | propyl | butylsulfonyl |
| 87 | ethyl | propyl | carbobenzyloxy |
| 88 | ethyl | propyl | methoxycarbonyl |
| 89 | ethyl | propyl | benzoyl |
| 90 | ethyl | propyl | methanesulfonyl |
| 91 | ethyl | propyl | phenylsulfonyl |
| 92 | ethyl | propyl | o-nitrophenylsulfonyl |
| 93 | ethyl | propyl | m-nitrophenylsulfonyl |
| 94 | ethyl | propyl | m-aminophenylsulfonyl |
| 95 | ethyl | isopropyl | m-methylphenylsulfonyl |
| 96 | ethyl | isopropyl | m-trifluoromethyl-phenylsulfonyl |
| 97 | ethyl | isopropyl | p-isopropylphenyl-sulfonyl |
| 98 | ethyl | isopropyl | p-propylphenylsulfonyl |
| 99 | ethyl | isopropyl | p-t-butylphenylsulfonyl |
| 100 | ethyl | isopropyl | p-carboxyphenyl-sulfonyl |
| 101 | ethyl | isopropyl | 4-biphenylsulfonyl |
| 102 | ethyl | isopropyl | 1-napthylsulfonyl |
| 103 | ethyl | isopropyl | 2-napthylsulfonyl |
| 104 | ethyl | isopropyl | 8-quinolinesulfonyl |
| 105 | ethyl | isopropyl | benzyl |
| 106 | ethyl | isopropyl | N-phenylcarbamoyl |
| 107 | ethyl | isopropyl | N-(p-butylphenyl)carbamoyl |
| 108 | ethyl | isopropyl | butylsulfonyl |
| 109 | ethyl | isopropyl | carbobenzyloxy |
| 110 | ethyl | isopropyl | methoxycarbonyl |
| 111 | ethyl | isopropyl | benzoyl |
| 112 | ethyl | isopropyl | methanesulfonyl |
| 113 | ethyl | isopropyl | phenylsulfonyl |
| 114 | ethyl | isopropyl | o-nitrophenylsulfonyl |
| 115 | ethyl | isopropyl | m-nitrophenylsulfonyl |
| 116 | ethyl | isopropyl | m-aminophenylsulfonyl |
| 117 | ethyl | R-2-butyl | m-methylphenylsulfonyl |
| 118 | ethyl | R-2-butyl | m-trifluoromethyl-phenylsulfonyl |
| 119 | ethyl | R-2-butyl | p-isopropylphenyl-sulfonyl |
| 120 | ethyl | R-2-butyl | p-propylphenylsulfonyl |
| 121 | ethyl | R-2-butyl | p-t-butylphenylsulfonyl |
| 122 | ethyl | R-2-butyl | p-carboxyphenyl-sulfonyl |
| 123 | ethyl | R-2-butyl | 4-biphenylsulfonyl |
| 124 | ethyl | R-2-butyl | 1-napthylsulfonyl |
| 125 | ethyl | R-2-butyl | 2-napthylsulfonyl |
| 126 | ethyl | R-2-butyl | 8-quinolinesulfonyl |
| 127 | ethyl | R-2-butyl | benzyl |
| 128 | ethyl | R-2-butyl | N-phenylcarbamoyl |
| 129 | ethyl | R-2-butyl | N-(p-butylphenyl)carbamoyl |
| 130 | ethyl | R-2-butyl | butylsulfonyl |
| 131 | ethyl | R-2-butyl | carbobenzyloxy |
| 132 | ethyl | R-2-butyl | methoxycarbonyl |
| 133 | ethyl | R-2-butyl | benzoyl |
| 134 | ethyl | R-2-butyl | methanesulfonyl |
| 135 | ethyl | R-2-butyl | phenylsulfonyl |
| 136 | ethyl | R-2-butyl | o-nitrophenylsulfonyl |
| 137 | ethyl | R-2-butyl | m-nitrophenylsulfonyl |
| 138 | ethyl | R-2-butyl | m-aminophenylsulfonyl |
| 139 | ethyl | S-2-butyl | m-methylphenylsulfonyl |
| 140 | ethyl | S-2-butyl | m-trifluoromethyl-phenylsulfonyl |
| 141 | ethyl | S-2-butyl | p-isopropylphenyl-sulfonyl |
| 142 | ethyl | S-2-butyl | p-propylphenylsulfonyl |
| 143 | ethyl | S-2-butyl | p-t-butylphenylsulfonyl |
| 144 | ethyl | S-2-butyl | p-carboxyphenyl-sulfonyl |
| 145 | ethyl | S-2-butyl | 4-biphenylsulfonyl |
| 146 | ethyl | S-2-butyl | 1-napthylsulfonyl |
| 147 | ethyl | 3-2-butyl | 2-napthylsulfonyl |
| 148 | ethyl | S-2-butyl | 8-quinolinesulfonyl |
| 149 | ethyl | S-2-butyl | benzyl |
| 150 | ethyl | S-2-butyl | N-phenylcarbamoyl |
| 151 | ethyl | S-2-butyl | N-(p-butylphenyl)carbamoyl |
| 152 | ethyl | S-2-butyl | butylsulfonyl |
| 153 | ethyl | S-2-butyl | carbobenzyloxy |
| 154 | ethyl | S-2-butyl | methoxycarbonyl |
| 155 | ethyl | S-2-butyl | benzoyl |
| 156 | ethyl | 3-2-butyl | methanesulfonyl |
| 157 | ethyl | S-2-butyl | phenylsulfonyl |
| 158 | ethyl | S-2-butyl | o-nitrophenylsulfonyl |
| 159 | ethyl | S-2-butyl | m-nitrophenylsulfonyl |
| 160 | ethyl | S-2-butyl | m-aminophenylsulfonyl |
| 161 | propyl | ethyl | m-methylphenylsulfonyl |
| 162 | propyl | ethyl | m-trifluoromethyl-phenylsulfonyl |
| 163 | propyl | ethyl | p-isopropylphenyl-sulfonyl |
| 164 | propyl | ethyl | p-propylphenylsulfonyl |
| 165 | propyl | ethyl | p-t-butylphenylsulfonyl |
| 166 | propyl | ethyl | p-carboxyphenyl-sulfonyl |
| 167 | propyl | ethyl | 4-biphenylsulfonyl |
| 168 | propyl | ethyl | 1-napthylsulfonyl |
| 169 | propyl | ethyl | 2-napthylsulfonyl |
| 170 | propyl | ethyl | 8-quinolinesulfonyl |
| 171 | propyl | ethyl | benzyl |
| 172 | propyl | ethyl | N-phenylcarbamoyl |
| 173 | propyl | ethyl | N-(p-butylphenyl)carbamoyl |
| 174 | propyl | ethyl | butylsulfonyl |
| 175 | propyl | ethyl | carbobenzyloxy |
| 176 | propyl | ethyl | methoxycarbonyl |
| 177 | propyl | ethyl | benzoyl |
| 178 | propyl | ethyl | methanesulfonyl |
| 179 | propyl | ethyl | phenylsulfonyl |
| 180 | propyl | ethyl | o-nitrophenylsulfonyl |
| 181 | propyl | ethyl | m-nitrophenylsulfonyl |
| 182 | propyl | ethyl | m-aminophenylsulfonyl |
| 183 | propyl | propyl | m-methylphenylsulfonyl |
| 184 | propyl | propyl | m-trifluoromethyl-phenylsulfonyl |
| 185 | propyl | propyl | p-isopropylphenyl-sulfonyl |
| 186 | propyl | propyl | p-propylphenylsulfonyl |
| 187 | propyl | propyl | p-t-butylphenylsulfonyl |
| 188 | propyl | propyl | p-carboxyphenyl-sulfonyl |
| 189 | propyl | propyl | 4-biphenylsulfonyl |
| 190 | propyl | propyl | 1-napthylsulfonyl |
| 191 | propyl | propyl | 2-napthylsulfonyl |
| 192 | propyl | propyl | 8-quinolinesulfonyl |
| 193 | propyl | propyl | benzyl |
| 194 | propyl | propyl | N-phenylcarbamoyl |
| 195 | propyl | propyl | N-(p-butylphenyl)carbamoyl |
| 196 | propyl | propyl | butylsulfonyl |
| 197 | propyl | propyl | carbobenzyloxy |
| 198 | propyl | propyl | methoxycarbonyl |
| 199 | propyl | propyl | benzoyl |
| 200 | propyl | propyl | methanesulfonyl |
| 201 | propyl | propyl | phenylsulfonyl |
| 202 | propyl | propyl | o-nitrophenylsulfonyl |
| 203 | propyl | propyl | m-nitrophenylsulfonyl |
| 204 | propyl | propyl | m-aminophenylsulfonyl |
| 205 | propyl | isopropyl | m-methylphenylsulfonyl |

TABLE 2-continued

| | | | |
|---|---|---|---|
| 206 | propyl | isopropyl | m-trifluoromethyl-phenylsulfonyl |
| 207 | propyl | isopropyl | p-isopropylphenyl-sulfonyl |
| 208 | propyl | isopropyl | p-propylphenylsulfonyl |
| 209 | propyl | isopropyl | p-t-butylphenylsulfonyl |
| 210 | propyl | isopropyl | p-carboxyphenyl-sulfonyl |
| 211 | propyl | isopropyl | 4-biphenylsulfonyl |
| 212 | propyl | isopropyl | 1-napthylsulfonyl |
| 213 | propyl | isopropyl | 2-napthylsulfonyl |
| 214 | propyl | isopropyl | 8-quinolinesulfonyl |
| 215 | propyl | isopropyl | benzyl |
| 216 | propyl | isopropyl | N-phenylcarbamoyl |
| 217 | propyl | isopropyl | N-(p-butylphenyl)carbamoyl |
| 218 | propyl | isopropyl | butylsulfonyl |
| 219 | propyl | isopropyl | carbobenzyloxy |
| 220 | propyl | isopropyl | methoxycarbonyl |
| 221 | propyl | isopropyl | benzoyl |
| 222 | propyl | isopropyl | methanesulfonyl |
| 223 | propyl | isopropyl | phenylsulfonyl |
| 224 | propyl | isopropyl | o-nitrophenylsulfonyl |
| 225 | propyl | isopropyl | m-nitrophenylsulfonyl |
| 226 | propyl | isopropyl | m-aminophenylsulfonyl |
| 227 | propyl | R-2-butyl | m-methylphenylsulfonyl |
| 228 | propyl | R-2-butyl | m-trifluoromethyl-phenylsulfonyl |
| 229 | propyl | R-2-butyl | p-isopropylphenyl-sulfonyl |
| 230 | propyl | R-2-butyl | p-propylphenylsulfonyl |
| 231 | propyl | R-2-butyl | p-t-butylphenylsulfonyl |
| 232 | propyl | R-2-butyl | p-carboxyphenyl-sulfonyl |
| 233 | propyl | R-2-butyl | 4-biphenylsulfonyl |
| 234 | propyl | R-2-butyl | 1-napthylsulfonyl |
| 235 | propyl | R-2-butyl | 2-napthylsulfonyl |
| 236 | propyl | R-2-butyl | 8-quinolinesulfonyl |
| 237 | propyl | R-2-butyl | benzyl |
| 238 | propyl | R-2-butyl | N-phenylcarbamoyl |
| 239 | propyl | R-2-butyl | N-(p-butylphenyl)carbamoyl |
| 240 | propyl | R-2-butyl | butylsulfonyl |
| 241 | propyl | R-2-butyl | carbobenzyloxy |
| 242 | propyl | R-2-butyl | methoxycarbonyl |
| 243 | propyl | R-2-butyl | benzoyl |
| 244 | propyl | R-2-butyl | methanesulfonyl |
| 245 | propyl | R-2-butyl | phenylsulfonyl |
| 246 | propyl | R-2-butyl | o-nitrophenylsulfonyl |
| 247 | propyl | R-2-butyl | m-nitrophenylsulfonyl |
| 248 | propyl | R-2-butyl | m-aminophenylsulfonyl |
| 249 | propyl | S-2-butyl | m-methylphenylsulfonyl |
| 250 | propyl | S-2-butyl | m-trifluoromethyl-phenylsulfonyl |
| 251 | propyl | S-2-butyl | p-isopropylphenyl-sulfonyl |
| 252 | propyl | S-2-butyl | p-propylphenylsulfonyl |
| 253 | propyl | S-2-butyl | p-t-butylphenylsulfonyl |
| 254 | propyl | S-2-butyl | p-carboxyphenyl-sulfonyl |
| 255 | propyl | S-2-butyl | 4-biphenylsulfonyl |
| 256 | propyl | S-2-butyl | 1-napthylsulfonyl |
| 257 | propyl | S-2-butyl | 2-napthylsulfonyl |
| 258 | propyl | S-2-butyl | 8-quinolinesulfonyl |
| 259 | propyl | S-2-butyl | benzyl |
| 260 | propyl | S-2-butyl | N-phenylcarbamoyl |
| 261 | propyl | S-2-butyl | N-(p-butylphenyl)carbamoyl |
| 262 | propyl | S-2-butyl | butylsulfonyl |
| 263 | propyl | S-2-butyl | carbobenzyloxy |
| 264 | propyl | S-2-butyl | methoxycarbonyl |
| 265 | propyl | S-2-butyl | benzoyl |
| 266 | propyl | S-2-butyl | methanesulfonyl |
| 267 | propyl | S-2-butyl | phenylsulfonyl |
| 268 | propyl | S-2-butyl | o-nitrophenylsulfonyl |
| 269 | propyl | S-2-butyl | m-nitrophenylsulfonyl |
| 270 | propyl | S-2-butyl | m-aminophenylsulfonyl |
| 271 | allyl | ethyl | m-methylphenylsulfonyl |
| 272 | allyl | ethyl | m-trifluoromethyl-phenylsulfonyl |
| 273 | allyl | ethyl | p-isopropylphenyl-sulfonyl |
| 274 | allyl | ethyl | p-propylphenylsulfonyl |
| 275 | allyl | ethyl | p-t-butylphenylsulfonyl |
| 276 | allyl | ethyl | p-carboxyphenyl-sulfonyl |
| 277 | allyl | ethyl | 4-biphenylsulfonyl |
| 278 | allyl | ethyl | 1-napthylsulfonyl |
| 279 | allyl | ethyl | 2-napthylsulfonyl |
| 280 | allyl | ethyl | 8-quinolinesulfonyl |
| 281 | allyl | ethyl | benzyl |
| 282 | allyl | ethyl | N-phenylcarbamoyl |
| 283 | allyl | ethyl | N-(p-butylphenyl)carbamoyl |
| 284 | allyl | ethyl | butylsulfonyl |
| 285 | allyl | ethyl | carbobenzyloxy |
| 286 | allyl | ethyl | methoxycarbonyl |
| 287 | allyl | ethyl | benzoyl |
| 288 | allyl | ethyl | methanesulfonyl |
| 289 | allyl | ethyl | phenylsulfonyl |
| 290 | allyl | ethyl | o-nitrophenylsulfonyl |
| 291 | allyl | ethyl | m-nitrophenylsulfonyl |
| 292 | allyl | ethyl | m-aminophenylsulfonyl |
| 293 | allyl | propyl | m-methylphenylsulfonyl |
| 294 | allyl | propyl | m-trifluoromethyl-phenylsulfonyl |
| 295 | allyl | propyl | p-isopropylphenyl-sulfonyl |
| 296 | allyl | propyl | p-propylphenylsulfonyl |
| 297 | allyl | propyl | p-t-butylphenylsulfonyl |
| 298 | allyl | propyl | p-carboxyphenyl-sulfonyl |
| 299 | allyl | propyl | 4-biphenylsulfonyl |
| 300 | allyl | propyl | 1-napthylsulfonyl |
| 301 | allyl | propyl | 2-napthylsulfonyl |
| 302 | allyl | propyl | 8-quinolinesulfonyl |
| 303 | allyl | propyl | benzyl |
| 304 | allyl | propyl | N-phenylcarbamoyl |
| 305 | allyl | propyl | N-(p-butylphenyl)carbamoyl |
| 306 | allyl | propyl | butylsulfonyl |
| 307 | allyl | propyl | carbobenzyloxy |
| 308 | allyl | propyl | methoxycarbonyl |
| 309 | allyl | propyl | Benzoyl |
| 310 | allyl | propyl | methanesulfonyl |
| 311 | allyl | propyl | phenylsulfonyl |
| 312 | allyl | propyl | o-nitrophenylsulfonyl |
| 313 | allyl | propyl | m-nitrophenylsulfonyl |
| 314 | allyl | propyl | m-aminophenylsulfonyl |
| 315 | allyl | isopropyl | m-methylphenylsulfonyl |
| 316 | allyl | isopropyl | m-trifluoromethyl-phenylsulfonyl |
| 317 | allyl | isopropyl | p-isopropylphenyl-sulfonyl |
| 318 | allyl | isopropyl | p-propylphenylsulfonyl |
| 319 | allyl | isopropyl | p-t-butylphenylsulfonyl |
| 320 | allyl | isopropyl | p-carboxyphenyl-sulfonyl |
| 321 | allyl | isopropyl | 4-biphenylsulfonyl |
| 322 | allyl | isopropyl | 1-napthylsulfonyl |
| 323 | allyl | isopropyl | 2-napthylsulfonyl |
| 324 | allyl | isopropyl | 8-quinolinesulfonyl |
| 325 | allyl | isopropyl | benzyl |
| 326 | allyl | isopropyl | N-phenylcarbamoyl |
| 327 | allyl | isopropyl | N-(p-butylphenyl)carbamoyl |
| 328 | allyl | isopropyl | butylsulfonyl |
| 329 | allyl | isopropyl | carbobenzyloxy |
| 330 | allyl | isopropyl | methoxycarbonyl |
| 331 | allyl | isopropyl | benzoyl |
| 332 | allyl | isopropyl | methanesulfonyl |
| 333 | allyl | isopropyl | phenylsulfonyl |
| 334 | allyl | isopropyl | o-nitrophenylsulfonyl |
| 335 | allyl | isopropyl | m-nitrophenylsulfonyl |
| 336 | allyl | isopropyl | m-aminophenylsulfonyl |
| 337 | allyl | R-2-butyl | m-methylphenylsulfonyl |
| 338 | allyl | R-2-butyl | m-trifluoromethyl-phenylsulfonyl |
| 339 | allyl | R-2-butyl | p-isopropylphenyl-sulfonyl |
| 340 | allyl | R-2-butyl | p-propylphenylsulfonyl |
| 341 | allyl | R-2-butyl | p-t-butylphenylsulfonyl |
| 342 | allyl | R-2-butyl | p-carboxyphenyl-sulfonyl |
| 343 | allyl | R-2-butyl | 4-biphenylsulfonyl |
| 344 | allyl | R-2-butyl | 1-napthylsulfonyl |
| 345 | allyl | R-2-butyl | 2-napthylsulfonyl |
| 346 | allyl | R-2-butyl | 8-quinolinesulfonyl |
| 347 | allyl | R-2-butyl | benzyl |
| 348 | allyl | R-2-butyl | N-phenylcarbamoyl |
| 349 | allyl | R-2-butyl | N-(p-butylphenyl)carbamoyl |
| 350 | allyl | R-2-butyl | butylsulfonyl |
| 351 | allyl | R-2-butyl | carbobenzyloxy |
| 352 | allyl | R-2-butyl | methoxycarbonyl |
| 353 | allyl | R-2-butyl | benzoyl |
| 354 | allyl | R-2-butyl | methanesulfonyl |
| 355 | allyl | R-2-butyl | phenylsulfonyl |
| 356 | allyl | R-2-butyl | o-nitrophenylsulfonyl |
| 357 | allyl | R-2-butyl | m-nitrophenylsulfonyl |
| 358 | allyl | R-2-butyl | m-aminophenylsulfonyl |
| 359 | allyl | S-2-butyl | m-methylphenylsulfonyl |
| 360 | allyl | S-2-butyl | m-trifluoromethyl-phenylsulfonyl |
| 361 | allyl | S-2-butyl | p-isopropylphenyl-sulfonyl |
| 362 | allyl | S-2-butyl | p-propylphenylsulfonyl |
| 363 | allyl | S-2-butyl | p-t-butylphenylsulfonyl |

TABLE 2-continued

| | | | |
|---|---|---|---|
| 364 | allyl | S-2-butyl | p-carboxylphenyl-sulfonyl |
| 365 | allyl | S-2-butyl | 4-biphenylsulfonyl |
| 366 | allyl | S-2-butyl | 1-napthylsulfonyl |
| 367 | allyl | S-2-butyl | 2-napthylsulfonyl |
| 368 | allyl | S-2-butyl | 8-quinolinesulfonyl |
| 369 | allyl | S-2-butyl | benzyl |
| 370 | allyl | S-2-butyl | N-phenylcarbamoyl |
| 371 | allyl | S-2-butyl | N-(p-butylphenyl)carbamoyl |
| 372 | allyl | S-2-butyl | butylsulfonyl |
| 373 | allyl | S-2-butyl | carbobenzyloxy |
| 374 | allyl | S-2-butyl | methoxycarbonyl |
| 375 | allyl | S-2-butyl | benzoyl |
| 376 | allyl | S-2-butyl | methanesulfonyl |
| 377 | allyl | S-2-butyl | phenylsulfonyl |
| 378 | allyl | S-2-butyl | o-nitrophenylsulfonyl |
| 379 | allyl | S-2-butyl | m-nitrophenylsulfonyl |
| 380 | allyl | S-2-butyl | m-aminophenylsulfonyl |
| 381 | 2,2-difluoroethyl | ethyl | m-methylphenylsulfonyl |
| 382 | 2,2-difluoroethyl | ethyl | m-trifluoromethyl-phenylsulfonyl |
| 383 | 2,2-difluoroethyl | ethyl | p-isopropylphenyl-sulfonyl |
| 384 | 2,2-difluoroethyl | ethyl | p-propylphenylsulfonyl |
| 385 | 2,2-difluoroethyl | ethyl | p-t-butylphenylsulfonyl |
| 386 | 2,2-difluoroethyl | ethyl | p-carboxylphenyl-sulfonyl |
| 387 | 2,2-difluoroethyl | ethyl | 4-biphenylsulfonyl |
| 388 | 2,2-difluoroethyl | ethyl | 1-napthylsulfonyl |
| 389 | 2,2-difluoroethyl | ethyl | 2-napthylsulfonyl |
| 390 | 2,2-difluoroethyl | ethyl | 8-quinolinesulfonyl |
| 391 | 2,2-difluoroethyl | ethyl | benzyl |
| 392 | 2,2-difluoroethyl | ethyl | N-phenylcarbamoyl |
| 393 | 2,2-difluoroethyl | ethyl | N-(p-butylphenyl)carbamoyl |
| 394 | 2,2-difluoroethyl | ethyl | butylsulfonyl |
| 395 | 2,2-difluoroethyl | ethyl | carbobenzyloxy |
| 396 | 2,2-difluoroethyl | ethyl | methoxycarbonyl |
| 397 | 2,2-difluoroethyl | ethyl | Benzoyl |
| 398 | 2,2-difluoroethyl | ethyl | Methanesulfonyl |
| 399 | 2,2-difluoroethyl | ethyl | Phenylsulfonyl |
| 400 | 2,2-difluoroethyl | ethyl | o-nitrophenylsulfonyl |
| 401 | 2,2-difluoroethyl | ethyl | m-nitrophenylsulfonyl |
| 402 | 2,2-difluoroethyl | ethyl | m-aminophenylsulfonyl |
| 403 | 2,2-difluoroethyl | propyl | m-methylphenylsulfonyl |
| 404 | 2,2-difluoroethyl | propyl | m-trifluoromethyl-phenylsulfonyl |
| 405 | 2,2-difluoroethyl | propyl | p-isopropylphenyl-sulfonyl |
| 406 | 2,2-difluoroethyl | propyl | p-propylphenylsulfonyl |
| 407 | 2,2-difluoroethyl | propyl | p-t-butylphenylsulfonyl |
| 408 | 2,2-difluoroethyl | propyl | p-carboxylphenyl-sulfonyl |
| 409 | 2,2-difluoroethyl | propyl | 4-biphenylsulfonyl |
| 410 | 2,2-difluoroethyl | propyl | 1-napthylsulfonyl |
| 411 | 2,2-difluoroethyl | propyl | 2-napthylsulfonyl |
| 412 | 2,2-difluoroethyl | propyl | 8-quinolinesulfonyl |
| 413 | 2,2-difluoroethyl | propyl | benzyl |
| 414 | 2,2-difluoroethyl | propyl | N-phenylcarbamoyl |
| 415 | 2,2-difluoroethyl | propyl | N-(p-butylphenyl)carbamoyl |
| 416 | 2,2-difluoroethyl | propyl | butylsulfonyl |
| 417 | 2,2-difluoroethyl | propyl | carbobenzyloxy |
| 418 | 2,2-difluoroethyl | propyl | methoxycarbonyl |
| 419 | 2,2-difluoroethyl | propyl | benzoyl |
| 420 | 2,2-difluoroethyl | propyl | methanesulfonyl |
| 421 | 2,2-difluoroethyl | propyl | phenylsulfonyl |
| 422 | 2,2-difluoroethyl | propyl | o-nitrophenylsulfonyl |
| 423 | 2,2-difluoroethyl | propyl | m-nitrophenylsulfonyl |
| 424 | 2,2-difluoroethyl | propyl | m-aminophenylsulfonyl |
| 425 | 2,2-difluoroethyl | isopropyl | m-methylphenylsulfonyl |
| 426 | 2,2-difluoroethyl | isopropyl | m-trifluoromethyl-phenylsulfonyl |
| 427 | 2,2-difluoroethyl | isopropyl | p-isopropylphenyl-sulfonyl |
| 428 | 2,2-difluoroethyl | isopropyl | p-propylphenylsulfonyl |
| 429 | 2,2-difluoroethyl | isopropyl | p-t-butylphenylsulfonyl |
| 430 | 2,2-difluoroethyl | isopropyl | p-carboxylphenyl-sulfonyl |
| 431 | 2,2-difluoroethyl | isopropyl | 4-biphenylsulfonyl |
| 432 | 2,2-difluoroethyl | isopropyl | 1-napthylsulfonyl |
| 433 | 2,2-difluoroethyl | isopropyl | 2-napthylsulfonyl |
| 434 | 2,2-difluoroethyl | isopropyl | 8-quinolinesulfonyl |
| 435 | 2,2-difluoroethyl | isopropyl | benzyl |
| 436 | 2,2-difluoroethyl | isopropyl | N-phenylcarbamoyl |
| 437 | 2,2-difluoroethyl | isopropyl | N-(p-butylphenyl)carbamoyl |
| 438 | 2,2-difluoroethyl | isopropyl | butylsulfonyl |
| 439 | 2,2-difluoroethyl | isopropyl | carbobenzyloxy |
| 440 | 2,2-difluoroethyl | isopropyl | methoxycarbonyl |
| 441 | 2,2-difluoroethyl | isopropyl | benzoyl |
| 442 | 2,2-difluoroethyl | isopropyl | methanesulfonyl |
| 443 | 2,2-difluoroethyl | isopropyl | phenylsulfonyl |
| 444 | 2,2-difluoroethyl | isopropyl | o-nitrophenylsulfonyl |
| 445 | 2,2-difluoroethyl | isopropyl | m-nitrophenylsulfonyl |
| 446 | 2,2-difluoroethyl | isopropyl | m-aminophenylsulfonyl |
| 447 | 2,2-difluoroethyl | R-2-butyl | m-methylphenylsulfonyl |
| 448 | 2,2-difluoroethyl | R-2-butyl | m-trifluoromethyl-phenylsulfonyl |
| 449 | 2,2-difluoroethyl | R-2-butyl | p-isopropylphenyl-sulfonyl |
| 450 | 2,2-difluoroethyl | R-2-butyl | p-propylphenylsulfonyl |
| 451 | 2,2-difluoroethyl | R-2-butyl | p-t-butylphenylsulfonyl |
| 452 | 2,2-difluoroethyl | R-2-butyl | p-carboxylphenyl-sulfonyl |
| 453 | 2,2-difluoroethyl | R-2-butyl | 4-biphenylsulfonyl |
| 454 | 2,2-difluoroethyl | R-2-butyl | 1-napthylsulfonyl |
| 455 | 2,2-difluoroethyl | R-2-butyl | 2-napthylsulfonyl |
| 456 | 2,2-difluoroethyl | R-2-butyl | 8-quinolinesulfonyl |
| 457 | 2,2-difluoroethyl | R-2-butyl | benzyl |
| 458 | 2,2-difluoroethyl | R-2-butyl | N-phenylcarbamoyl |
| 459 | 2,2-difluoroethyl | R-2-butyl | N-(p-butylphenyl)carbamoyl |
| 460 | 2,2-difluoroethyl | R-2-butyl | butylsulfonyl |
| 461 | 2,2-difluoroethyl | R-2-butyl | carbobenzyloxy |
| 462 | 2,2-difluoroethyl | R-2-butyl | methoxycarbonyl |
| 463 | 2,2-difluoroethyl | R-2-butyl | benzoyl |
| 464 | 2,2-difluoroethyl | R-2-butyl | methanesulfonyl |
| 465 | 2,2-difluoroethyl | R-2-butyl | phenylsulfonyl |
| 466 | 2,2-difluoroethyl | R-2-butyl | o-nitrophenylsulfonyl |
| 467 | 2,2-difluoroethyl | R-2-butyl | m-nitrophenylsulfonyl |
| 468 | 2,2-difluoroethyl | R-2-butyl | m-aminophenylsulfonyl |
| 469 | 2,2-difluoroethyl | S-2-butyl | m-methylphenylsulfonyl |
| 470 | 2,2-difluoroethyl | S-2-butyl | m-trifluoromethyl-phenylsulfonyl |
| 471 | 2,2-difluoroethyl | S-2-butyl | p-isopropylphenyl-sulfonyl |
| 472 | 2,2-difluoroethyl | S-2-butyl | p-propylphenylsulfonyl |
| 473 | 2,2-difluoroethyl | S-2-butyl | p-t-butylphenylsulfonyl |
| 474 | 2,2-difluoroethyl | S-2-butyl | p-carboxylphenyl-sulfonyl |
| 475 | 2,2-difluoroethyl | S-2-butyl | 4-biphenylsulfonyl |
| 476 | 2,2-difluoroethyl | S-2-butyl | 1-napthylsulfonyl |
| 477 | 2,2-difluoroethyl | S-2-butyl | 2-napthylsulfonyl |
| 478 | 2,2-difluoroethyl | S-2-butyl | 8-quinolinesulfonyl |
| 479 | 2,2-difluoroethyl | S-2-butyl | benzyl |
| 480 | 2,2-difluoroethyl | S-2-butyl | N-phenylcarbamoyl |
| 481 | 2,2-difluoroethyl | S-2-butyl | N-p-butylphenyl)carbamoyl |
| 482 | 2,2-difluoroethyl | S-2-butyl | Butylsulfonyl |
| 483 | 2,2-difluoroethyl | S-2-butyl | Carbobenzyloxy |
| 484 | 2,2-difluoroethyl | S-2-butyl | methoxycarbonyl |
| 485 | 2,2-difluoroethyl | S-2-butyl | benzoyl |
| 486 | 2,2-difluoroethyl | S-2-butyl | methanesulfonyl |
| 487 | 2,2-difluoroethyl | S-2-butyl | phenylsulfonyl |
| 488 | 2,2-difluoroethyl | S-2-butyl | o-nitrophenylsulfonyl |
| 489 | 2,2-difluoroethyl | S-2-butyl | m-nitrophenylsulfonyl |
| 490 | 2,2-difluoroethyl | S-2-butyl | m-aminophenylsulfonyl |

Utility

The compounds of Formula (I) are expected to inhibit the activity of Hepatitis C Virus NS3 protease. The NS3 protease inhibition is demonstrated using assays for NS3 protease activity, for example, using the assay described below for assaying inhibitors of NS3 protease. The compounds of Formula (I) are expected to show activity against NS3 protease in cells, as demonstrated by the cellular assay described below. Thus, the compounds of Formula (I) are potentially useful in the cure and prevention of HCV infections.

Expression and Purification of NS3 Protease

The plasmid cf1SODp600, containing the complete coding region of HCV NS3 protease, genotype 1a, was obtained from ATCC (database accession: DNA Seq. Acc. M62321, originally deposited by Chiron Corporation). PCR primers were designed that allow amplification of the DNA fragment encoding the NS3 protease catalytic domain (amino acids 1 to 192) as well as its two N-terminal fusions, a 5 amino acid leader sequence MGAQH (SEQ. ID. NO.:3) (serving as a expression tag) and a 15 amino acid His tag MRGSHHH-HHHMGAQH (SEQ. ID. NO.:4). The NS3 protease constructs were cloned in the bacterial expression vector under the control of the T7 promoter and transformed in E. coli BL 21 (DE3) cells. Expression of the NS3 protease was obtained by addition of 1 mM IPTG and cells were growing for additional 3 h at 25° C. The NS3 protease constructs have several fold difference in expression level, but exhibit the same level of solubility and enzyme specific activity. A typical 10 L fermentation yielded approximately 200 g of wet cell paste. The cell paste was stored at −80° C. The NS3 protease was purified based on published procedures (Steinkuhler C. et al. *Journal of Virology* 70, 6694–6700, 1996 and Steinkuhler C. et al. *Journal of Biological Chemistry* 271, 6367–6373, 1996.) with some modifications. Briefly, the cells were resuspended in lysis buffer (10 mL/g) containing PBS buffer (20 mM sodium phosphate, pH 7.4, 140 mM NaCl), 50% glycerol, 10 mM DTT, 2% CHAPS and 1 mM PMSF. Cell lysis was performed with use of microfluidizer. After homogenizing, DNase was added to a final concentration 70 U/mL and cell lysate was incubated at 4° C. for 20 min. After centrifugation at 18,000 rpm for 30 min at 4° C. supernatant was applied on SP Sepharose column (Pharmacia), previously equilibrated at a flow rate 3 mL/min in buffer A (PBS buffer, 10% glycerol, 3 mM DTT). The column was extensively washed with buffer A and the protease was eluted by applying 25 column volumes of a linear 0.14–1.0 M NaCl gradient. NS3 containing fractions were pooled and concentrated on an Amicon stirred ultrafiltration cell using a YM-10 membrane. The enzyme was further purified on 26/60 Superdex 75 column (Pharmacia), equilibrated in buffer A. The sample was loaded at a flow rate 1 mL/min, the column was then washed with a buffer A at a flow rate 2 mL/min. Finally, the NS3 protease containing fractions were applied on Mono S 10/10 column (Pharmacia) equilibrated in 50 mM Tris.HCl buffer, pH 7.5, 10% glycerol and 1 mM DTT and operating at flow rate 2 mL/min. Enzyme was eluted by applying 20 column volumes of a linear 0.1–0.5 M NaCl gradient. Based on SDS-PAGE analysis as well as HPLC analysis and active site titration, the purity of the HCV NS3 1a protease was greater than 95%. The enzyme was stored at −70° C. and diluted just prior to use.

Enzyme Assays

Concentrations of protease were determined in the absence of NS4a by using the peptide ester substrate Ac-DED(Edans)EEAbuψ(COO)ASK(Dabcyl)-NH$_2$ (Taliani et al. *Anal. Biochem.* 240, 60–67, 1996.) (SEQ. ID. NO.:8) and the inhibitor, H-Asp-Glu-Val-Val-Pro-boroAlg-OH (SEQ. ID. NO.:5), and by using tight binding reaction conditions (Bieth, *Methods Enzymol.* 248, 59–85, 1995). Best data was obtained for an enzyme level of 50 nM. Alternately, protease (63 µg/mL) was allowed to react with 3 µM NS4a, 0.10 mM Ac-Glu-Glu-Ala-Cys-pNA (SEQ. ID. NO.:6), and varying level of H-Asp-Glu-Val-Val-Pro-boroAlg-OH (0–6 µM). Concentrations of protease were determined from linear plots of Activity vs. conc. Of H-Asp-Glu-Val-Val-Pro-boroAlg-OH. Molar concentrations of proteases were determined from the x-intercept.

$K_m$ values were determined measuring the rate of hydrolysis of the ester substrate over a range of concentrations from 5.0 to 100 µM in the presence of 3 µM KKNS4a (KKGSVVIVGRIVLSGKPAIIPKK) (SEQ. ID. NO.:7). Assay were run at 25° C., by incubating ~1 nM enzyme with NS4a for 5 min in 148 µl of buffer (50 mM Tri buffer, pH 7.0, 50% glycerol, 2% Chaps, and 5.0 mM DTT. Substrate (2.0 µl) in buffer was added and the reaction was allowed to proceed for 15 min. Reactions were quenched by adding 3.0 RL of 10% TFA, and the levels of hydrolysis were determined by HPLC. Aliquots (50 µL) were injected on the HPLC and linear gradients from 90% water, 10% acetonitrile and 0.10% TFA to 10% water, 90% acetonitrile and 0.10% TFA were run at a flow rate of 1.0 mL/min over a period of 30 min. HPLCs were run on a HP1090 using a Rainin 4.6×250 mm C18 column (cat # 83–201-C) fluorescent detection using 350 and 500 nm as excitation and emission wavelengths, respectively. Levels of hydrolysis were determined by measuring the area of the fluorescent peak at 5.3 min. 100% hydrolysis of a 5.0 µM sample gave an area of 7.95±0.38 fluorescence units.). Kinetic constants were determined from the iterative fit of the Michaelis equation to the data. Results are consistent with data from Liveweaver Burk fits and data collected for the 12.8 min peak measured at 520 nm.

Enzyme activity was also measured by measuring the increase in fluorescence with time by exciting at 355 nm and measuring emission at 495 nm using a Perkin Elmer LS 50 spectrometer. A substrate level of 5.0 µM was used for all fluorogenic assays run on the spectrometer.

Inhibitor Evaluation In vitro

Inhibitor effectiveness was determined by measuring enzyme activity both in the presence and absence of inhibitor. Velocities were fit to the equation for competitive inhibition for individual reactions of inhibitors with the enzyme using $$v_i/v_o = (K_m(1+I/K_i)+S)/(K_m+S).$$

The ratio $v_i/v_o$ is equal to the ratio of the Michaelis equations for velocities measured in the presence ($v_i$) and absence ($v_o$) of inhibitor. Values of $v_i/v_o$ were measured over a range of inhibitor concentrations with the aid of an Excel™ Spreadsheet. Reported $K_i$ values are the average of 3–5 separate determinations. Under the conditions of this assay, the $IC_{50}$ and $K_i$s are comparable measures of inhibitor effectiveness.

Using the methodology described above, a number of compounds of the present invention were found to exhibit a $K_i$ of ≦60 µM, thereby confirming the utility of the compounds of the present invention as effective NS3 protease inhibitors.

Inhibitor Evaluation in Cell Assay.

The following method was devised to assess inhibitory action of test compounds on the HCV NS3 protease in cultured cells. Because it is not possible to efficiently infect cells with hepatitis C virus, an assay was developed based on co-expression in transfected cell lines of two plasmids, one is able to direct synthesis of the NS3 protease and the other to provide a polypeptide analogous to a part of the HCV non-structural protein containing a single known peptide sequence highly susceptible to cleavage by the protease. When installed in cultured cells by one of a variety of standard methods, the substrate plasmid produces a stable polypeptide of approximately 50 KD, but when the plasmid coding for the viral protease is co-expressed, the enzymatic action of the protease hydrolyzes the substrate at a unique sequence between a cysteine and a serine pair, yielding products which can be detected by antibody-based technology, eg, a western blot. Quantitation of the amounts of precursor and products can be done by scanning film auto-radiograms of the blots or direct luminescense-based emissions from the blots in a commercial scanning device. The coding sequences for the NS3 protease and the substrate were taken from genotype 1a of HCV, but other genotypes, eg 2a, may be substituted with similar results.

The DNA plasmids are introduced into cultured cells using electroporation, liposomes or other means. Synthesis of the protease and the substrate begin shortly after introduction and may be detected within a few hours by immunological means. Therefore, test compounds are added at desired concentrations to the cells within a few minutes after introducing the plasmids. The cells are then placed in a standard $CO_2$ incubator at 37° C., in tissue culture medium eg Dulbecco-modified MEM containing 10% bovine serum. After 6–48 hours, the cells are collected by physically scraping them from plastic dishes in which they have been growing, centrifuging them and then lysing about $10^6$ of the concentrated cells in a minimal volume of buffered detergent, eg 20 μl of 1% sodium dodecyl sulfate in 0.10 M Tris-HCl, pH 6.5, containing 1% mercaptaethanol and 7% glycerol. The samples are then loaded onto a standard SDS polyacrylamide gel, the polypeptides separated by electrophoresis, and the gel contents then electroblotted onto nitrocellulose or other suitable paper support, and the substrate and products detected by decoration with specific antibodies.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed:

1. A compound of Formula (I):

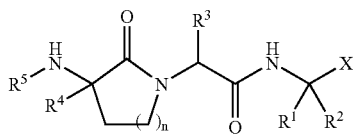

or a stereoisomer or pharmaceutically acceptable salt form thereof, wherein;

the lactam ring of Formula (I) is substituted with 0–2 $R^b$;

X is selected from the group: $B(OH)_2$, $BY^1Y^2$, and $C(=O)C(=O)NHR^{1a}$;

$Y^1$ and $Y^2$ are independently selected from:
a) —OH,
b) —F,
c) —$NR^{18}R^{19}$,
d) $C_1$–$C_8$ alkoxy, or
when taken together, $Y^1$ and $Y^2$ form:
e) a cyclic boron ester comprising from 2 to 20 carbon atoms, and, optionally, 1, 2, or 3 heteroatoms which can be N, S, or O;
f) a cyclic boron amide comprising from 2 to 20 carbon atoms and, optionally, 1, 2, or 3 heteroatoms which can be N, S, or O; or
g) a cyclic boron amide-ester comprising from 2 to 20 carbon atoms and, optionally, 1, 2, or 3 heteroatoms which can be N, S, or O;

$R^1$ is selected from the group:
$C_{1-10}$ alkyl substituted with 0–3 $R^a$;
$C_{2-10}$ alkenyl substituted with 0–3 $R^a$;
$C_{2-10}$ alkynyl substituted with 0–3 $R^a$; and
$C_{3-6}$ cycloalkyl substituted with 0–3 $R^a$;

$R^{1a}$ is selected from the group:
$C_{1-10}$ alkyl substituted with 0–3 $R^a$;
$C_{2-10}$ alkenyl substituted with 0–3 $R^a$;
$C_{2-10}$ alkynyl substituted with 0–3 $R^a$; and
$C_{3-6}$ cycloalkyl substituted with 0–3 $R^a$;

$R^a$ is selected at each occurrence from the group:
$C_{1-3}$ alkyl, $C_{3-6}$ cycloalkyl, Cl, F, Br, I, $CF_3$, OH, =O, $C_{1-6}$ alkoxy, SH, —S—$C_{1-6}$ alkyl;
phenyl substituted with 0–3 $R^b$;
naphthyl substituted with 0–3 $R^b$;
—O—$(CH_2)_q$-phenyl substituted with 0–3 $R^b$;
—O—$(CH_2)_q$-naphthyl substituted with 0–3 $R^b$; and
5–10 membered heteroaryl consisting of carbon atoms and 1–4 heteroatoms selected from the group: O, S, and N, and substituted with 0–3 $R^b$;

$R^b$ is selected at each occurrence from the group:
$C_{1-6}$ alkyl, Cl, F, Br, I, OH, $C_{1-6}$ alkoxy, —CN, —$NO_2$, $C(O)OR^7$, $NR^dR^d$, $CF_3$, $OCF_3$, and $C_{3-6}$ cycloalkyl;

$R^2$ is H;
alternatively, $R^1$ and $R^2$ combine to form a $C_{3-5}$ cycloalkyl group;

$R^3$ is selected from the group:
$C_{1-6}$ alkyl substituted with 0–2 $R^a$;
$C_{2-6}$ alkenyl substituted with 0–2 $R^a$;
$C_{2-6}$ alkynyl substituted with 0–2 $R^a$;
—$(CH_2)_q$-$C_{3-6}$ cycloalkyl substituted with 0–2 $R^a$;
—$(CH_2)_q$-phenyl substituted with 0–2 $R^a$;
—$(CH_2)_q$-naphthyl substituted with 0–2 $R^a$; and
—$(CH_2)_q$-5–10 membered heteroaryl consisting of carbon atoms and 1–4 heteroatoms selected from the group: O, S, and N, and substituted with 0–2 $R^a$;

$R^4$ is selected from the group: H,
  $C_{1-6}$ alkyl substituted with 0–3 $R^b$;
  phenyl substituted with 0–3 $R^b$;
  benzyl substituted with 0–3 $R^b$; and
  phenethyl substituted with 0–3 $R^b$;

$R^5$ is H or $Q$-$R^{5a}$;

Q is 0, 1, 2, or 3 amino acids;

$R^{5a}$ is selected from the group: —S(O)$R^6$, —S(O)$_2R^6$, —C(O)$R^6$, —C(O)O$R^8$, —C(O)NH$R^6$, $C_{1-3}$ alkyl-$R^{6a}$, $C_{2-6}$ alkenyl-$R^{6a}$, and $C_{2-6}$ alkynyl-$R^{6a}$;

$R^6$ is selected from the group:
  $C_{1-6}$ alkyl substituted with 0–3 $R^c$;
  phenyl substituted with 0–3 $R^c$;
  naphthyl substituted with 0–3 $R^c$;
  benzyl substituted with 0–3 $R^c$; and
  5–10 membered heteroaryl consisting of carbon atoms and 1–4 heteroatoms selected from the group: O, S, and N, substituted with 0–3 $R^c$;

$R^{6a}$ is selected from the group:
  phenyl substituted with 0–3 $R^c$;
  naphthyl substituted with 0–3 $R^c$;
  benzyl substituted with 0–3 $R^c$; and
  5–10 membered heteroaryl consisting of carbon atoms and 1–4 heteroatoms selected from the group: O, S, and N, substituted with 0–3 $R^c$;

$R^c$ is selected at each occurrence from the group:
  $C_{1-4}$ alkyl, $C_{1-4}$ alkoxy, CF$_3$, OCF$_3$, Cl, F, Br, I, =O, OH, phenyl, C(O)O$R^7$, N$R^dR^d$, —CN, and NO$_2$;

$R^d$ is selected at each occurrence from the group: H and CH$_3$;

$R^7$ is selected at each occurrence from the group: H and $C_{1-6}$ alkyl;

$R^8$ is selected from the group: $C_{1-6}$ alkyl, benzyl, and $C_{3-6}$ cycloalkyl-methyl;

$R^{18}$ and $R^{19}$ at each occurrence are independently selected from H, $C_1$–$C_4$ alkyl, aryl($C_1$–$C_4$ alkyl)-, and $C_3$–$C_7$ cycloalkyl;

n is selected from the group: 1, 2, and 3; and q is selected from the group: 0, 1, and 2.

2. A compound according to claim 1 of Formula (I):

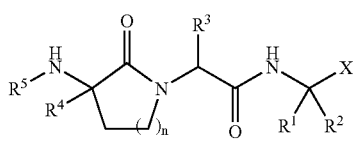

(I)

or a stereoisomer or pharmaceutically acceptable salt form thereof, wherein;

the lactam ring of Formula (I) is substituted with 0–2 $R^b$;

X is selected from the group: B(OH)$_2$, BY$^1$Y$^2$, and C(=O)C(=O) NH$R^{1a}$;

$Y^1$ and $Y^2$ are independently selected from:
  a) —OH,
  b) —F,
  c) —N$R^{18}R^{19}$,
  d) $C_1$–$C_8$ alkoxy, or
  when taken together, $Y^1$ and $Y^2$ form:
  e) a cyclic boron ester comprising from 2 to 20 carbon atoms, and, optionally, 1, 2, or 3 heteroatoms which can be N, S, or O;
  f) a cyclic boron amide comprising from 2 to 20 carbon atoms and, optionally, 1, 2, or 3 heteroatoms which can be N, S, or O; or
  g) a cyclic boron amide-ester comprising from 2 to 20 carbon atoms and, optionally, 1, 2, or 3 heteroatoms which can be N, S, or O;

$R^1$ is selected from the group:
  $C_{1-6}$ alkyl substituted with 0–3 $R^a$;
  $C_{2-6}$ alkenyl substituted with 0–3 $R^a$;
  $C_{2-6}$ alkynyl substituted with 0–3 $R^a$; and
  $C_{3-6}$ cycloalkyl substituted with 0–3 $R^a$;

$R^{1a}$ is selected from the group:
  $C_{1-10}$ alkyl substituted with 0–3 $R^a$;
  $C_{2-10}$ alkenyl substituted with 0–3 $R^a$;
  $C_{2-10}$ alkynyl substituted with 0–3 $R^a$; and
  $C_{3-6}$ cycloalkyl substituted with 0–3 $R^a$;

$R^a$ is selected at each occurrence from the group:
  $C_{1-3}$ alkyl, $C_{3-6}$ cycloalkyl, Cl, F, Br, I, CF$_3$, OH, =O, $C_{1-6}$ alkoxy, SH, —S—$C_{1-6}$ alkyl;
  phenyl substituted with 0–3 $R^b$;
  naphthyl substituted with 0–3 $R^b$;
  —O—(CH$_2$)$_q$-phenyl substituted with 0–3 $R^b$;
  —O—(CH$_2$)$_q$-naphthyl substituted with 0–3 $R^b$; and
  5–10 membered heteroaryl consisting of carbon atoms and 1–4 heteroatoms selected from the group: O, S, and N, and substituted with 0–3 $R^b$;

$R^b$ is selected at each occurrence from the group:
  $C_{1-6}$ alkyl, Cl, F, Br, I, OH, $C_{1-6}$ alkoxy, —CN, —NO$_2$, C(O)O$R^7$, N$R^dR^d$, CF$_3$, OCF$_3$, and $C_{3-6}$ cycloalkyl;

$R^2$ is H;

alternatively, $R^1$ and $R^2$ combine to form a $C_{3-5}$ cycloalkyl group;

$R^3$ is selected from the group:
  $C_{1-6}$ alkyl substituted with 0–2 $R^a$;
  $C_{2-6}$ alkenyl substituted with 0–2 $R^a$;
  $C_{2-6}$ alkynyl substituted with 0–2 $R^a$;
  —(CH$_2$)$_q$—$C_{3-6}$ cycloalkyl substituted with 0–2 $R^a$;
  —(CH$_2$)$_q$-phenyl substituted with 0–2 $R^a$;
  —(CH$_2$)$_q$-naphthyl substituted with 0–2 $R^a$; and
  —(CH$_2$)$_q$-5–10 membered heteroaryl consisting of carbon atoms and 1–4 heteroatoms selected from the group: O, S, and N, and substituted with 0–2 $R^a$;

$R^4$ is selected from the group: H,
  $C_{1-6}$ alkyl substituted with 0–3 $R^b$;
  phenyl substituted with 0–3 $R^b$;
  benzyl substituted with 0–3 $R^b$; and
  phenethyl substituted with 0–3 $R^b$;

$R^5$ is H or $Q$-$R^{5a}$;

Q is 0, 1, 2, or 3 amino acids;

$R^{5a}$ is selected from the group: —S(O) $R^6$, —S(O)$_2R^6$, —C(O)$R^6$, —C(O)O$R^8$, —C(O)NH$R^6$, $C_{1-3}$ alkyl-$R^{6a}$, $C_{2-6}$ alkenyl-$R^{6a}$, and $C_{2-6}$ alkynyl-$R^{6a}$;

$R^6$ is selected from the group:
  $C_{1-6}$ alkyl substituted with 0–3 $R^c$;
  phenyl substituted with 0–3 $R^c$;
  naphthyl substituted with 0–3 $R^c$;
  benzyl substituted with 0–3 $R^c$; and
  5–10 membered heteroaryl consisting of carbon atoms and 1–4 heteroatoms selected from the group: O, S, and N, substituted with 0–3 $R^c$;

$R^{6a}$ is selected from the group:
  phenyl substituted with 0–3 $R^c$;
  naphthyl substituted with 0–3 $R^c$;
  benzyl substituted with 0–3 $R^c$; and
  5–10 membered heteroaryl consisting of carbon atoms and 1–4 heteroatoms selected from the group: O, S, and N, substituted with 0–3 $R^c$;

$R^c$ is selected at each occurrence from the group:
$C_{1-4}$ alkyl, $C_{1-4}$ alkoxy, $CF_3$, $OCF_3$, Cl, F, Br, I, =O, OH, phenyl, $C(O)OR^7$, $NR^dR^d$, —CN, and $NO_2$;

$R^d$ is selected at each occurrence from the group: H and $CH_3$;

$R^7$ is selected at each occurrence from the group: H and $C_{1-6}$ alkyl;

$R^8$ is selected from the group: $C_{1-6}$ alkyl, benzyl, and $C_{3-6}$ cycloalkyl-methyl;

$R^{18}$ and $R^{19}$ at each occurrence are independently selected from H, $C_1$–$C_4$ alkyl, aryl($C_1$–$C_4$ alkyl)-, and $C_3$–$C_7$ cycloalkyl;

n is selected from the group: 1, 2, and 3; and q is selected from the group: 0, 1, and 2.

3. A compound according to claim 2 of Formula (I):

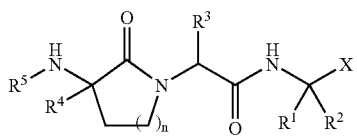

(I)

or a stereoisomer or pharmaceutically acceptable salt form thereof, wherein;

the lactam ring of Formula (I) is substituted with 0–2 $R^b$;

X is selected from the group: $B(OH)_2$ and $BY^1Y^2$;

$Y^1$ and $Y^2$ are independently selected from:
a) —OH,
b) $C_1$–$C_8$ alkoxy, or
when taken together, $Y^1$ and $Y^2$ form:
c) a cyclic boron ester comprising from 2 to 20 carbon atoms;

$R^1$ is selected from the group:
$C_{1-6}$ alkyl substituted with 0–3 halogen; and
$C_{2-6}$ alkenyl substituted with 0–3 halogen;

$R^a$ is selected at each occurrence from the group:
$C_{1-3}$ alkyl, $C_{3-6}$ cycloalkyl, Cl, F, Br, I, $CF_3$, OH, =O, $C_{1-6}$ alkoxy, SH, —S—$C_{1-6}$ alkyl;
phenyl substituted with 0–3 $R^b$;
naphthyl substituted with 0–3 $R^b$;
—O—$(CH_2)_q$-phenyl substituted with 0–3 $R^b$;
—O—$(CH_2)_q$-naphthyl substituted with 0–3 $R^b$; and
5–10 membered heteroaryl consisting of carbon atoms and 1–4 heteroatoms selected from the group: O, S, and N, and substituted with 0–3 $R^b$;

$R^b$ is selected at each occurrence from the group:
$C_{1-6}$ alkyl, Cl, F, Br, I, OH, $C_{1-6}$ alkoxy, —CN, —$NO_2$, $C(O)OR^7$, $NR^dR^d$, $CF_3$, $OCF_3$, and $C_{3-6}$ cycloalkyl;

$R^2$ is H;

$R^3$ is selected from the group:
$C_{1-6}$ alkyl substituted with 0–2 $R^a$;
$C_{2-6}$ alkenyl substituted with 0–2 $R^a$;
$C_{2-6}$ alkynyl substituted with 0–2 $R^a$;
—$(CH_2)_q$-$C_{3-6}$ cycloalkyl substituted with 0–2 $R^a$;
—$(CH_2)_q$-phenyl substituted with 0–2 $R^a$;
—$(CH_2)_q$-naphthyl substituted with 0–2 $R^a$; and
—$(CH_2)_q$-5–10 membered heteroaryl consisting of carbon atoms and 1–4 heteroatoms selected from the group: O, S, and N, and substituted with 0–2 $R^a$;

$R^4$ is selected from the group: H,
$C_{1-6}$ alkyl substituted with 0–3 $R^b$;
phenyl substituted with 0–3 $R^b$;
benzyl substituted with 0–3 $R^b$; and
phenethyl substituted with 0–3 $R^b$;

$R^5$ is H or Q-$R^{5a}$;

Q is 0, 1, 2, or 3 amino acids;

$R^{5a}$ is selected from the group: —$S(O)R^6$, —$S(O)_2R^6$, —$C(O)R^6$, —$C(O)OR^8$, —$C(O)NHR^6$, $C_{1-3}$ alkyl-$R^{6a}$, $C_{2-6}$ alkenyl-$R^{6a}$, and $C_{2-6}$ alkynyl-$R^{6a}$;

$R^6$ is selected from the group:
$C_{1-6}$ alkyl substituted with 0–3 $R^c$;
phenyl substituted with 0–3 $R^c$;
naphthyl substituted with 0–3 $R^c$;
benzyl substituted with 0–3 $R^c$; and
5–10 membered heteroaryl consisting of carbon atoms and 1–4 heteroatoms selected from the group: O, S, and N, substituted with 0–3 $R^c$;

$R^{6a}$ is selected from the group:
phenyl substituted with 0–3 $R^c$;
naphthyl substituted with 0–3 $R^c$;
benzyl substituted with 0–3 $R^c$; and
5–10 membered heteroaryl consisting of carbon atoms and 1–4 heteroatoms selected from the group: O, S, and N, substituted with 0–3 $R^c$;

$R^c$ is selected at each occurrence from the group:
$C_{1-4}$ alkyl, $C_{1-4}$ alkoxy, $CF_3$, $OCF_3$, Cl, F, Br, I, =O, OH, phenyl, C(O) $OR^7$, $NR^dR^d$, —CN, and $NO_2$;

$R^d$ is selected at each occurrence from the group: H and $CH_3$;

$R^7$ is selected at each occurrence from the group: H and $C_{1-6}$ alkyl;

$R^8$ is selected from the group: $C_{1-6}$ alkyl, benzyl, and $C_{3-6}$ cycloalkyl-methyl;

n is selected from the group: 1, 2, and 3; and q is selected from the group: 0, 1, and 2.

4. A compound according to claim 3, wherein the compound is of Formula (II):

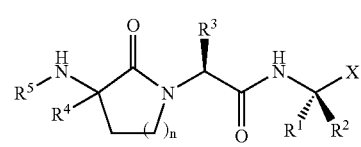

(II)

or a stereoisomer or pharmaceutically acceptable salt form thereof, wherein;

X is a boronic acid or a boron ester of formula $BY^1Y^2$;

$Y^1$ and $Y^2$ are independently selected from:
a) $C_1$–$C_6$ alkoxy, or
when taken together, $Y^1$ and $Y^2$ form:
b) a cyclic boron ester comprising from 2 to 16 carbon atoms;

$R^1$ is selected from the group: ethyl, n-propyl, n-butyl, allyl, 2,2,2-trifluoroethyl, 2,2-difluoroethyl, 3,3,3-trifluoropropyl, 4,4,4-trifluorobutyl, and 3-butenyl;

$R^a$ is selected at each occurrence from the group:
$C_{1-3}$ alkyl, $C_{3-6}$ cycloalkyl, Cl, F, Br, I, $CF_3$, OH, =O, $C_{1-6}$ alkoxy, SH, —S—$C_{1-6}$ alkyl;
phenyl substituted with 0–3 $R^b$;
naphthyl substituted with 0–3 $R^b$;
—O—$(CH_2)_q$-phenyl substituted with 0–3 $R^b$;
—O—$(CH_2)_q$-naphthyl substituted with 0–3 $R^b$; and
5–10 membered heteroaryl consisting of carbon atoms and 1–4 heteroatoms selected from the group: O, S, and N, and substituted with 0–3 $R^b$;

$R^b$ is selected at each occurrence from the group:
$C_{1-6}$ alkyl, Cl, F, Br, I, OH, $C_{1-6}$ alkoxy, —CN, —$NO_2$, $C(O)OR^7$, $NR^dR^d$, $CF_3$, $OCF_3$, and $C_{3-6}$ cycloalkyl;

$R^2$ is H;

$R^3$ is selected from the group:
- $C_{1-6}$ alkyl substituted with 0–2 $R^a$;
- $C_{2-6}$ alkenyl substituted with 0–2 $R^a$;
- $C_{2-6}$ alkynyl substituted with 0–2 $R^a$;
- —$(CH_2)_q$—$C_{3-6}$ cycloalkyl substituted with 0–2 $R^a$;
- —$(CH_2)_q$-phenyl substituted with 0–2 $R^a$;
- —$(CH_2)_q$-naphthyl substituted with 0–2 $R^a$;
- —$(CH_2)_q$-5–10 membered heteroaryl consisting of carbon atoms and 1–4 heteroatoms selected from the group: O, S, and N, and substituted with 0–2 $R^a$;

$R^4$ is selected from the group: H, methyl, ethyl, n-propyl, i-propyl, n-butyl, i-butyl, sec-butyl, t-butyl;
- phenyl substituted with 0–3 $R^b$;
- benzyl substituted with 0–3 $R^b$; and
- phenethyl substituted with 0–3 $R^b$;

$R^5$ is H or Q-$R^{5a}$;

Q is 0, 1, or 2 amino acids;

$R^{5a}$ is selected from the group: —S(O)$R^6$, —S(O)$_2R^6$, —C(O)$R^6$, —C(O)O$R^8$, —C(O)NH$R^6$, $C_{1-3}$ alkyl-$R^{6a}$, $C_{2-6}$ alkenyl-$R^{6a}$, and $C_{2-6}$ alkynyl-$R^{6a}$;

$R^6$ is selected from the group:
- $C_{1-6}$ alkyl substituted with 0–3 $R^c$;
- phenyl substituted with 0–3 $R^c$;
- naphthyl substituted with 0–3 $R^c$;
- benzyl substituted with 0–3 $R^c$; and
- 5–10 membered heteroaryl consisting of carbon atoms and 1–4 heteroatoms selected from the group: O, S, and N, substituted with 0–3 $R^c$;

$R^{6a}$ is selected from the group:
- phenyl substituted with 0–3 $R^c$;
- naphthyl substituted with 0–3 $R^c$;
- benzyl substituted with 0–3 $R^c$; and
- 5–10 membered heteroaryl consisting of carbon atoms and 1–4 heteroatoms selected from the group: O, S, and N, substituted with 0–3 $R^c$;

$R^c$ is selected at each occurrence from the group:
- $C_{1-4}$ alkyl, $C_{1-4}$ alkoxy, $CF_3$, $OCF_3$, Cl, F, Br, I, =O, OH, phenyl, C(O)O$R^7$, N$R^dR^d$, —CN, and $NO_2$;

$R^d$ is selected at each occurrence from the group: H and $CH_3$;

$R^7$ is selected at each occurrence from the group: H and $C_{1-6}$ alkyl;

$R^8$ is selected from the group: $C_{1-6}$ alkyl, benzyl, and $C_{3-6}$ cycloalkyl-methyl;

n is 1 or 2; and q is selected from the group: 0, 1, and 2.

5. A compound according to claim 4, wherein the compound is of Formula (II):

(II)

or a stereoisomer or pharmaceutically acceptable salt form thereof, wherein;

X is a boronic acid or boron ester, wherein the ester is a diol selected from the group: pinanediol, pinacol, 1,2-ethanediol, 1,3-propanediol, 1,2-propanediol, 2,3-butanediol, 1,2-diisopropylethanediol, 5,6-decanediol, and 1,2-dicyclohexylethanediol;

$R^1$ is selected from the group: ethyl, n-propyl, n-butyl, allyl, 2,2,2-trifluoroethyl, 2,2-difluoroethyl, 3,3,3-trifluoropropyl, 4,4,4-trifluorobutyl, and 3-butenyl;

$R^2$ is H;

$R^3$ is selected from the group: n-propyl, n-butyl, i-butyl, n-pentyl, neo-pentyl, cyclohexylmethyl, cyclopentylmethyl, phenyl, t-butoxymethyl, benzyloxymethyl, hydroxymethyl, methoxymethyl, ethoxymethyl, propoxymethyl, and i-propoxymethyl;

$R^4$ is selected from the group: methyl, ethyl, n-propyl, i-propyl, n-butyl, i-butyl, sec-butyl, t-butyl, phenyl, benzyl, and phenethyl;

$R^5$ is H or Q-$R^{5a}$;

Q is 0, 1, or 2 amino acids;

$R^{5a}$ is selected from the group: —S(O)$_2R^6$, —C(O)$R^6$, —C(O)O$R^8$, —C(O)NH$R^6$, and —$CH_2$—$R^{6a}$;

$R^6$ is selected from the group:
- methyl substituted with 0–3 $R^c$;
- ethyl substituted with 0–3 $R^c$;
- propyl substituted with 0–3 $R^c$;
- butyl substituted with 0–3 $R^c$;
- phenyl substituted with 0–3 $R^c$;
- naphthyl substituted with 0–3 $R^c$;
- benzyl substituted with 0–3 $R^c$; and
- quinolinyl substituted with 0–3 $R^c$;

$R^{6a}$ is selected from the group:
- phenyl substituted with 0–3 $R^c$;
- naphthyl substituted with 0–3 $R^c$;
- benzyl substituted with 0–3 $R^c$; and
- quinolinyl substituted with 0–3 $R^c$;

$R^c$ is selected at each occurrence from the group:
- methyl, ethyl, n-propyl, i-propyl, n-butyl, i-butyl, t-butyl, methoxy, ethoxy, propoxy, i-propoxy, $CF_3$, $OCF_3$, Cl, F, Br, I, OH, phenyl, C(O)OH, $NH_2$, —CN, and $NO_2$;

$R^8$ is methyl, ethyl, n-propyl, i-propyl, n-butyl, i-butyl, t-butyl, phenyl, and benzyl; and n is 1 or 2.

6. A compound according to claim 4, wherein the compound is of Formula (II):

(II)

or a stereoisomer or pharmaceutically acceptable salt form thereof, wherein;

X is a boronic acid or a boron ester of formula B$Y^1Y^2$;

$Y^1$ and $Y^2$ are individually selected from $C_1$–$C_6$ alkoxy, or when taken together, $Y^1$ and $Y^2$ form a cyclic boron ester where said chain or ring contains from 2 to 14 carbon atoms;

$R^1$ is selected from the group: ethyl, n-propyl, n-butyl, allyl, 2,2,2-trifluoroethyl, 2,2-difluoroethyl, 3,3,3-trifluoropropyl, 4,4,4-trifluorobutyl, and 3-butenyl;

$R^2$ is H;

$R^3$ is selected from the group: i-butyl, neo-pentyl, cyclohexylmethyl, t-butoxymethyl, benzyloxymethyl, hydroxymethyl, and phenyl;

$R^4$ is selected from the group: ethyl, n-propyl, i-propyl, R-2-butyl, S-2-butyl, phenyl, benzyl, and phenethyl;

$R^5$ is selected from the group: H,
  benzyl,
  m-methylphenylsulfonyl,
  m-trifluoromethylphenylsulfonyl,
  p-i-propylphenylsulfonyl,
  p-propylphenylsulfonyl,
  p-t-butylphenylsulfonyl,
  p-carboxylphenylsulfonyl,
  4-(1,1')biphenylsulfonyl,
  1-naphthylsulfonyl,
  2-naphthylsulfonyl,
  8-quinolinylsulfonyl,
  pyrazin-2-ylcarbonyl,
  n-butylsulfonyl,
  N-phenylaminocarbonyl,
  N-(p-n-butylphenyl)aminocarbonyl,
  benzyloxycarbonyl,
  methoxycarbonyl,
  t-butyloxycarbonyl,
  benzoyl,
  methanesulfonyl,
  phenylsulfonyl,
  o-nitrophenylsulfonyl,
  m-nitrophenylsulfonyl, and
  m-aminophenylsulfonyl; and
n is 1 or 2.

7. A compound according to claim 6, wherein;

X is a boronic acid or boron ester, wherein the ester is a diol selected from the group: pinanediol, pinacol, 1,2-ethanediol, 1,3-propanediol, 1,2-propanediol, 2,3-butanediol, 1,2-diisopropylethanediol, 5,6-decanediol, and 1,2-dicyclohexylethanediol;

$R^1$ is selected from the group: ethyl, n-propyl, n-butyl, allyl, 2,2,2-trifluoroethyl, 2,2-difluoroethyl, 3,3,3-trifluoropropyl, 4,4,4-trifluorobutyl, and 3-butenyl;

$R^2$ is H;

$R^3$ is selected from the group: i-butyl, neo-pentyl, cyclohexylmethyl, t-butoxymethyl, benzyloxymethyl, hydroxymethyl, and phenyl;

$R^4$ is selected from the group: ethyl, n-propyl, i-propyl, R-2-butyl, S-2-butyl, phenyl, benzyl, and phenethyl;

$R^5$ is selected from the group: H,
  benzyl,
  m-methylphenylsulfonyl,
  m-trifluoromethylphenylsulfonyl,
  p-i-propylphenylsulfonyl,
  p-propylphenylsulfonyl,
  p-t-butylphenylsulfonyl,
  p-carboxylphenylsulfonyl,
  4-(1,1')biphenylsulfonyl,
  1-naphthylsulfonyl,
  2-naphthylsulfonyl,
  8-quinolinylsulfonyl,
  pyrazin-2-ylcarbonyl,
  n-butylsulfonyl,
  N-phenylaminocarbonyl,
  N-(p-n-butylphenyl)aminocarbonyl,
  benzyloxycarbonyl,
  methoxycarbonyl,
  t-butyloxycarbonyl,
  benzoyl,
  methanesulfonyl,
  phenylsulfonyl,
  o-nitrophenylsulfonyl,
  m-nitrophenylsulfonyl, and
  m-aminophenylsulfonyl; and
n is 1 or 2.

8. A compound according to claim 1, wherein the compound is selected from the group:

(1R)-1-({(2S)-3-cyclohexyl-2-(3-isopropyl-3-({(2S)-3-methyl-2-((2-pyrazinylcarbonyl)amino)butanoyl}amino)-2-oxo-1-pyrrolidinyl)propanoyl}amino)-3-butenylboronic acid (+)-pinanediol ester;

(1R)-1-({(2S)-3-cyclohexyl-2-(3-isopropyl-3-({(2S)-3-methyl-2-((2-pyrazinylcarbonyl)amino)butanoyl}amino)-2-oxo-1-piperidinyl)propanoyl}amino)-3-butenylboronic acid (+)-pinanediol ester;

(1R)-1-(({3-((methylsulfonyl)amino)-2-oxohexahydro-1H-azepin-1-yl}acetyl)amino)propylboronic acid (+)-pinanediol ester;

(1R)-1-{((2S)-2-(3-amino-3-isopropyl-2-oxo-1-pyrrolidinyl)-3-cyclohexylpropanoyl)amino}propylboronic acid (+)-pinanediol ester hydrochloride;

1R)-1-(((2S)-2-{3-(((1,1'-biphenyl)-4-ylsulfonyl)amino)-3-isopropyl-2-oxo-1-pyrrolidinyl}-3-cyclohexylpropanoyl)amino)propylboronic acid (+)-pinanediol ester;

(1R)-1-{((2S)-3-cyclohexyl-2-(3-isopropyl-2-oxo-3-{((4-propylphenyl)sulfonyl)amino}-1-pyrrolidinyl)propanoyl)amino}propylboronic acid (+)-pinanediol ester;

(1R)-1-(((2S)-3-cyclohexyl-2-{3-isopropyl-3-((1-naphthylsulfonyl)amino)-2-oxo-1-pyrrolidinyl}propanoyl)amino)propylboronic acid (+)-pinanediol ester;

(1R)-1-(((2S)-2-{3-((anilinocarbonyl)amino)-3-isopropyl-2-oxo-1-pyrrolidinyl}-3-cyclohexylpropanoyl)amino)propylboronic acid (+)-pinanediol ester;

(1R)-1-{((2S)-3-cyclohexyl-2-(3-isopropyl-3-{((3-methylphenyl)sulfonyl)amino}-2-oxo-1-pyrrolidinyl)propanoyl)amino}propylboronic acid (+)-pinanediol ester;

(1R)-1-{((2S)-3-cyclohexyl-2-(3-isopropyl-3-{((3-methylphenyl)sulfonyl)amino}-2-oxo-1-pyrrolidinyl)propanoyl)amino}propylboronic acid (1R)-1-{((3-{((benzyloxy)carbonyl)amino}-3-isopropyl-2-oxo-1-pyrrolidinyl)(phenyl)acetyl)amino}propylboronic acid (+)-pinanediol ester;

(1R)-1-{((3-amino-3-isopropyl-2-oxo-1-pyrrolidinyl)(phenyl)acetyl)amino}propylboronic acid (+)-pinanediol ester hydrochloride;

(1R)-1-{({3-isopropyl-3-((methylsulfonyl)amino)-2-oxo-1-pyrrolidinyl}(phenyl)acetyl)amino}propylboronic acid (+)-pinanediol ester;

(1R)-1-{((3-isopropyl-2-oxo-3-{((4-propylphenyl)sulfonyl)amino}-1-pyrrolidinyl)(phenyl)acetyl)amino}propylboronic acid (+)-pinanediol ester;

(1R)-1-{((2S)-2-(3-{((benzyloxy)carbonyl)amino}-3-isopropyl-2-oxo-1-pyrrolidinyl)-4-methylpentanoyl)amino}propylboronic acid (+)-pinanediol ester;

(1R)-1-{((2S)-2-(3-amino-3-isopropyl-2-oxo-1-pyrrolidinyl)-4-methylpentanoyl)amino}propylboronic acid (+)-pinanediol ester hydrochloride;

(1R)-1-(((2S)-2-{3-isopropyl-3-((methylsulfonyl)amino)-2-oxo-1-pyrrolidinyl}-4-methylpentanoyl)amino)propylboronic acid (+)-pinanediol ester;

(1R)-1-{((2S)-2-(3-isopropyl-2-oxo-3-{((4-propyphenyl)sulfonyl)amino}-1-pyrrolidinyl)-4-methylpentanoyl)amino}propylboronic acid (+)-pinanediol ester;

(1R)-1-({(2S)-3-cyclohexyl-2-(3-ethyl-3-({(2S)-3-methyl-2-((2-pyrazinylcarbonyl)amino)butanoyl}amino)-2-oxo-1-pyrrolidinyl)propanoyl}amino)-3-butenylboronic acid (+)-pinanediol ester;

(1R)-1-{((2S)-2-(3-{((benzyloxy)carbonyl)amino}-3-isopropyl-2-oxo-1-piperidinyl)-3-cyclohexylpropanoyl)amino}propylboronic acid (+)-pinanediol ester;

(1R)-1-{(({3-((tert-butoxycarbonyl)amino)-3-isopropyl-2-oxo-1-piperidinyl}(phenyl)acetyl)amino}propylboronic acid (+)-pinanediol ester;

(1R)-1-{(((3-amino-3-isopropyl-2-oxo-1-piperidinyl)(phenyl)acetyl)amino}propylboronic acid hydrochloride (+)-pinanediol ester;

(1R)-1-{(({3-isopropyl-3-((methoxycarbonyl)amino)-2-oxo-1-piperidinyl}(phenyl)acetyl)amino}propylboronic acid (+)-pinanediol ester;

(1R)-1-{(((3-(benzoylamino)-3-isopropyl-2-oxo-1-piperidinyl)(phenyl)acetyl)amino}propylboronic acid (+)-pinanediol ester;

(1R)-1-{(({3-isopropyl-3-((methylsulfonyl)amino)-2-oxo-1-piperidinyl}(phenyl)acetyl)amino}propylboronic acid (+)-pinanediol ester; and (1R)-1-{(((3-isopropyl-3-{((3-methylphenyl)sulfonyl)amino}-2-oxo-1-piperidinyl)(phenyl)acetyl)amino}propylboronic acid (+)-pinanediol ester;

or a pharmaceutically acceptable salt form thereof.

9. A pharmaceutical composition comprising a pharmaceutically acceptable carrier and a therapeutically effective amount of a compound of claim 1 or pharmaceutically acceptable salt form thereof.

10. A pharmaceutical composition comprising a pharmaceutically acceptable carrier and a therapeutically effective amount of a compound of claim 2 or pharmaceutically acceptable salt form thereof.

11. A pharmaceutical composition comprising a pharmaceutically acceptable carrier and a therapeutically effective amount of a compound of claim 3 or pharmaceutically acceptable salt form thereof.

12. A pharmaceutical composition comprising a pharmaceutically acceptable carrier and a therapeutically effective amount of a compound of claim 4 or pharmaceutically acceptable salt form thereof.

13. A pharmaceutical composition comprising a pharmaceutically acceptable carrier and a therapeutically effective amount of a compound of claim 5 or pharmaceutically acceptable salt form thereof.

14. A pharmaceutical composition comprising a pharmaceutically acceptable carrier and a therapeutically effective amount of a compound of claim 6 or pharmaceutically acceptable salt form thereof.

15. A pharmaceutical composition comprising a pharmaceutically acceptable carrier and a therapeutically effective amount of a compound of claim 7 or pharmaceutically acceptable salt form thereof.

16. A pharmaceutical composition comprising a pharmaceutically acceptable carrier and a therapeutically effective amount of a compound of claim 8 or pharmaceutically acceptable salt form thereof.

17. A method of inhibiting HCV NS3 protease which comprises contacting HCV NS3 protease with a therapeutically effective amount of a compound of claim 1 or pharmaceutically acceptable salt form thereof.

18. A method of inhibiting HCV NS3 protease which comprises contacting HCV NS3 protease with a therapeutically effective amount of a compound of claim 2 or pharmaceutically acceptable salt form thereof.

19. A method of inhibiting HCV NS3 protease which comprises contacting HCV NS3 protease with a therapeutically effective amount of a compound of claim 3 or pharmaceutically acceptable salt form thereof.

20. A method of inhibiting HCV NS3 protease which comprises contacting HCV NS3 protease with a therapeutically effective amount of a compound of claim 4 or pharmaceutically acceptable salt form thereof.

21. A method of inhibiting HCV NS3 protease which comprises contacting HCV NS3 protease with a therapeutically effective amount of a compound of claim 5 or pharmaceutically acceptable salt form thereof.

22. A method of inhibiting HCV NS3 protease which comprises contacting HCV NS3 protease with a therapeutically effective amount of a compound of claim 6 or pharmaceutically acceptable salt form thereof.

23. A method of inhibiting HCV NS3 protease which comprises contacting HCV NS3 protease with a therapeutically effective amount of a compound of claim 7 or pharmaceutically acceptable salt form thereof.

24. A method of inhibiting HCV NS3 protease which comprises contacting HCV NS3 protease with a therapeutically effective amount of a compound of claim 8 or pharmaceutically acceptable salt form thereof.

25. A method of treating HCV infection which comprises administering to a host in need of such treatment a therapeutically effective amount of a compound of claim 1 or pharmaceutically acceptable salt form thereof.

* * * * *

SEQUENCE LISTING

```
<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans
<220> FEATURE:
<221> NAME/KEY: ACT_SITE
<222> LOCATION: (1)..(1)
<223> OTHER INFORMATION:
<220> FEATURE:
<221> NAME/KEY: misc_feature
<222> LOCATION: (3)..(3)
<223> OTHER INFORMATION: diphenylalanine
<220> FEATURE:
<221> NAME/KEY: misc_feature
<222> LOCATION: (5)..(5)
<223> OTHER INFORMATION: cyclohexylalanine

<400> SEQUENCE: 1

Asp Glu Xaa Glu Xaa Cys
1               5

<210> SEQ ID NO 2
<211> LENGTH: 6
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans
<220> FEATURE:
<221> NAME/KEY: MOD_RES
<222> LOCATION: (1)..(1)
<223> OTHER INFORMATION: Acetylation
<220> FEATURE:
<221> NAME/KEY: misc_feature
<222> LOCATION: (2)..(2)
<223> OTHER INFORMATION: D-Aspartic Acid

<400> SEQUENCE: 2

Asp Xaa Ile Val Pro Cys
1               5

<210> SEQ ID NO 3
<211> LENGTH: 5
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
```

```
      materials well known to ordinarily skilled artisans

<400> SEQUENCE: 3

Met Gly Ala Gln His
1               5

<210> SEQ ID NO 4
<211> LENGTH: 15
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans

<400> SEQUENCE: 4

Met Arg Gly Ser His His His His His His Met Gly Ala Gln His
1               5                   10                  15

<210> SEQ ID NO 5
<211> LENGTH: 6
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans
<220> FEATURE:
<221> NAME/KEY: misc_feature
<222> LOCATION: (6)..(6)
<223> OTHER INFORMATION: 2-amino-4-penten-boronic acid

<400> SEQUENCE: 5

Asp Glu Val Val Pro Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans
<220> FEATURE:
<221> NAME/KEY: ACETYLATION
<222> LOCATION: (1)..(1)
<223> OTHER INFORMATION: Acetylation
<220> FEATURE:
<221> NAME/KEY: AMIDATION
<222> LOCATION: (5)..(5)
<223> OTHER INFORMATION: para-nitroanaline

<400> SEQUENCE: 6

Asp Glu Glu Ala Cys
1               5

<210> SEQ ID NO 7
<211> LENGTH: 23
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans

<400> SEQUENCE: 7

Lys Lys Gly Ser Val Val Ile Val Gly Arg Ile Val Leu Ser Gly Lys
1               5                   10                  15
```

```
Pro Ala Ile Ile Pro Lys Lys
            20

<210> SEQ ID NO 8
<211> LENGTH: 9
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans
<220> FEATURE:
<221> NAME/KEY: ACETYLATION
<222> LOCATION: (1)..(1)
<223> OTHER INFORMATION: acetyl group
<220> FEATURE:
<221> NAME/KEY: MOD_RES
<222> LOCATION: (3)..(3)
<223> OTHER INFORMATION: Aspartic acid modified with EDANS,
      5-[(2'-aminoethyl)amino]naphthylene sulfonic acid
<220> FEATURE:
<221> NAME/KEY: MISC_FEATURE
<222> LOCATION: (6)..(6)
<223> OTHER INFORMATION: 2-amino butyric acid bonded through an ester
      group
<220> FEATURE:
<221> NAME/KEY: MOD_RES
<222> LOCATION: (9)..(9)
<223> OTHER INFORMATION: Lysine modified by Dabcyl;
      4-[[4'(dimethylamino)phenyl]azo]benzoic acid

<400> SEQUENCE: 8

Asp Glu Asp Glu Glu Xaa Ala Ser Lys
1               5
```